United States Patent [19]
Ellis et al.

[11] Patent Number: 5,710,250
[45] Date of Patent: Jan. 20, 1998

[54] CALCIUM CHANNEL ALPHA 2 SUBUNIT POLYPEPTIDES

[75] Inventors: Steven Bradley Ellis, San Diego; Mark E. Williams, Carlsbad; Michael Miller Harpold, San Diego; Jean Sartor, San Diego; Robert Brenner, San Diego, all of Calif.

[73] Assignee: SIBIA Neurosciences, Inc., La Jolla, Calif.

[21] Appl. No.: 435,675

[22] Filed: May 5, 1995

Related U.S. Application Data

[60] Continuation of Ser. No. 314,083, Sep. 28, 1994, which is a division of Ser. No. 914,231, Jul. 13, 1992, Pat. No. 5,407,820, which is a continuation of Ser. No. 603,751, filed as PCT/US89/01408, Apr. 4, 1989, abandoned, which is a continuation-in-part of Ser. No. 176,899, Apr. 4, 1988, abandoned.

[51] Int. Cl.$^6$ .............. C07K 14/435; C07K 14/705; C12N 15/12; C12N 15/85
[52] U.S. Cl. .............. 530/350; 435/69.1; 536/23.5
[58] Field of Search .............. 530/350; 435/69.1; 536/23.5

[56] References Cited

U.S. PATENT DOCUMENTS

| | | | |
|---|---|---|---|
| 4,788,135 | 11/1988 | Davis et al. | 435/320.1 |
| 4,912,202 | 3/1990 | Campbell et al. | 530/387 |
| 4,954,436 | 9/1990 | Froehner et al. | 530/350 |
| 5,051,403 | 9/1991 | Miljanich et al. | 514/12 |
| 5,189,020 | 2/1993 | Miljanich et al. | 514/12 |
| 5,264,371 | 11/1993 | Miljanich et al. | 436/503 |
| 5,424,218 | 6/1995 | Miljanich et al. | 436/503 |

FOREIGN PATENT DOCUMENTS

| | | |
|---|---|---|
| 9202639 | 2/1992 | WIPO. |
| 9402511 | 2/1994 | WIPO. |
| 9504144 | 2/1995 | WIPO. |

OTHER PUBLICATIONS

Barhanin, et al., "The Calcium Channel Antagonists Receptor from Rabbit Skeletal Muscle: Reconstruction after Purification and Subunit Characterization," *Eur. J. Biochem.*, 164:525–531 (1987).

Borsotto, et al., "The 1,4-dihydropyridine receptor associated with the skeletal muscle voltage-dependent $Ca^{2+}$ channel," *J. Biol. Chem.*, 260(26):14255–14263 (1985).

Brust, et al., "Human Neuronal Voltage-Dependent Calcium Channels: Studies on Subunit Structure and Role in Channel Assembly," *Neuropharmacology*, 32(11):1089–1102 (1993).

Catterall, et al., "Molecular Properties of Dihydropyridine-sensitive Calcium Channels in Skeletal Muscle," *J. Biol. Chem.*, 263:3535–3538 (1988).

Claudio, et al., "Stable expression of transfected *Torpedo*acetylcholine receptor αsubunits in mouse fibroblast L cells," *Proc.Natl.Acad.Sci.*, 84:5967–5971 (1987).

Claudio, et al., "Genetic reconstitution of functional acetylcholine receptor channels in mouse fibroblasts,"*Science*, 238:1688–1694 (1987).

Cooper, et al., "Purification and characterization of the dihydropyridine–sensitive voltage–dependent calcium channel from cardaic tissue," *J.Biol.Chem.*, 262(2):509–512 (1987).

Curran and Morgan, "Barium Modulates *c–fos*Expression and Post–Translational Modification,"*Proc. Natl. Acad. Sci. USA*, 83:8521–8524 (1986).

Curtis, et al., "Reconstruction of the voltage–sensitive calcium channel purified from skeletal muscle transverse tubules," *Biochemistry*, 25:3077–3083 (1986).

Curtis, et al., "Purification of the calcium antagonist receptor of the voltage–sensitive calcium channel from skeletal muscle transverse tubules," *Biochemistry*, 23(10):2113–2118 (1984).

Dascal, et al., "Expression of modulation of voltage–gated calcium channels after RNA injection in *Xenopus oocytes*," *Science*, 231:1147–1150 (1986).

Ellis, et al., "Sequence and expression of mRNAs encoding the $\alpha_1$and $\alpha_2$subunits of DHP–sensitive calcium channel," *Science*, 241:1661–1664 (1988).

Faramisco, et al., "Optimal spatial requirements for the location of basic residues in peptide substrates for the cyclic AMP–dependent protein kinase," *J. Biol. Chem.*, 225(9):4240–4245 (1980).

Fisch, et al., "*c–fos* Sequences Necessary for Basal Expression and Induction by Epidermal Growth Factor, 12–O–Tetradecanoyl Phorbol–13–Acetate, and the Calcium Ionophore," *Mol. Cell. Biol.*, 7:3490–3502 (1987).

Gustin, et al., "Ion Channels in Yeast," *Science*, 233:1195–1197 (1986).

Hofmann, et al., "Regulation of the L–type calcium channel," *TIPS*, 8:393–398 (1987).

Hubbard, et al., "Synthesis and processing of asparagine–linked oligosaccharides[1,2]," *Ann. Rev. Biochem.*, 50:555–583 (1981).

Imagawa, et al., "Phosphorylation of the 1,4–dihydropyridine receptor of the voltage–dependent $Ca^{2+}$ channel by an intrinsic protein kinase in isolated triads from rabbit skeletal muscle,"*J. Biol. Science*, 262(17):8333–8339 (1987).

Kozak, "An analysis of 5'–noncoding sequences from 699 vertebrate messenger RNAs," *Nucleic Acids Research*, 15(20):8125–8148 (1987).

Lang, et al., "The Effect of Myasthenic Syndrome Antibody on Presynaptic Channels in the Mouse," *J. Physiol.*, 390:257–270 (1987).

(List continued on next page.)

*Primary Examiner*—Stephen Walsh
*Assistant Examiner*—Daryl A. Basham
*Attorney, Agent, or Firm*—Stephanie L. Seidman; Brown Martin Haller & McClain LLP

[57] ABSTRACT

$\alpha_1$- and $\alpha_2$- protein subunits of voltage-dependent calcium channels are provided.

8 Claims, 20 Drawing Sheets

OTHER PUBLICATIONS

Leung, et al., "Monoclonal antibody characterization of the 1,4–dihydropyridine receptor of rabbit skeletal muscle," *Ann.N.Y.Acad.Sci.*, 522:43–46 (1988).

Leung, et al., "Structural characterization of the 1,4–dihydropyridine receptor of the voltage–dependent $Ca^{2+}$ channel from rabbit skeletal muscle," *J.Biol.Chem.*, 262(17):7943–7946 (1987).

Leung, et al., "Biochemical and ultrastructural characterization of the 1,4–dihydropyridine receptor from rabbit skeletal muscle," *J. Biol. Chem.*, 263(2):994–1101 (1988).

Meshi, et al., "Nucleotide sequence of the 30K protein cistron of cowpea strain of tobacco mosaic virus," *Nucleic Acids Research*, 10:6111–6117 (1982).

Mierendorf, et al., "Gene Isolation by Screening λgt 11 Libraries with Antibodies," *Methods in Enzymology*, 152:458–469 (1986).

Miller, "Multiple calcium channels and neuronal function," *Science*, 234:46–52 (1987).

Morton and Froehner, "Monoclonal Antibody Identifies a 200–kDA Subunit of the Dihydropyridine–sensitive Calcium Channel," *J. Biol. Chem.*, 262:11904–11907 (1987).

Nakayama, et al., "Purification of a Putative $Ca^{+2}$ Channel Protein from Rabbit Skeletal Muscle," *J. Biol. Chem.*, 262:6572–6576 (1987).

Nikaido, et al., "Molecular cloning of cDNA encoding human interleukin-2 receptor," *Nature*, 311:631–636 (1984).

Noda, et al., "Existence of distinct sodium channel messenger RNAs in rat brain," *Nature*, 320:188–192 (1986).

Noda, et al., "Expression of functional sodium channels from cloned cDNA," *Nature*, 322:826–828 (1986).

Schmid, et al., "Immunochemical analysis of subunit structure of 1,4–dihydropyridine receptors associated with voltage–dependent $Ca^{2+}$ channels in skeletal, cardiac, and smooth muscles," *Biochemistry*, 25:3492–3495 (1986).

Seager, et al., *Ann. N.Y. Acad. Sci.*, 522:43–46 (1988).

Sharp, et al., "Identification and Characterization of the Dihydropyridine–binding Subunit of the Skeletal Muscle Dihydropyridine Receptor," *J. Biol. Chem.*, 62:12309–12315 (1987).

Smith, et al., "Calcium channel activity in a purified dihydropyridine–receptor preparation of skeletal muscle," *Biochemistry*, 26:7182–7188 (1987).

Striessnig, et al., "Photoaffinity labelling of the phenylalkylamine receptor of the skeletal muscle transverse–tubule calcium channel," *FEBS Letters*, 212:247–253 (1987).

Takahashi and Catterall, "Dihydropyridine–sensitive Calcium Channels in Cardiac and Skeletal Muscle Membranes: Studies with Antibodies against the Alpha Subunits," *Biochemistry*, 26:5518–5526 (1987).

Takahashi and Catterall, "Identification of an αsubunit of dihydropyridine–sensitive brain calcium channels," *Science*, 236:88–91 (1987).

Takahashi, et al., "Subunit Structure of Dihydropyridine–sensitive Calcium Channels from Skeletal Muscle," *Proc. Natl. Acad. Sci. USA*, 84:5478–5482 (1987).

Takahashi et al., "Dihydropyridine–sensitive calcium channels in cardaic and skeletal muscle membranes: Studies with antibodies against the α–subunits," *Biochemistry*, 26(17):1518–1526 (1987).

Tanabe, et al., "Primary Structure of the Receptor for Calcium Channel Blockers from Skeletal Muscle," *Nature*, 328:313–318 (1987).

Vaghy, et al., "Mechanism of action of calcium channel modulator drugs," *Ann.N.Y.Acad.Sci.*, 522:176–186 (1988).

Vaghy, et al., "Identification of a Novel 1,4–Dihydropyridine–and Phenylalkylamine–binding Polypeptide in Calcium Channel Preparations," *J. Biol. Chem.*, 262:14337–14342 (1987).

von Heijne, "Signal sequences: the limits of variation," *J. Mol. Biol.*, 184:99–105 (1985).

Williams, "Structure and functional expression of $\alpha_1$, $\alpha_2$ and $\beta$subunits of a novel human neuronal calcium channel subtype," *Neuron*, 8:71–84 (1992).

Williams, et al., "Structure and functional characterization of neuronal $\alpha_{1E}$ calcium channel subtypes," *J. Biol. Chem.*, 269(35):22347–22357 (1994).

Williams, et al., "Structure and Functional Expression of an ω–Conotoxin–Sensitive Human N–Type Calcium Channel," *Science*, 257:389–395 (1992).

Wood, "Gene cloning based on long oligonucleotide probes," *Methods in Enzymology*, 152:443–447 (1987).

FIGURE 1a

```
                                           GCGGGGAA CACTGGGGAC -61
GCAGGGAAGA GAGGGCCGCG GGGTGGGGGA GCAGCAGGAA GCGCCGTGGC CAGGGAAGCC -1

ATG GAG CCA TCC TCA CCC CAG GAT GAG GGC CTG AGG AAG AAA CAG CCC    48
MET GLU PRO SER SER PRO GLN ASP GLU GLY LEU ARG LYS LYS GLN PRO
              5                   10                  15

AAG AAG CCC CTG CCC GAG GTC CTG CCC AGG CCG CCG CGG GCT CTG TTC    96
LYS LYS PRO LEU PRO GLU VAL LEU PRO ARG PRO PRO ARG ALA LEU PHE
            20                  25                  30

TGC CTG ACC CTG CAG AAC CCG CTG AGG AAG GCG TGC ATC AGC ATC GTG   144
CYS LEU THR LEU GLN ASN PRO LEU ARG LYS ALA CYS ILE SER ILE VAL
35                  40                  45

GAA TGG AAA CCC TTC GAG ACC ATC ATC CTG CTC ACC ATC TTT GCC AAC   192
GLU TRP LYS PRO PHE GLU THR ILE ILE LEU LEU THR ILE PHE ALA ASN
        50                  55                  60

TGT GTG GCC CTG GCC GTG TAC CTG CCC ATG CCC GAG GAT GAC AAC AAC   240
CYS VAL ALA LEU ALA VAL TYR LEU PRO MET PRO GLU ASP ASP ASN ASN
65                  70                  75           *      80

TCC CTG AAC CTG GGC CTG GAG AAG CTG GAG TAC TTC TTC CTC ACC GTC   288
SER LEU ASN LEU GLY LEU GLU LYS LEU GLU TYR PHE PHE LEU THR VAL
                    85                  90                  95

TTC TCC ATC GAA GCC GCC ATG AAG ATC ATC GCC TAC GGC TTC CTG TTC   336
PHE SER ILE GLU ALA ALA MET LYS ILE ILE ALA TYR GLY PHE LEU PHE
            100                 105                 110

CAC CAG GAC GCC TAC CTG CGC AGC GGC TGG AAC GTG CTG GAC TTC ATC   384
HIS GLN ASP ALA TYR LEU ARG SER GLY TRP ASN VAL LEU ASP PHE ILE
            115                 120                 125

ATC GTC TTC CTG GGG GTC TTC ACG GCG ATT CTG GAA CAG GTC AAC GTC   432
ILE VAL PHE LEU GLY VAL PHE THR ALA ILE LEU GLU GLN VAL ASN VAL
        130                 135                 140

ATC CAG AGC AAC ACG GCC CCG ATG AGC AGC AAA GGA GCC GGC CTG GAC   480
ILE GLN SER ASN THR ALA PRO MET SER SER LYS GLY ALA GLY LEU ASP
145                 150                 155                 160

GTC AAG GCC CTG AGG GCC TTC CGT GTG CTC AGA CCC CTC CGG CTG GTG   528
VAL LYS ALA LEU ARG ALA PHE ARG VAL LEU ARG PRO LEU ARG LEU VAL
            165                 170                 175
```

FIGURE 1b

```
TCG GGG GTG|CCT AGT TTG CAG GTG GTC CTC AAC TCC ATC TTC AAG GCC  576
SER GLY VAL|PRO SER LEU GLN VAL VAL LEU ASN SER ILE PHE LYS ALA
        180         185                     190

ATG CTC CCC CTG TTC CAC|ATC GCC CTG CTC GTC CTC TTC ATG GTC ATC  624
MET LEU PRO LEU PHE HIS|ILE ALA LEU LEU VAL LEU PHE MET VAL ILE
        195                 200                 205

ATC TAC GCC ATC ATC GGG CTG GAG CTC TTC|AAG GGC AAG ATG CAC AAG  672
ILE TYR ALA ILE ILE GLY LEU GLU LEU PHE|LYS GLY LYS MET HIS LYS
        210             215                 220

ACC TGC TAC TAC ATC GGG ACA GAC ATC GTG GCC ACA GTG GAG AAT GAG  720
THR CYS TYR TYR ILE GLY THR ASP ILE VAL ALA THR VAL GLU ASN GLU
225                 230                 235                 240

AAG CCC TCG CCC TGC GCT AGG ACG GGC TCG GGG CGC CCC TGC ACC ATC  768
LYS PRO SER PRO CYS ALA ARG THR GLY SER GLY ARG PRO CYS THR ILE
                245                 250                 255

AAC GGC AGC GAG TGC CGG GGC GGC TGG CCG GGG CCC AAC CAC GGC ATC  816
ASN GLY SER GLU CYS ARG GLY GLY TRP PRO GLY PRO ASN HIS GLY ILE
 *          260                 265                 270

ACG CAC TTC GAC AAC TTC GGC TTC TCC ATG CTC ACC GTG TAC CAG TGC  864
THR HIS PHE ASP ASN PHE GLY PHE SER MET LEU THR VAL TYR GLN CYS
            275                 280                 285

ATC ACC ATG GAG GGC TGG ACA GAT GTC CTC TAC TGG GTC AAC GAT GCC  912
ILE THR MET GLU GLY TRP THR ASP VAL LEU TYR TRP VAL ASN ASP ALA
        290                 295                 300

ATC GGG AAC GAG TGG|CCC TGG ATC TAC TTT GTC ACT CTC ATC CTG CTG  960
ILE GLY ASN GLU TRP|PRO TRP ILE TYR PHE VAL THR LEU ILE LEU LEU
305                 310                 315                 320

GGG TCC TTC TTC ATC CTC AAC CTG GTG CTG GGC GTC CTG AGT|GGG GAA 1008
GLY SER PHE PHE ILE LEU ASN LEU VAL LEU GLY VAL LEU SER|GLY GLU
                325                 330                 335

TTC ACC AAG GAG CGG GAG AAG GCC AAG TCC AGG GGA ACC TTC CAG AAG 1056
PHE THR LYS GLU ARG GLU LYS ALA LYS SER ARG GLY THR PHE GLN LYS
        340                 345                 350

CTG CGG GAG AAG CAG CAG CTG GAG GAG GAC CTT CGG GGC TAC ATG AGC 1104
LEU ARG GLU LYS GLN GLN LEU GLU GLU ASP LEU ARG GLY TYR MET SER
        355                 360                 365
```

FIGURE 1c

```
TGG ATC ACG CAG GGC GAG GTC ATG GAC GTG GAG GAC CTG AGA GAA GGA   1152
TRP ILE THR GLN GLY GLU VAL MET ASP VAL GLU ASP LEU ARG GLU GLY
    370             375             380

AAG CTG TCC TTG GAA GAG GGA GGC TCC GAC ACG GAA AGC CTG TAC GAA   1200
LYS LEU SER LEU GLU GLU GLY GLY SER ASP THR GLU SER LEU TYR GLU
385             390             395                         400

ATC GAG GGC TTG AAC AAA ATC ATC CAG TTC ATC CGA CAC TGG AGG CAG   1248
ILE GLU GLY LEU ASN LYS ILE ILE GLN PHE ILE ARG HIS TRP ARG GLN
                405             410             415

TGG AAC CGT GTC TTT CGC TGG AAG TGC CAT GAC CTG GTG AAG TCG AGA   1296
TRP ASN ARG VAL PHE ARG TRP LYS CYS HIS ASP LEU VAL LYS SER ARG
            420             425             430
```

```
GTC TTC TAC TGG CTG GTC ATC CTG ATC GTG GCC CTC AAC ACC CTG TCC   1344
VAL PHE TYR TRP LEU VAL ILE LEU ILE VAL ALA LEU ASN THR LEU SER
            435             440             445
```

```
ATC GCC TCG|GAG CAC CAC AAC CAG CCG CTC TGG CTG ACC CAC TTG CAA   1392
ILE ALA SER|GLU HIS HIS ASN GLN PRO LEU TRP LEU THR HIS LEU GLN
    450             455             460
```

```
GAC ATC|GCC AAT CGA GTG CTG CTG TCA CTC TTC ACC ATC GAG ATG CTG   1440
ASP ILE|ALA ASN ARG VAL LEU LEU SER LEU PHE THR ILE GLU MET LEU
465    |    470             475             480
```

```
CTG AAG ATG TAC GGG CTG|GGC CTG CGC CAG TAC TTC ATG TCC|ATC TTC   1488
LEU LYS MET TYR GLY LEU|GLY LEU ARG GLN TYR PHE MET SER|ILE PHE
            485             490                         495
```

```
AAC CGC TTC GAC TGC TTC GTG GTG TGC AGC GGC ATC CTG GAG CTG CTG   1536
ASN ARG PHE ASP CYS PHE VAL VAL CYS SER GLY ILE LEU GLU LEU LEU
        500             505             510
```

```
CTG|GTG GAG TCG GGC GCC ATG ACG CCG CTG GGC|ATC TCC GTG TTG CGC   1584
LEU|VAL GLU SER GLY ALA MET THR PRO LEU GLY|ILE SER VAL LEU ARG
   |    515             520                |    525
```

```
TGC ATC CGC CTC CTG AGG CTC TTC AAG ATC ACC AAG TAC TGG|ACG TCG   1632
CYS ILE ARG LEU LEU ARG LEU PHE LYS ILE THR LYS TYR TRP|THR SER
    530             535             540
```

FIGURE 1d

```
CTC AGC AAC CTG GTG GCC TCC CTG CTC AAC TCC ATC CGC TCC ATC GCC 1680
LEU SER ASN LEU VAL ALA SER LEU LEU ASN SER ILE ARG SER ILE ALA
545                 550                 555                 560

TCG CTG CTG CTG CTG CTC TTC CTC TTC ATC ATC ATC TTC GCC CTG CTG 1728
SER LEU LEU LEU LEU LEU PHE LEU PHE ILE ILE ILE PHE ALA LEU LEU
                565                 570                 575

GGC ATG CAG CTC TTC GGG GGG CGG TAC GAC TTC GAG GAC ACG GAA GTG 1766
GLY MET GLN LEU PHE GLY GLY ARG TYR ASP PHE GLU ASP THR GLU VAL
            580                 585                 590

CGA CGC AGC AAC TTC GAC AAC TTC CCC CAG GCC CTC ATC AGC GTC TTC 1824
ARG ARG SER ASN PHE ASP ASN PHE PRO GLN ALA LEU ILE SER VAL PHE
        595                 600                 605

CAG GTG CTG ACG GGT GAG GAC TGG AAC TCC GTG ATG TAC AAC GGG ATC 1872
GLN VAL LEU THR GLY GLU ASP TRP ASN SER VAL MET TYR ASN GLY ILE
    610                 615                 620

ATG GCC TAC GGA GGC CCG TCC TAC CCG GGC GTT CTC GTG TGC ATC TAT 1920
MET ALA TYR GLY GLY PRO SER TYR PRO GLY VAL LEU VAL CYS ILE TYR
625                 630                 635                 640

TTC ATC ATC CTT TTT GTC TGC GGC AAC TAT ATC CTG CTG AAT GTC TTC 1968
PHE ILE ILE LEU PHE VAL CYS GLY ASN TYR ILE LEU LEU ASN VAL PHE
                645                 650                 655

CTG GCC ATC GCC GTG GAC AAC CTG GCC GAG GCC GAG AGC CTG ACT TCC 2016
LEU ALA ILE ALA VAL ASP ASN LEU ALA GLU ALA GLU SER LEU THR SER
                660                 665                 670

GCG CAA AAG GCC AAG GCC GAG GAG AGG AAA CGT AGG AAG ATG TCC AGG 2064
ALA GLN LYS ALA LYS ALA GLU GLU ARG LYS ARG ARG LYS MET SER ARG
            675                 680                 685    P

GGT CTC CCT GAC AAG ACG GAG GAG GAG AAG TCT GTG ATG GCC AAG AAG 2112
GLY LEU PRO ASP LYS THR GLU GLU GLU LYS SER VAL MET ALA LYS LYS
        690                 695                 700

CTG GAG CAG AAG CCC AAG GGG GAG GGC ATC CCC ACC ACT GCC AAG CTC 2160
LEU GLU GLN LYS PRO LYS GLY GLU GLY ILE PRO THR THR ALA LYS LEU
705                 710                 715                 720

AAG GTC GAT GAG TTC GAA TCT AAC GTC AAC GAG GTG AAG GAC CCC TAC 2208
LYS VAL ASP GLU PHE GLU SER ASN VAL ASN GLU VAL LYS ASP PRO TYR
                725                 730                 735
```

FIGURE 1e

```
CCT TCA GCT GAC TTC CCA GGG GAT GAT GAG GAG GAC GAG CCT GAG ATC 2256
PRO SER ALA ASP PHE PRO GLY ASP ASP GLU GLU ASP GLU PRO GLU ILE
         740             745                 750

CCA GTG AGC CCC CGA CCG CGC CCG CTG GCC GAG CTG CAG CTC AAA GAG 2304
PRO VAL SER PRO ARG PRO ARG PRO LEU ALA GLU LEU GLN LEU LYS GLU
         755             760                 765

AAG GCA GTG CCC ATC CCG GAA GCC AGC TCC TTC TTC ATC TTC AGT CCC 2352
LYS ALA VAL PRO ILE PRO GLU ALA SER SER PHE PHE ILE PHE SER PRO
    770             775                 780

ACC AAT AAG GTC CGT GTC CTG TGT CAC CGC ATC GTC AAC GCC ACC TGG 2400
THR ASN LYS VAL ARG VAL LEU CYS HIS ARG ILE VAL ASN ALA THR TRP
785             790                 795   *                 800

TTC ACC AAC TTC ATC CTG CTC TTC ATC CTG CTC AGC AGT GCT GCG CTG 2448
PHE THR ASN PHE ILE LEU LEU PHE ILE LEU LEU SER SER ALA ALA LEU
             805                 810                 815

GCC GCC GAG GAC CCC ATC CGG GCG GAG TCC GTG AGG AAT CAG ATC CTT 2496
ALA ALA GLU ASP PRO ILE ARG ALA GLU SER VAL ARG ASN GLN ILE LEU
         820                 825                 830

GGA TAT TTT GAT ATT GCC TTC ACC TCT GTC TTC ACT GTG GAG ATT GTC 2544
GLY TYR PHE ASP ILE ALA PHE THR SER VAL PHE THR VAL GLU ILE VAL
         835             840                 845

CTC AAG ATG ACA ACC TAC GGC GCC TTC CTG CAC AAG GGC TCC TTC TGC 2592
LEU LYS MET THR THR TYR GLY ALA PHE LEU HIS LYS GLY SER PHE CYS
        850                 855                 860

CGC AAC TAC TTC AAC ATC CTG GAC CTG CTG GTG GTG GCC GTG TCT CTC 2640
ARG ASN TYR PHE ASN ILE LEU ASP LEU LEU VAL VAL ALA VAL SER LEU
865             870                 875                 880

ATC TCC ATG GGT CTC GAG TCC AGC ACC ATC TCC GTG GTA AAG ATC CTG 2688
ILE SER MET GLY LEU GLU SER SER THR ILE SER VAL VAL LYS ILE LEU
            885                 890                 895

AGA GTG CTA AGG GTG CTC CGG CCC CTG CGA GCC ATC AAC AGA GCC AAA 2736
ARG VAL LEU ARG VAL LEU ARG PRO LEU ARG ALA ILE ASN ARG ALA LYS
        900                 905                 910
```

FIGURE 1f

```
GGG TTG AAG CAC GTG GTC CAG TGC GTG TTC GTG GCC ATC CGC ACC ATC  2784
GLY LEU LYS HIS VAL VAL GLN CYS VAL PHE VAL ALA ILE ARG THR ILE
        915             920             925

GGG AAC|ATC GTC CTG GTC ACC ACG CTC CTG CAG TTC ATG TTC GCC TGC  2832
GLY ASN|ILE VAL LEU VAL THR THR LEU LEU GLN PHE MET PHE ALA CYS
    930             935             940

ATC GGT GTC CAG CTC TTC|AAG GGC AAG TTC TTC AGC TGC AAT GAC CTA  2880
ILE GLY VAL GLN LEU PHE|LYS GLY LYS PHE PHE SER CYS ASN ASP LEU
945             950             955             960

TCC AAG ATG ACA GAA GAG GAG TGC AGG GGC TAC TAC TAT GTG TAC AAG  2928
SER LYS MET THR GLU GLU GLU CYS ARG GLY TYR TYR TYR VAL TYR LYS
            965             970             975

GAC GGG GAC CCC ACG CAG ATG GAG CTG CGC CCC GCG CAG TGG ATA CAC  2976
ASP GLY ASP PRO THR GLN MET GLU LEU ARG PRO ARG GLN TRP ILE HIS
            980             985             990

AAT GAC TTC CAC TTT GAC AAC GTG CTG TCG GCC ATG ATG TCG CTC TTC  3024
ASN ASP PHE HIS PHE ASP ASN VAL LEU SER ALA MET MET SER LEU PHE
        995             1000            1005

ACG GTG TCC ACC TTC GAG GGA TGG CCC CAG CTG CTG TAC AGG GCC ATA  3072
THR VAL SER THR PHE GLU GLY TRP PRO GLN LEU LEU TYR ARG ALA ILE
        1010            1015            1020

GAC TCC AAC GAG GAG GAC ATG GGC CCC GTT TAC AAC AAC CGA GTG GAG  3120
ASP SER ASN GLU GLU ASP MET GLY PRO VAL TYR ASN ASN ARG VAL GLU
1025            1030            1035            1040

|ATG GCC ATC TTC TTC ATC ATC TAC ATC ATC CTC ATT GCC TTC TTC ATG  3168
|MET ALA ILE PHE PHE ILE ILE TYR ILE ILE LEU ILE ALA PHE PHE MET
        1045            1050            1055

ATG AAC ATC TTT GTG GGC TTT GTC ATC|GTC ACC TTC CAG GAG CAG GGG  3216
MET ASN ILE PHE VAL GLY PHE VAL ILE|VAL THR PHE GLN GLU GLN GLY
        1060            1065            1070

GAG ACG GAG TAC AAG AAC TGC GAG CTG GAC AAG AAC CAG CGC CAG TGT  3264
GLU THR GLU TYR LYS ASN CYS GLU LEU ASP LYS ASN GLN ARG GLN CYS
        1075            1080            1085

GTG CAG TAT GCC CTG AAG GCC CGC CCA CTT CGG TGC TAC ATC CCC AAG  3312
VAL GLN TYR ALA LEU LYS ALA ARG PRO LEU ARG CYS TYR ILE PRO LYS
        1090            1095            1100
```

FIGURE 1g

```
AAC CCA TAC CAG TAC CAG GTG TGG TAC GTC GTC ACC TCC TCC TAC TTT  3360
ASN PRO TYR GLN TYR GLN VAL TRP TYR VAL VAL THR SER SER TYR PHE
1105                1110                1115                1120

GAA TAC CTG ATG TTC GCC CTC ATC ATG CTC AAC ACC ATC TGC CTG GGC  3408
GLU TYR LEU MET PHE ALA LEU ILE MET LEU ASN THR ILE CYS LEU GLY
                1125                1130                1135

ATG CAG CAC TAC CAC CAG TCG GAG GAG ATG AAC CAC ATC TCA GAC ATC  3456
MET GLN HIS TYR HIS GLN SER GLU GLU MET ASN HIS ILE SER ASP ILE
                    1140                1145                1150

CTC AAT GTG GCC TTC ACC ATC ATC TTC ACG CTG GAG ATG ATT CTC AAG  3504
LEU ASN VAL ALA PHE THR ILE ILE PHE THR LEU GLU MET ILE LEU LYS
            1155                1160                1165

CTC TTG GCG TTC AAG GCC AGG GGC TAT TTC GGA GAC CCC TGG AAT GTG  3552
LEU LEU ALA PHE LYS ALA ARG GLY TYR PHE GLY ASP PRO TRP ASN VAL
        1170                1175                1180

TTC GAC TTC CTG ATC GTC ATC GGC AGC ATC ATT GAC GTC ATC CTC AGC  3600
PHE ASP PHE LEU ILE VAL ILE GLY SER ILE ILE ASP VAL ILE LEU SER
1185                1190                1195                1200

GAG ATC GAC ACT TTC CTG GCC TCC AGC GGG GGA CTG TAT TGC CTG GGT  3648
GLU ILE ASP THR PHE LEU ALA SER SER GLY GLY LEU TYR CYS LEU GLY
                1205                1210                1215

GGC GGC TGC GGG AAC GTT GAC CCA GAC GAG AGC GCC CGC ATC TCC AGT  3696
GLY GLY CYS GLY ASN VAL ASP PRO ASP GLU SER ALA ARG ILE SER SER
                1220                1225                1230

GCC TTC TTC CGC CTG TTC CGG GTT ATG AGG CTG ATC AAG CTG CTG AGT  3744
ALA PHE PHE ARG LEU PHE ARG VAL MET ARG LEU ILE LYS LEU LEU SER
            1235                1240                1245

CGG GCC GAG GGC GTG CGC ACG CTG CTG TGG ACG TTC ATC AAG TCC TTC  3792
ARG ALA GLU GLY VAL ARG THR LEU LEU TRP THR PHE ILE LYS SER PHE
        1250                1255                1260

CAG GCC CTG CCC TAC GTG GCC CTG CTC ATC GTC ATG CTG TTC TTC ATC  3840
GLN ALA LEU PRO TYR VAL ALA LEU LEU ILE VAL MET LEU PHE PHE ILE
            1265                1270                1275                1280
```

FIGURE 1h

```
TAC GCC GTC ATC GGC ATG CAG ATG TTT GGA AAG ATC GCC CTG GTG GAC  3888
TYR ALA VAL ILE GLY MET GLN MET PHE GLY LYS ILE ALA LEU VAL ASP
            1285                1290            1295

GGG ACC CAG ATC AAC CGC AAC AAC AAC TTC CAG ACC TTC CCG CAG GCC  3936
GLY THR GLN ILE ASN ARG ASN ASN ASN PHE GLN THR PHE PRO GLN ALA
            1300                1305            1310

GTG CTG CTG CTC TTC AGG TGT GCG ACA GGG GAG GCG TGG CAA GAG ATC  3984
VAL LEU LEU LEU PHE ARG CYS ALA THR GLY GLU ALA TRP GLN GLU ILE
            1315                1320            1325

CTG CTG GCC TGC AGC TAC GGG AAG TTG TGC GAC CCA GAG TCA GAC TAC  4032
LEU LEU ALA CYS SER TYR GLY LYS LEU CYS ASP PRO GLU SER ASP TYR
            1330                1335            1340

GCC CCG GGC GAG GAG TAC ACG TGT GGC ACC AAC TTC GCC TAC TAC TAC  4080
ALA PRO GLY GLU GLU TYR THR CYS GLY THR ASN PHE ALA TYR TYR TYR
1345                1350                1355                1360

TTC ATC AGC TTC TAC ATG CTC TGC GCC TTC CTG ATC ATC AAC CTC TTC  4128
PHE ILE SER PHE TYR MET LEU CYS ALA PHE LEU ILE ILE ASN LEU PHE
            1365                1370            1375

GTG GCT GTC ATC ATG GAC AAC TTT GAC TAC CTG ACA CGC GAC TGG TCC  4176
VAL ALA VAL ILE MET ASP ASN PHE ASP TYR LEU THR ARG ASP TRP SER
            1380                1385            1390

ATC CTG GGC CCT CAC CAC CTG GAC GAG TTC AAG GCC ATC TGG GCA GAG  4224
ILE LEU GLY PRO HIS HIS LEU ASP GLU PHE LYS ALA ILE TRP ALA GLU
            1395                1400            1405

TAT GAC CCA GAG GCC AAG GGG CGA ATC AAG CAC CTG GAC GTG GTG ACC  4272
TYR ASP PRO GLU ALA LYS GLY ARG ILE LYS HIS LEU ASP VAL VAL THR
    1410                1415            1420

CTG CTG AGA AGG ATC CAG CCC CCT CTG GGC TTC GGG AAG TTC TGT CCA  4320
LEU LEU ARG ARG ILE GLN PRO PRO LEU GLY PHE GLY LYS PHE CYS PRO
1425                1430                1435                1440

CAC CGG GTG GCC TGT AAG CGC CTG GTG GGC ATG AAC ATG CCC CTG AAC  4368
HIS ARG VAL ALA CYS LYS ARG LEU VAL GLY MET ASN MET PRO LEU ASN
            1445                1450            1455

AGT GAC GGC ACG GTC ACC TTC AAT GCC ACG CTC TTT GCC CTG GTG CGC  4416
SER ASP GLY THR VAL THR PHE ASN ALA THR LEU PHE ALA LEU VAL ARG
            1460             *  1465            1470

ACG GCC CTC AAG ATC AAG ACA GAA GGT AAC TTC GAG CAG GCC AAC GAG  4464
THR ALA LEU LYS ILE LYS THR GLU GLY ASN PHE GLU GLN ALA ASN GLU
            1475                1480            1485
```

FIGURE 1i

```
GAG CTG AGG GCC ATC ATC AAG AAG ATC TGG AAG AGA ACC AGC ATG AAG  4512
GLU LEU ARG ALA ILE ILE LYS LYS ILE TRP LYS ARG THR SER MET LYS
    1490                1495                1500      P

CTA CTG GAC CAG GTC ATC CCT CCC ATA GGA GAT GAC GAG GTG ACC GTG  4560
LEU LEU ASP GLN VAL ILE PRO PRO ILE GLY ASP ASP GLU VAL THR VAL
1505                1510                1515                1520

GGG AAG TTC TAC GCC ACA TTC CTC ATC CAG GAG CAC TTC CGG AAG TTC  4608
GLY LYS PHE TYR ALA THR PHE LEU ILE GLN GLU HIS PHE ARG LYS PHE
                1525                1530                1535

ATG AAG CGC CAG GAG GAA TAT TAT GGG TAT CGG CCC AAG AAG GAC ACC  4656
MET LYS ARG GLN GLU GLU TYR TYR GLY TYR ARG PRO LYS LYS ASP THR
            1540                1545                1550

GTG CAG ATC CAG GCT GGG CTG CGG ACC ATA GAG GAG GAG GCG GCC CCT  4704
VAL GLN ILE GLN ALA GLY LEU ARG THR ILE GLU GLU GLU ALA ALA PRO
        1555                1560                1565

GAG ATC CGC CGC ACC ATC TCA GGA GAC CTG ACC GCC GAG GAG GAG CTG  4752
GLU ILE ARG ARG THR ILE SER GLY ASP LEU THR ALA GLU GLU GLU LEU
    1570                1575                1580
                        P

GAG AGA GCC ATG GTG GAG GCT GCG ATG GAG GAG AGG ATC TTC CGG AGG  4800
GLU ARG ALA MET VAL GLU ALA ALA MET GLU GLU ARG ILE PHE ARG ARG
1585                1590                1595                1600

ACC GGA GGC CTG TTT GGC CAG GTG GAC ACC TTC CTG GAA AGG ACC AAC  4848
THR GLY GLY LEU PHE GLY GLN VAL ASP THR PHE LEU GLU ARG THR ASN
                1605                1610                1615

TCC CTA CCC CCG GTG ATG GCC AAC CAA AGA CCG CTC CAG TTT GCT GAG  4896
SER LEU PRO PRO VAL MET ALA ASN GLN ARG PRO LEU GLN PHE ALA GLU
            1620                1625                1630

ATA GAA ATG GAA GAG CTT GAG TCG CCT GTC TTC TTG GAG GAC TTC CCT  4944
ILE GLU MET GLU GLU LEU GLU SER PRO VAL PHE LEU GLU ASP PHE PRO
        1635                1640                1645

CAA GAC GCA AGA ACC AAC CCT CTC GCT CGT GCC AAT ACC AAC AAC GCC  4992
GLN ASP ALA ARG THR ASN PRO LEU ALA ARG ALA ASN THR ASN ASN ALA
    1650                1655                1660

AAT GCC AAT GTT GCC TAT GGC AAC AGC AAC CAT AGC AAC AAC CAG ATG  5040
ASN ALA ASN VAL ALA TYR GLY ASN SER ASN HIS SER ASN ASN GLN MET
1665                1670            *   1675                1680

TTT TCC AGC GTC CAC TGT GAA AGG GAG TTC CCG GGA GAG GCG GAG ACA  5088
PHE SER SER VAL HIS CYS GLU ARG GLU PHE PRO GLY GLU ALA GLU THR
                1685                1690                1695
```

FIGURE 1j

```
CCG GCT GCC GGA CGA GGA GCC CTC AGC CAC TCC CAC AGG GCC CTG GGA    5136
PRO ALA ALA GLY ARG GLY ALA LEU SER HIS SER HIS ARG ALA LEU GLY
        1700                1705                1710

CCT CAC AGC AAG CCC TGT GCT GGA AAA CTG AAT GGG CAG CTG GTC CAG    5184
PRO HIS SER LYS PRO CYS ALA GLY LYS LEU ASN GLY GLN LEU VAL GLN
        1715                1720                1725

CCG GGA ATG CCC ATC AAC CAG GCA CCT CCT GCC CCC TGC CAG CAG CCT    5232
PRO GLY MET PRO ILE ASN GLN ALA PRO PRO ALA PRO CYS GLN GLN PRO
        1730                1735                1740

AGC ACA GAT CCC CCA GAG CGC GGG CAG AGG AGG ACC TCC CTG ACA GGG    5280
SER THR ASP PRO PRO GLU ARG GLY GLN ARG ARG THR SER LEU THR GLY
1745                1750                1755   P            1760

TCT CTG CAA GAC GAA GCA CCC CAG AGG AGG AGC TCC GAG GGG AGC ACC    5328
SER LEU GLN ASP GLU ALA PRO GLN ARG ARG SER SER GLU GLY SER THR
                1765                1770  P            1775

CCC AGG CGC CCG GCT CCT GCT ACA GCT CTG CTG ATC CAA GAG GCT CTG    5376
PRO ARG ARG PRO ALA PRO ALA THR ALA LEU LEU ILE GLN GLU ALA LEU
        1780                1785                1790

GTT CGA GGG GGC CTG GAC ACC TTG GCA GCT GAT GCT GGC TTC GTC ATG    5424
VAL ARG GLY GLY LEU ASP THR LEU ALA ALA ASP ALA GLY PHE VAL MET
        1795                1800                1805

GCA ACA AGC CAG GCC CTG GTA GAC GCC TGT CAG ATG GAA CCG GAG GAA    5472
ALA THR SER GLN ALA LEU VAL ASP ALA CYS GLN MET GLU PRO GLU GLU
        1810                1815                1820

GTA GAG GTC GCA GCC ACA GAG CTA CTG AAA GAG CGA GAG TCC GTC CAG    5520
VAL GLU VAL ALA ALA THR GLU LEU LEU LYS GLU ARG GLU SER VAL GLN
1825                1830                1835                1840

GGC ATG GCC AGT GTC CCG GGA AGC CTG AGC CGC AGG TCC TCC CTG GGC    5568
GLY MET ALA SER VAL PRO GLY SER LEU SER ARG ARG SER SER LEU GLY
        1845                1850          P    1855

AGC CTT GAC CAG GTC CAG GGC TCC CAG GAA ACC CTT ATT CCT CCC AGG    5616
SER LEU ASP GLN VAL GLN GLY SER GLN GLU THR LEU ILE PRO PRO ARG
        1860                1865                1870

CCG TGA TGGCTGTGCA GTGTCCACAT GACCAAGGCG AGGGGACAG  TGCGTGCAGA    5672
PRO

AGCTCAGCCC TGCATGGCAG CCTCCCTCTG TCTCAGCCCT CCTGCTGAGC              5722
TGGGGCGGTC TGGAACCGAC CAGGAAGCCA GGAGCCTCCC CTGGCCAGCA              5772
AGAGGCATGA TTCTAAAGCA TCCAGAAAGG CCTGGTCAGT GCCACTCCCC              5822
AGCAGGACAT TAAAGTCTCT AGGTCTGTGG CAAAAAAAAA AAAAAAAAA               5872
AAAAAAAAAA AAAAAAAAAA AAAAA                                        5897
```

FIGURE 2a

```
5'                                                              AGAAGGGA  -301
GGGCGAGCGT GGTGTGTGCG CGCTCGGGCG CCGGCGGCAC CGCCGAGGTC TGTTGGCAAA  -241
AGTCGCCCTT GATGGCGGCG GAGGCGAGGC AGCCGCGGCG CCGAACAGCC GACGCGCGCT  -181
AGCGGGGTCC GCCCGCCCCT TTCCCAGAGC CCAGCGCCGC CGTTCGCCGC CGCCGCCGCC  -121
CGCCCGCGCG CCGTTCGCCG CCGCCGCCGC CCGCGGGTGG CAGCGCCGCT CGGTCCCCGG   -61
CCCCGGGGCC GGCTGGGGGG CGGTCGGGGC GTGTGAGGGG CTTGCTCCCA GCTCGCGAAG    -1
```

| ATG | GCT | GCG | GGC | CGC | CCG | CTG | GCC | TGG | ACG | CTG | ACA | CTT | TGG | CAG | GCG | 48 |
|---|---|---|---|---|---|---|---|---|---|---|---|---|---|---|---|---|
| MET | ALA | ALA | GLY | ARG | PRO | LEU | ALA | TRP | THR | LEU | THR | LEU | TRP | GLN | ALA | |
| | -25 | | | | -20 | | | | | -15 | | | | | | |

| TGG | CTG | ATC | CTG | ATC | GGG | CCC | TCG | TCG | GAG | GAG | CCG | TTC | CCT | TCA | GCC | 96 |
|---|---|---|---|---|---|---|---|---|---|---|---|---|---|---|---|---|
| TRP | LEU | ILE | LEU | ILE | GLY | PRO | SER | SER | GLU | GLU | PRO | PHE | PRO | SER | ALA | |
| -10 | | | | | -5 | | | | -1 | +1 | | | | 5 | | |

| GTC | ACT | ATC | AAG | TCA | TGG | GTG | GAT | AAG | ATG | CAA | GAA | GAC | CTG | GTC | ACA | 144 |
|---|---|---|---|---|---|---|---|---|---|---|---|---|---|---|---|---|
| VAL | THR | ILE | LYS | SER | TRP | VAL | ASP | LYS | MET | GLN | GLU | ASP | LEU | VAL | THR | |
| | | | 10 | | | | | 15 | | | | | 20 | | | |

| CTG | GCA | AAA | ACA | GCA | AGT | GGA | GTC | CAT | CAG | CTT | GTT | GAT | ATT | TAT | GAG | 192 |
|---|---|---|---|---|---|---|---|---|---|---|---|---|---|---|---|---|
| LEU | ALA | LYS | THR | ALA | SER | GLY | VAL | HIS | GLN | LEU | VAL | ASP | ILE | TYR | GLU | |
| | | 25 | | | | | 30 | | | | | | 35 | | | |

| AAA | TAT | CAA | GAT | TTG | TAT | ACT | GTG | GAA | CCA | AAT | AAT | GCA | CGT | CAG | CTG | 240 |
|---|---|---|---|---|---|---|---|---|---|---|---|---|---|---|---|---|
| LYS | TYR | GLN | ASP | LEU | TYR | THR | VAL | GLU | PRO | ASN | ASN | ALA | ARG | GLN | LEU | |
| | 40 | | | | | 45 | | | | | 50 | | | | | |

| GTG | GAA | ATT | GCA | GCC | AGA | GAC | ATT | GAG | AAG | CTT | CTC | AGC | AAC | AGA | TCT | 288 |
|---|---|---|---|---|---|---|---|---|---|---|---|---|---|---|---|---|
| VAL | GLU | ILE | ALA | ALA | ARG | ASP | ILE | GLU | LYS | LEU | LEU | SER | ASN | ARG | SER | |
| 55 | | | | | 60 | | | | 65 | | | | * | | 70 | |

| AAA | GCC | CTG | GTG | CGC | CTG | GCT | TTG | GAA | GCA | GAG | AAA | GTT | CAA | GCA | GCC | 336 |
|---|---|---|---|---|---|---|---|---|---|---|---|---|---|---|---|---|
| LYS | ALA | LEU | VAL | ARG | LEU | ALA | LEU | GLU | ALA | GLU | LYS | VAL | GLN | ALA | ALA | |
| | | | | 75 | | | | | 80 | | | | | 85 | | |

| CAC | CAA | TGG | AGG | GAA | GAT | TTT | GCA | AGC | AAT | GAA | GTT | GTC | TAC | TAT | AAC | 384 |
|---|---|---|---|---|---|---|---|---|---|---|---|---|---|---|---|---|
| HIS | GLN | TRP | ARG | GLU | ASP | PHE | ALA | SER | ASN | GLU | VAL | VAL | TYR | TYR | ASN | |
| | | | 90 | | | | | 95 | | | | | | 100 | | |

| GCG | AAG | GAT | GAT | CTT | GAT | CCT | GAA | AAA | AAT | GAC | AGT | GAA | CCA | GGC | AGC | 432 |
|---|---|---|---|---|---|---|---|---|---|---|---|---|---|---|---|---|
| ALA | LYS | ASP | ASP | LEU | ASP | PRO | GLU | LYS | ASN | ASP | SER | GLU | PRO | GLY | SER | |
| | | 105 | | | | | 110 | | * | | | | 115 | | | |

| CAG | AGG | ATC | AAA | CCT | GTT | TTC | ATT | GAC | GAT | GCT | AAC | TTT | AGA | AGA | CAA | 480 |
|---|---|---|---|---|---|---|---|---|---|---|---|---|---|---|---|---|
| GLN | ARG | ILE | LYS | PRO | VAL | PHE | ILE | ASP | ASP | ALA | ASN | PHE | ARG | ARG | GLN | |
| | | 120 | | | | | 125 | | | | | 130 | | | | |

| GTA | TCC | TAT | CAG | CAC | GCA | GCT | GTC | CAT | ATC | CCC | ACT | GAC | ATC | TAT | GAA | 528 |
|---|---|---|---|---|---|---|---|---|---|---|---|---|---|---|---|---|
| VAL | SER | TYR | GLN | HIS | ALA | ALA | VAL | HIS | ILE | PRO | THR | ASP | ILE | TYR | GLU | |
| 135 | | | | 140 | | | | 145 | | | | | | 150 | | |

FIGURE 2b

```
GGA TCG ACA ATC GTG TTA AAC GAA CTC AAC TGG ACA AGT GCC TTA GAT      576
GLY SER THR ILE VAL LEU ASN GLU LEU ASN TRP THR SER ALA LEU ASP
            155                 160                 165
                                 *

GAC GTT TTC AAA AAA AAT CGA GAG GAA GAC CCT TCA CTG TTG TGG CAG      624
ASP VAL PHE LYS LYS ASN ARG GLU GLU ASP PRO SER LEU LEU TRP GLN
            170                 175                 180

GTG TTT GGC AGT GCC ACT GGC CTG GCC CGG TAT TAC CCA GCT TCT CCA      672
VAL PHE GLY SER ALA THR GLY LEU ALA ARG TYR TYR PRO ALA SER PRO
            185                 190                 195

TGG GTT GAT AAT AGC CGA ACC CCA AAC AAG ATT GAT CTT TAT GAT GTA      720
TRP VAL ASP ASN SER ARG THR PRO ASN LYS ILE ASP LEU TYR ASP VAL
            200                 205                 210

CGC AGA AGA CCA TGG TAC ATC CAA GGT GCT GCA TCC CCT AAA GAT ATG      768
ARG ARG ARG PRO TRP TYR ILE GLN GLY ALA ALA SER PRO LYS ASP MET
215                 220                 225                 230

CTT ATT CTG GTG GAT GTG AGT GGA AGC GTT AGT GGA CTG ACA CTC AAA      816
LEU ILE LEU VAL ASP VAL SER GLY SER VAL SER GLY LEU THR LEU LYS
            235                 240                 245

CTC ATC CGG ACA TCC GTC TCC GAA ATG TTG GAA ACC CTC TCA GAT GAT      864
LEU ILE ARG THR SER VAL SER GLU MET LEU GLU THR LEU SER ASP ASP
            250                 255                 260

GAT TTT GTG AAC GTG GCT TCA TTT AAC AGC AAT GCT CAG GAT GTA AGC      912
ASP PHE VAL ASN VAL ALA SER PHE ASN SER ASN ALA GLN ASP VAL SER
            265                 270                 275

TGC TTT CAG CAC CTT GTC CAA GCA AAT GTA AGA AAT AAG AAA GTG TTG      960
CYS PHE GLN HIS LEU VAL GLN ALA ASN VAL ARG ASN LYS LYS VAL LEU
            280                 285                 290

AAA GAT GCA GTG AAT AAT ATC ACA GCA AAA GGA ATC ACA GAT TAT AAG     1008
LYS ASP ALA VAL ASN ASN ILE THR ALA LYS GLY ILE THR ASP TYR LYS
295                 300                 305                 310
                     *

AAG GGC TTT AGT TTT GCT TTT GAG CAG CTG CTT AAT TAT AAT GTA TCC     1056
LYS GLY PHE SER PHE ALA PHE GLU GLN LEU LEU ASN TYR ASN VAL SER
            315                 320                  *  325

AGA GCC AAC TGC AAT AAG ATT ATC ATG TTG TTC ACG GAC GGA GGA GAA     1104
ARG ALA ASN CYS ASN LYS ILE ILE MET LEU PHE THR ASP GLY GLY GLU
            330                 335                 340
```

FIGURE 2c

| | | | | | | | | | | | | | | | | |
|---|---|---|---|---|---|---|---|---|---|---|---|---|---|---|---|---|
| GAG | AGA | GCC | CAG | GAG | ATA | TTT | GCC | AAA | TAC | AAT | AAA | GAC | AAG | AAA | GTA | 1152 |
| GLU | ARG | ALA | GLN | GLU | ILE | PHE | ALA | LYS | TYR | ASN | LYS | ASP | LYS | LYS | VAL | |
| | | 345 | | | | 350 | | | | | | 355 | | | | |

| | | | | | | | | | | | | | | |
|---|---|---|---|---|---|---|---|---|---|---|---|---|---|---|
| CGT | GTA | TTC | ACA | TTC | TCA | GTT | GGC | CAA | CAT | AAT | TAC | GAC | AGA | GGA | CCT | 1200 |
| ARG | VAL | PHE | THR | PHE | SER | VAL | GLY | GLN | HIS | ASN | TYR | ASP | ARG | GLY | PRO | |
| | | 360 | | | | 365 | | | | | 370 | | | | | |

| ATT | CAG | TGG | ATG | GCT | TGC | GAA | AAT | AAA | GGT | TAT | TAT | TAT | GAA | ATT | CCA | 1248 |
|---|---|---|---|---|---|---|---|---|---|---|---|---|---|---|---|---|
| ILE | GLN | TRP | MET | ALA | CYS | GLU | ASN | LYS | GLY | TYR | TYR | TYR | GLU | ILE | PRO | |
| 375 | | | | | 380 | | | | | 385 | | | | | 390 | |

| TCC | ATT | GGA | GCC | ATA | AGA | ATT | AAT | ACT | CAG | GAA | TAC | CTA | GAT | GTT | CTG | 1296 |
|---|---|---|---|---|---|---|---|---|---|---|---|---|---|---|---|---|
| SER | ILE | GLY | ALA | ILE | ARG | ILE | ASN | THR | GLN | GLU | TYR | LEU | ASP | VAL | LEU | |
| | | | | | 395 | | | | 400 | | | | | 405 | | |

| GGA | AGA | CCG | ATG | GTT | TTA | GCA | GGA | GAC | AAA | GCT | AAG | CAA | GTC | CAA | TGG | 1344 |
|---|---|---|---|---|---|---|---|---|---|---|---|---|---|---|---|---|
| GLY | ARG | PRO | MET | VAL | LEU | ALA | GLY | ASP | LYS | ALA | LYS | GLN | VAL | GLN | TRP | |
| | | | 410 | | | | | 415 | | | | | 420 | | | |

| ACA | AAT | GTG | TAC | CTG | GAT | GCA | CTG | GAA | CTG | GGA | CTT | GTC | ATT | ACT | GGA | 1392 |
|---|---|---|---|---|---|---|---|---|---|---|---|---|---|---|---|---|
| THR | ASN | VAL | TYR | LEU | ASP | ALA | LEU | GLU | LEU | GLY | LEU | VAL | ILE | THR | GLY | |
| | | 425 | | | | | 430 | | | | | 435 | | | | |

| ACT | CTT | CCG | GTC | TTC | AAC | ATA | ACT | GGC | CAA | TTT | GAA | AAT | AAG | ACA | AAC | 1440 |
|---|---|---|---|---|---|---|---|---|---|---|---|---|---|---|---|---|
| THR | LEU | PRO | VAL | PHE | ASN | ILE | THR | GLY | GLN | PHE | GLU | ASN | LYS | THR | ASN | |
| | 440 | | | | * | 445 | | | | | 450 | * | | | | |

| TTA | AAG | AAC | CAG | CTG | ATT | CTT | GGA | GTG | ATG | GGA | GTT | GAT | GTG | TCT | TTG | 1488 |
|---|---|---|---|---|---|---|---|---|---|---|---|---|---|---|---|---|
| LEU | LYS | ASN | GLN | LEU | ILE | LEU | GLY | VAL | MET | GLY | VAL | ASP | VAL | SER | LEU | |
| 455 | | | | | 460 | | | | | 465 | | | | | 470 | |

| GAA | GAT | ATT | AAA | AGA | CTG | ACA | CCA | CGT | TTT | ACA | CTC | TGC | CCC | AAT | GGC | 1536 |
|---|---|---|---|---|---|---|---|---|---|---|---|---|---|---|---|---|
| GLU | ASP | ILE | LYS | ARG | LEU | THR | PRO | ARG | PHE | THR | LEU | CYS | PRO | ASN | GLY | |
| | | | | 475 | | | | | 480 | | | | | 485 | | |

| TAC | TAT | TTT | GCA | ATT | GAT | CCT | AAT | GGT | TAT | GTG | TTA | TTA | CAT | CCA | AAT | 1584 |
|---|---|---|---|---|---|---|---|---|---|---|---|---|---|---|---|---|
| TYR | TYR | PHE | ALA | ILE | ASP | PRO | ASN | GLY | TYR | VAL | LEU | LEU | HIS | PRO | ASN | |
| | | | 490 | | | | | 495 | | | | | 500 | | | |

| CTT | CAG | CCA | AAG | CCT | ATT | GGT | GTA | GGT | ATA | CCA | ACA | ATT | AAT | TTG | AGA | 1632 |
|---|---|---|---|---|---|---|---|---|---|---|---|---|---|---|---|---|
| LEU | GLN | PRO | LYS | PRO | ILE | GLY | VAL | GLY | ILE | PRO | THR | ILE | ASN | LEU | ARG | |
| | | | 505 | | | | | 510 | | | | | 515 | | | |

| AAA | AGG | AGA | CCC | AAT | GTT | CAG | AAC | CCC | AAA | TCT | CAG | GAG | CCA | GTG | ACA | 1680 |
|---|---|---|---|---|---|---|---|---|---|---|---|---|---|---|---|---|
| LYS | ARG | ARG | PRO | ASN | VAL | GLN | ASN | PRO | LYS | SER | GLN | GLU | PRO | VAL | THR | |
| | | | 520 | | | | | 525 | | | | | 530 | | | |

| TTG | GAT | TTC | CTC | GAT | GCA | GAG | TTG | GAG | AAT | GAC | ATT | AAA | GTG | GAG | ATT | 1728 |
|---|---|---|---|---|---|---|---|---|---|---|---|---|---|---|---|---|
| LEU | ASP | PHE | LEU | ASP | ALA | GLU | LEU | GLU | ASN | ASP | ILE | LYS | VAL | GLU | ILE | |
| 535 | | | | | 540 | | | | | 545 | | | | | 550 | |

FIGURE 2d

```
CGA AAT AAA ATG ATC GAT GGA GAA AGT GGA GAA AAA ACA TTC AGA ACT    1766
ARG ASN LYS MET ILE ASP GLY GLU SER GLY GLU LYS THR PHE ARG THR
            555                 560                 565

CTG GTT AAA TCT CAA GAT GAG AGA TAT ATT GAC AAA GGA AAC AGG ACA    1824
LEU VAL LYS SER GLN ASP GLU ARG TYR ILE ASP LYS GLY ASN ARG THR
        570                 575                  *
                                                580

TAC ACG TGG ACT CCT GTC AAC GGC ACA GAT TAT AGC AGT TTG GCC TTG    1872
TYR THR TRP THR PRO VAL ASN GLY THR ASP TYR SER SER LEU ALA LEU
        585              *  590                 595

GTA TTA CCA ACC TAC AGT TTT TAC TAT ATA AAA GCC AAA ATA GAA GAG    1920
VAL LEU PRO THR TYR SER PHE TYR TYR ILE LYS ALA LYS ILE GLU GLU
        600                 605                 610

ACA ATA ACT CAG GCC AGA TAT TCA GAA ACA CTG AAA CCG GAT AAT TTT    1968
THR ILE THR GLN ALA ARG TYR SER GLU THR LEU LYS PRO ASP ASN PHE
615                 620                 625                 630

GAA GAA TCT GGC TAC ACA TTC CTA GCA CCA AGA GAT TAC TGC AGT GAC    2016
GLU GLU SER GLY TYR THR PHE LEU ALA PRO ARG ASP TYR CYS SER ASP
            635                 640                 645

CTT AAA CCT TCA GAT AAT AAC ACT GAA TTT CTT TTA AAT TTC AAT GAG    2064
LEU LYS PRO SER ASP ASN ASN THR GLU PHE LEU LEU ASN PHE ASN GLU
        650                 655                 660

TTT ATT GAT AGA AAA ACT CCA AAC AAC CCA TCC TGT AAT ACA GAC TTG    2112
PHE ILE ASP ARG LYS THR PRO ASN ASN PRO SER CYS ASN THR ASP LEU
        665                 670                 675

ATT AAT AGA GTC TTG CTG GAT GCA GGC TTT ACA AAT GAA CTT GTT CAA    2160
ILE ASN ARG VAL LEU LEU ASP ALA GLY PHE THR ASN GLU LEU VAL GLN
        680                 685                 690

AAT TAC TGG AGT AAG CAG AAG AAT ATC AAG GGA GTG AAA GCA CGG TTT    2208
ASN TYR TRP SER LYS GLN LYS ASN ILE LYS GLY VAL LYS ALA ARG PHE
695                 700                 705                 710

GTT GTG ACT GAT GGT GGG ATT ACC AGA GTT TAT CCC AAA GAG GCT GGA    2256
VAL VAL THR ASP GLY GLY ILE THR ARG VAL TYR PRO LYS GLU ALA GLY
                715                 720                 725

GAA AAT TGG CAG GAA AAC CCA GAG ACA TAT GAA GAC AGC TTC TAT AAA    2304
GLU ASN TRP GLN GLU ASN PRO GLU THR TYR GLU ASP SER PHE TYR LYS
            730                 735                 740

AGG AGC CTC GAT AAT GAT AAC TAC GTT TTC ACT GCT CCC TAC TTT AAC    2352
ARG SER LEU ASP ASN ASP ASN TYR VAL PHE THR ALA PRO TYR PHE ASN
        745                 750                 755          *
```

FIGURE 2e

```
AAA AGT GGA CCT GGG GCC TAT GAG TCA GGC ATT ATG GTA AGC AAA GCT   2400
LYS SER GLY PRO GLY ALA TYR GLU SER GLY ILE MET VAL SER LYS ALA
    760             765                 770

GTA GAA ATA TAT ATC CAA GGA AAA CTT CTT AAA CCT GCA GTT GTT GGA   2448
VAL GLU ILE TYR ILE GLN GLY LYS LEU LEU LYS PRO ALA VAL VAL GLY
775             780                 785                     790

ATT AAA ATT GAT GTA AAT TCT TGG ATA GAG AAT TTC ACC AAA ACT TCA   2496
ILE LYS ILE ASP VAL ASN SER TRP ILE GLU ASN PHE THR LYS THR SER
                795                 800  *              805

ATC AGG GAT CCG TGT GCT GGT CCA GTT TGT GAC TGC AAA CGA AAC AGT   2544
ILE ARG ASP PRO CYS ALA GLY PRO VAL CYS ASP CYS LYS ARG ASN SER
            810                 815                 820      P

GAT GTA ATG GAT TGT GTG ATT CTA GAT GAC GGT GGG TTT CTT TTG ATG   2592
ASP VAL MET ASP CYS VAL ILE LEU ASP ASP GLY GLY PHE LEU LEU MET
        825                 830                 835

GCC AAC CAT GAT GAT TAT ACC AAT CAG ATT GGA AGA TTC TTT GGA GAG   2640
ALA ASN HIS ASP ASP TYR THR ASN GLN ILE GLY ARG PHE PHE GLY GLU
    840                 845                 850

ATT GAT CCA AGC TTG ATG AGA CAC CTG GTC AAT ATA TCA GTT TAT GCC   2688
ILE ASP PRO SER LEU MET ARG HIS LEU VAL ASN ILE SER VAL TYR ALA
855             860                 865                     870
                                         *

TTT AAC AAA TCT TAT GAT TAT CAG TCG GTG TGT GAA CCT GGT GCT GCG   2736
PHE ASN LYS SER TYR ASP TYR GLN SER VAL CYS GLU PRO GLY ALA ALA
     *          875                 880                 885

CCA AAG CAG GGA GCA GGG CAC CGC|TCG GCT TAT GTG CCA TCA ATA GCA   2784
PRO LYS GLN GLY ALA GLY HIS ARG|SER ALA TYR VAL PRO SER ILE ALA
            890                 895                 900

GAC ATA CTG CAG ATT GGA TGG TGG GCC ACT GCT GCT GCC TGG TCT ATT   2832
ASP ILE LEU GLN ILE GLY TRP TRP ALA THR ALA ALA ALA TRP SER ILE
            905                 910                 915

CTT|CAG CAG TTT CTG TTG AGT TTG ACT TTT CCA CGG CTC CTT GAG GCA   2880
LEU|GLN GLN PHE LEU LEU SER LEU THR PHE PRO ARG LEU LEU GLU ALA
    920                 925                 930

GCT GAT ATG GAG GAT GAC GAC TTC ACT GCC TCC ATG TCA AAG CAG AGC   2928
ALA ASP MET GLU ASP ASP ASP PHE THR ALA SER MET SER LYS GLN SER
935             940                 945                 950
```

FIGURE 2f

```
TGC ATC ACT GAG CAA ACC CAG TAT TTC TTC GAT AAT GAC AGC AAA TCG   2976
CYS ILE THR GLU GLN THR GLN TYR PHE PHE ASP ASN ASP SER LYS SER
            955                 960  *              965

TTC AGT GGG GTA TTA GAC TGT GGG AAT TGT TCC AGA ATC TTT CAT GTA   3024
PHE SER GLY VAL LEU ASP CYS GLY ASN CYS SER ARG ILE PHE HIS VAL
            970                 975             980

GAA AAG CTC ATG AAC ACC AAT TTA ATA TTC ATA ATG GTA GAG AGC AAG   3072
GLU LYS LEU MET ASN THR ASN LEU ILE PHE ILE MET VAL GLU SER LYS
            985                 990             995

GGG ACA TGT CCC TGT GAC ACA CGG CTG CTC ATA CAA GCA GAG CAA ACT   3120
GLY THR CYS PRO CYS ASP THR ARG LEU LEU ILE GLN ALA GLU GLN THR
            1000                1005            1010

TCT GAT GGA CCA GAT CCT TGT GAT ATG GTT AAG CAA CCC AGA TAT CGA   3168
SER ASP GLY PRO ASP PRO CYS ASP MET VAL LYS GLN PRO ARG TYR ARG
1015                1020            1025            1030

AAA GGG CCA GAT GTC TGC TTT GAC AAC AAT GTC CTG GAG GAT TAT ACT   3218
LYS GLY PRO ASP VAL CYS PHE ASP ASN ASN VAL LEU GLU ASP TYR THR
                1035            1040            1045

GAC TGC GGT GGG GTC TCT GGA TTA AAT|CCT TCC CTG TGG TCC ATC ATC   3264
ASP CYS GLY GLY VAL SER GLY LEU ASN|PRO SER LEU TRP SER ILE ILE
                1050            1055            1060
                                 *

GGG ATA CAG TTT GTA CTG CTT TGG CTG GTT TCT GGC AGC|AGA CAC TGC  3312
GLY ILE GLN PHE VAL LEU LEU TRP LEU VAL SER GLY SER|ARG HIS CYS
            1065            1070            1075

CTG TTA TGA CCTTCTAAAA CCAAATCTCC ATAATTAAAC TCCAGACCCT          3361
LEU LEU
        1080

GCCACAACAT GATCCCTCCG TTATGTTAAA GTAGGGTCAA CTGTTAAATC            3411
AGAACATTAG CTGGGCCTCT GCCATGGCAG AGCCCTAAGG CGCAGACTCA            3461
TCAGGCACCC ACTGGCTGCA TGTCAGGGTG TCC ...... 3'                    3494
```

FIGURE 3a

```
           Human Neuronalα2
          .........................GGGCGGGGGAGGGGGATTGATCTTC    25
Rabbit Skeletal Muscleα2   |||||  |  ||||||    |      |
          CCCGGGGCCGGCTGGGGGGCGGTCGGGGCGTGTGAGGGGCTTGCTCCCAG   299
                  Start
          GATCGCAAGATGGCTGCTGGCTGCCTGCTGGCCTTGACTCTGACACTTTT    75
          ||||||||||||  |||  |||  ||||||||  |||  |||||||||||
          CTCGCGAAGATGGCTGCGGGCCGCCCGCTGGCCTGGACGCTGACACTTTG   349

CCAATCTT......TGCTCATCGGCCCCTCGTCGGAGGAGCCGTTCCCTT   119
          ||  | |       |  ||  ||||||  ||||||||||||||||||||
          Gcaggcgtggctgatcctgatcgggccctcgtcggaggagccgttccctt   399

CGGCCGTCACTATCAAATCATGGGTGGATAAGATGCAAGAAGACCTTGTC   169
          |  |||||||||||||  ||||||||||||||||||||||||||||  |||
          cagccgtcactatcaagtcatgggtggataagatgcaagaagacctggtc   449

ACACTGGCAAAAACAGCAAGTGGAGTCAATCAGCTTGTTGATATTTATGA   219
          ||||||||||||||||||||||||||||||||||||||||||||||||||
          acactggcaaaaacagcaagtggagtcaatcagcttgttgatatttatga   499

GAAATATCAAGATTTGTATACTGTGGAACCAAATAATGCACGCCAGCTGG   269
          ||||||||||||||||||||||||||||||||||||||||||| ||||||
          gaaatatcaagatttgtatactgtggaaccaaataatgcacgtcagctgg   549

TAGAAATTGCAGCCAGGGATATTGAGAAACTTCTGAGCAACAGATCTAAA   319
          |  ||||||||||||||  ||  ||||||||||  |||||  ||||||||||||||
          tggaaattgcagccagagacattgagaagcttctcagcaACAGATCTAAA   599

GCCCTGGTGAGCCTGGCATTGGAAGCGGAGAAAGTTCAAGCAGCTCACCA   369
          |||||||||  ||||||| |||||||  |||||||||||||||||  |||||
          GCCCTGGTGCGCCTGGCTTTGGAAGCAGAGAAAGTTCAAGCAGCCCACCA   649
```

FIGURE 3b

```
GTGGAGAGAAGATTTTGCAAGCAATGAAGTTGTCTACTACAATGCAAAGG  419
|||||  |||||||||||||||||||||||||||||||||  || || ||||
ATGGAGGGAAGATTTTGCAAGCAATGAAGTTGTCTACTATAACGCGAAGG  699

ATGATCTCGATCCTGAGAAAAATGACAGTGAGCCAGGCAGCCAGAGGATA  469
|||||||  ||||||||  ||||||||||||| |||||||||||||||||
ATGATCTTGATCCTGAAAAAAATGACAGTGAACCAGGCAGCCAGAGGATC  749

AAACCTGTTTTCATTGAAGATGCTAATTTTGGACGACAAATATCTTATCA  519
||||||||||||||||| ||||||||||  || ||||| |||| |||||
AAACCTGTTTTCATTGACGATGCTAACTTTAGAAGACAAGTATCCTATCA  799

GCACGCAGCAGTCCATATTCCTACTGACATCTATGAGGGCTCAACAATTG  569
||||||||| ||||||||  |||||||||||||||| || || ||||| |
GCACGCAGCTGTCCATATCCCCACTGACATCTATGAAGGATCGACAATCG  849

TGTTAAATGAACTCAACTGGACAAGTGCCTTAGATGAAGTTTTCAAAAAG  619
|||||| |||||||||||||||||||||||||||||| |||||||||||
TGTTAAACGAACTCAACTGGACAAGTGCCTTAGATGACGTTTTCAAAAAA  899

AATCGCGAGGAAGACCCTTCATTATTGTGGCAGGTTTTTGGCAGTGCCAC  669
||||| ||||||||||||||| | |||||||||||| |||||||||||||
AATCGAGAGGAAGACCCTTCACTGTTGTGGCAGGTGTTTGGCAGTGCCAC  949

TGGCCTAGCTCGATATTATCCAGCTTCACCATGGGTTGATAATGGTAGAA  719
||||||  ||  ||||| |||||||| |||||||||||||||| | |||
TGGCCTGGCCCGGTATTACCCAGCTTCTCCATGGGTTGATAATAGCCGAA  999

CTCCAAATATGATTGACCTTTATGATGTACGCAGAAGACCATGGTACATC  769
| |||||  ||||||| |||||||||||||||||||||||||||||||||
CCCCAAACAAGATTGATCTTTATGATGTACGCAGAAGACCATGGTACATC  1049

CAAGGAGCTGCATCTCCTAAAGACATGCTTATTCTGGTGGATGTGAGTGG  819
|||| ||||||||| ||||||||||||||||||||||||||||||||||
CAAGGTGCTGCATCCCCTAAAGATATGCTTATTCTGGTGGATGTGAGTGG  1099
```

FIGURE 3c

```
AAGTGTTAGTGGATTGACACTTAAACTGATCCAACATCTGTCTCCGAAA   869
||| |||||||||| |||||||| ||||| |||||| ||||| |||||||||||
AAGCGTTAGTGGACTGACACTCAAACTCATCCGGACATCCGTCTCCGAAA  1149

TGTTAGAAACCCTCTCAGATGATGATTTCGTGAATGTAGCTTCATTTAAC   919
|||| ||||||||||||||||||||||||| ||||| || ||||||||||
TGTTGGAAACCCTCTCAGATGATGATTTTGTGAACGTGGCTTCATTTAAC  1199

AGCAATGCTCAGGATGTAAGCTGTTTTCAGCACCTTGTCCAAGCAAATGT   969
|||||||||||||||||||||| |||||||||||||||||||||||||||
AGCAATGCTCAGGATGTAAGCTGCTTTCAGCACCTTGTCCAAGCAAATGT  1249

AAGAAATAAAAAGTGTTGAAAGACGCGGTGAATAATATCACAGCCAAAG  1019
|||||||| ||||||||||||| || ||||||||||||||||||| ||||
AAGAAATAAGAAAGTGTTGAAAGATGCAGTGAATAATATCACAGCAAAAG  1299

GAATTACAGATTATAAGAAGGGCTTTAGTTTTGCTTTTGAACAGCTGCTT  1069
|||| |||||||||||||||||||||||||||||||||||| ||||||||
GAATCACAGATTATAAGAAGGGCTTTAGTTTTGCTTTTGAGCAGCTGCTT  1349

AATTATAATGTTTCCAGAGCAAACTGCAATAAGATTATTATGCTATTCAC  1119
|||||||||| |||||||| |||||||||||||||||| ||| | |||||
AATTATAATGTATCCAGAGCCAACTGCAATAAGATTATCATGTTGTTCAC  1399

GGA...TGGAGAAGAGAGAGCCCAGGAGATATTTAACAAATACAATAAAG  1166
|||      ||||||||||||||||||||||||||| |||||||||||||
GGACGGAGGAGAAGAGAGAGCCCAGGAGATATTTGCCAAATACAATAAAG  1449

ATAAAAAACTACCTGTATTCACCTTCTCAGTTGGTCAACACAATTATGAC  1216
| || ||| ||| ||||||||| |||||||||||| |||| ||||| |||
ACAAGAAAGTACGTGTATTCACATTCTCAGTTGGCCAACATAATTACGAC  1499
```

FIGURE 3d

```
AGAGGACCTATTCAGTGGATGGCCTGTGAAAACAAAGGTTATTATTATGA   1266
||||||||||||||||||||||||| || |||||| ||||||||||||||||
AGAGGACCTATTCAGTGGATGGCTTGCGAAAATAAAGGTTATTATTATGA   1549

AATTCCTTCCATTGGTGCAATAAGAATCAATACTCAGGAATATTTGGATG   1316
|||||| |||||||| || |||||||| ||||||||||||||   ||||
AATTCCATCCATTGGAGCCATAAGAATTAATACTCAGGAATACCTAGATG   1599

TTTTGGGAAGACCAATGGTTTTAGCAGGAGACAAAGCTAAGCAAGTCCAA   1366
|| ||||||||| |||||||||||||||||||||||||||||||||||||
TTCTGGGAAGACCGATGGTTTTAGCAGGAGACAAAGCTAAGCAAGTCCAA   1649

TGGACAAATGTGTACCTGGATGCATTGGAACTGGGACTTGTCATTACTGG   1416
||||||||||||||||||||||||| ||||||||||||||||||||||||
TGGACAAATGTGTACCTGGATGCACTGGAACTGGGACTTGTCATTACTGG   1699

AACTCTTCCGGTCTTCAACATAACCGGCCAATTTGAAAATAAGACAAACT   1466
|||||||||||||||||||||||| |||||||||||||||||||||||||
AACTCTTCCGGTCTTCAACATAACTGGCCAATTTGAAAATAAGACAAACT   1749

TAAAGAACCAGCTGATTCTTGGTGTGATGGGAGTAGATGTGTCTTTGGAA   1516
|||||||||||||||||||||| ||||||||||||| |||||||||||||
TAAAGAACCAGCTGATTCTTGGAGTGATGGGAGTTGATGTGTCTTTGGAA   1799

GATATTAAAAGACTGACACCACGTTTTACACTGTGCCCCAATGG......   1560
|||||||||||||||||||||||||||||||| |||||||||||
GATATTAAAAGACTGACACCACGTTTTACACTCTGCCCCAATGGCTACTA   1849
```

5,710,250

CALCIUM CHANNEL ALPHA 2 SUBUNIT POLYPEPTIDES

This application is a continuation of U.S. application Ser. No. 08/314,083, filed Sep. 28, 1994, which is a divisional of U.S. application Ser. No. 07/914,231 (now U.S. Pat. No. 5,407,820, filed Jul. 13, 1992, which is a continuation of U.S. application Ser. No. 07/603,751, filed Nov. 8, 1990, now abandoned, which is a continuation-in-part of U.S. application Ser. No. 07/176,899, filed Apr. 4, 1988, now abandoned. U.S. application Ser. No. 07/603,751 is International PCT Application PCT/US89/01408, filed Apr. 4, 1989.

TECHNICAL FIELD

The present invention relates to molecular biology and pharmacology.

More particularly, the invention relates to calcium channel compositions and methods of making and using same.

BACKGROUND OF THE INVENTION

Calcium channels are membrane-spanning, multisubunit proteins hat allow controlled entry of $Ca^{+2}$ ions into cells from the extracellular fluid. All cells throughout the animal kingdom, and at least some bacterial, fungal and plant cells, possess one or more types of calcium channel.

The most common type of calcium channel is voltage-dependent. In a voltage-dependent channel, the "opening," to allow an influx of $Ca^{+2}$ ions into the cells to begin, requires a depolarization to a certain level of the potential difference between the inside of the cell bearing the channel and the extracellular medium bathing the cell and the rate of influx of $Ca^{+2}$ into the cell depends on this potential difference. All "excitable" cells in animals, such as neurons of he central nervous systems, peripheral nerve cells, and muscle cells, including those of skeletal muscles, cardiac muscles, and venous and arterial smooth muscles, have voltage-dependent calcium channels.

Calcium channels are physiologically important because the channels have a central role in regulating intracellular $Ca^{+2}$ levels and these levels are important for cell viability and function. Thus, intracellular $Ca^{+2}$ concentrations are implicated in a number of vital processes in animals, such as neurotransmitter release, muscle contraction, pacemaker activity, and secretion of hormones and other substances.

A number of compounds useful in treating various diseases in animals, including humans, are thought to exert their beneficial effects by modulating functions af voltage-dependent calcium channels. Many of these compounds bind to calcium channels and block, or reduce the rate of, influx of $Ca^{+2}$ into cells in response to depolarization of the inside and outside of the cells.

An understanding of the pharmacology of compounds that interact with calcium channels, and the ability to rationally design compounds that will interact with calcium channels to have desired therapeutic effects, have been hampered by a lack of understanding of the structure of channel subunits and the genes that code for them. Thus, it has not been possible to obtain the large amounts of highly purified channel subunits that are required to understand, at the molecular level, the nature of the subunits and their interactions with one another, with the cell membranes across which the channels allow $Ca^{+}2$ ions to pass, with $Ca^{+}2$ and other ions, and with low molecular weight compounds that affect channel function. For example, with the availability of large amounts of purified calcium channel subunits, functional channels could be prepared and used to screen the effects of compounds on channel function, thereby providing a basis for the design of therapeutic agents which affect the calcium channel, or various combinations of channel subunits could be crystallized and have their structures determined to high resolution employing X-ray or neutron diffraction techniques, providing yet another basis for rational design of therapeutic agents that affect channel function.

Certain diseases, such as Lambert-Eaton Syndrome, involve autoimmune interactions with calcium channels. The ready availability of calcium channel subunits would make possible immunoassays for diagnosis of such diseases and an understanding of them at the molecular level that could lead to effective methods for treating them.

The lack of information on genes that code for calcium channel subunits has prevented the understanding of the molecular properties of the mature calcium channel subunits and their precursor proteins (i.e., the mature subunits with signal peptides appended to the amino-terminus) and the regulation of expression of calcium channel subunits. An understanding of these properties, and of how expression of calcium channel subunit genes is regulated, may provide the basis for designing therapeutic agents which have beneficial effects through affecting calcium channel function or concentration Furthermore, the availability of sequences of genes coding for calcium channel subunits would make possible the diagnosis of defects, which might underlie a number of diseases, in genes coding for such subunits.

The availability of a DNA with the sequence of a segment, of at least about 12, and more preferably at least about 30, nucleotides of a cDNA encoding a subunit of a calcium channel from the cells of a tissue of an animal would make possible the isolation and cloning of cDNA's, and possibly genomic DNA's, coding for corresponding subunit of different calcium channels from the same or different tissues and animals of the same or different species. The availability of the sequences of numerous full-length cDNA's coding for corresponding subunits of calcium channels from a variety of tissues and animal species would contribute to elucidating structure-function relationships in the subunits and this knowledge, in turn, would be useful in the design of therapeutic agents whose activities are exerted through binding to calcium channels.

Voltage-dependent calcium channels are thought to consist of two large suunits, of between about 130 and about 200 kilodaltons ("kD") in molecular weight, and a number (generally thought to be one or three) of different smaller subunits, of less than about 60 kD in molecular weight. At least one of the larger subunits and possibly some of the smaller are glycosylated. Some of the subunits are capable of being phosphorylated. There is confusion in the art concerning the naming of the various subunits of voltage-dependent calcium channels.

The two large subunits of voltage-dependent calcium channels are designated herein the "(alpha)$_1$-subunit" and the "(alpha)$_2$-subunit".

The (alpha)$_1$-subunit is not detectably changed in molecular weight when treated with dithiothreito ("DTT") or with enzymes which catalyze removal of N-linked sugar groups from glycosylated proteins. The (alpha)$_1$-subunit has a molecular weight of about 150 to about 170 kD when analyzed by sodium dodecylsulfate ("SDS")-polyacrylamide gel electrophresis ("PAGE") after isolation from mammalian muscle tissue and has specific binding sites for various 1,4-dihydropyridines ("DHPs") and phenylalkylamines.

The (alpha)$_2$-subunit is somewhat less well characterized than the (alpha)$_1$-subunit. The molecular weight of the (alpha)$_2$-subunit is at least about 130–150 kD, as determined by SDS-PAGE analysis in the presence of DTT after isolation from mammalian muscle tissue. However, in SDS-PAGE under non-reducing conditions (in the presence of N-ethylmaleimide), the (alpha)$_2$-subunit migrates with a band of about 160–190 kD. It is not known in the art whether the smaller fragment (of about 30 kD), which appears to be released upon reduction, is the product of a gene different from the gens which encodes the 130–150 kD fragment (and, consequently, the two fragments are different subunits of the calcium channel) or whether both fragments are products of the same gens (and, consequently, the (alpha)$_2$-subunit is about 160–190 kD and is split into (at least) two fragments upon reduction). There is evidence that the (alpha)$_2$-subunit, whatever its size, and the corresponding fragment produced under reducing conditions, whether pan of the (alpha)$_2$-subunit or not, are glycosylated with at least N-linked sugars and do not have specified binding sites for 1,4-dihydropyridines and phenylalkylamines that are known to bind to the (alpha)$_1$-subunit.

Reference herein to the precursor of an (alpha)$_1$-subunit means the protein with the amino acid sequence corresponding to the sequence of the full-length mRNA which, upon translation, results, ultimately, in (alpha)$_1$-subunit resident as part of a calcium channel in a cell membrane. The precursor protein is converted by various processing steps into the (alpha)$_1$-subunit. The details of the processing between the precursor and the mature (alphail-subunit are not clear, but the processing possibly involves phosphorylation and also cleavage of the primary translation product to yield the mature (alpha)$_1$-subunit of the calcium channel.

Similarly, reference herein to the precursor of an (alpha) $_2$-subuniU means the protein with the amino acid sequence corresponding to the sequence of the full-length mRNA which, upon translation, results, ultimately, in (alpha)$_2$-subunit resident as part of a calcium channel in a cell membrane. The precursor protein is converted by various processing steps into the (alpha)$_2$-subunit. As with the (alpha)$_1$-subunit, the details of the processing between the precursor and the mature (alpha)$_2$-subunit are not clear, but the processing presumably involves at least removal of a leader sequence (i.e., a signal peptide), glycosylaticn, and, possibly, cleavage to yield what are now thought to be other subunits of the calcium channel.

The cDNA and corresponding amino acid sequence of the (alpha)$_1$-subunit precursor of a rabbit back skeletal muscle calcium channel has been reported. Tanabe et al., Nature 328, 313–318 (1987).

Calcium channel activity, measured electrophysiologically by voltage-clamp techniques, has been induced in Xenopus laevis oocytes when total mRNA isolated from mammalian brain and cardiac muscle is injected into the oocytes. Also, it has been reported that calcium channel-containing preparations, when reconstituted into lipid bilayers, confer voltage-dependent calcium channel activity on the bilayers.

However, there is no evidence that the (alpha)$_1$-subunit alone or the (alpha)$_2$-subunit alone provides a functional calcium channel in oocytes, lipid bilayers or any other situation. It has been recently reported by Eofmann, et al., Trends in Pharmacolog. Sci. 8, 393–398 (1987) that mRNA prepared using the cDNA of (alpha)$_1$-subunit obtained by Tanabe, et al. was unable to induce calcium channel activity in Xenopus laevis oocytes.

BRIEF DESCRIPTION OF THE FIGURES

FIG. 1 sets forth the nucleotide sequence of the cDNA encoding the (alpha)$_1$-subunit of the rabbit skeletal calcium channel and the amino acid sequence encoded by the 5,619 nucleotide open reading frame, which encodes a sequence of 1,873 amino acids. The 3' non-coding sequence of the cDNA is 234 nucleotides in length, excluding the poly (dA) tract, and contains a consensus polyadenylation signal ATTAAA (nucleotides 5832–5837) 17 nucleotides upstream from the poly (dA) tract.

FIG. 2 sets forth the 3,802 nucleotide and amino acid sequences of the rabbit skeletal calcium channel (alpha)$_2$-subunit. The figure includes the nucleotides of the cDNA that encodes the (alpha)$_2$-subunit precursor, including the 308 nucleotides of the 5' untranslated sequence, the 3,318 nucleotide open reading frame and 176 nucleotides of 3' untranslated sequence. The signal peptide of the (alpha)$_2$-subunit is shown as the first 26 negatively numbered amino acids.

FIG. 3 compares the sequences of the DNA encoding the rabbit skeletal $\alpha_2$-subunit.

The boxes in the figures enclose transmembrane regions. The symbol, P, denotes a phosphorylation site and the symbol, *, indicates a N-glycosylation site.

DETAILED DESCRIPTION OF THE INVENTION

In short, we have discovered a cDNA which codes for the (alpha)$_1$-subunit of an animal calcium channel (see FIG. 1) and a cDNA which codes for the (alpha)$_2$-subunit of an animal calcium channel (see FIG. 2 and Example 4).

Thus in one of its aspects, the invention is a DNA which comprises a cDNA which codes for the (alpha)$_2$-subunit of an animal calcium channel, and the RNA, coding for such a subunit, made upon transcription of such a DNA according to the invention.

In another of its aspects, the invention is a substantially pure (alpha)$_2$-subunit of an animal calcium channel.

By a "substantially pure" subunit or protein is meant a subunit or protein that is sufficiently free of other polypeptide contaminants to be considered homogeneous by SDS-PAGE or to be unambiguously sequenced.

In another of its aspects, the invention entails an eukarotic cell with an heterologous calcium channel, said cell made by a process comprising administering to said cell a first composition, which consists essentially of a first RNA which is translatable in said cell into the precursor of the (alpha) $_1$-subunit of a calcium channel of an animal of a first species, and a second composition which consists essentially of a second RNA which is translatable in said cell into the precursor of the (alpha)$_2$-subunit of a calcium channel of an animal of a second species, said first and second species being the same or different, provided that at least one of said precursor of said (alpha)$_1$-subunit and said precursor of said (alpha)$_2$-subunit is foreign to said cell. Preferred cells for this purpose are Xenopus laevis oocyes.

In another of its aspects, the invention entails a method for assaying a compound for calcium channel agonist or antagonist activity which comprises electrophysiologically measuring the calcium channel activity of a cell described in the immediately preceeding paragraph when such cell is exposed to a solution of the compound being tested for such activity. For similar methods applied with Xenopus laevis oocytes and acetylcholine receptors, see e.g., Mishna et al. Nature 313, 364 (1985) and, with such oocytes and sodium channels, see Noda et al., Nature 322, 826–828 (1986).

In a further of its aspects, the invention is an eukaryotic cell containing a DNA which comprises a cDNA which can be expressed to make the (alpha)$_2$-subunit of a calcium channel. Such a cell according to the invention can also contain a DNA which comprises a cDNA which can be expressed to make the (alpha)$_1$-subunit of a calcium channel. Preferably, the (alpha)$_2$-subunit or the (alpha)$_1$-subunit made from such a cDNA in such a cell will be foreign to the cell, i.e., will have an amino acid sequence which differs from that of any calcium channel (alpha)$_1$-subunit or (alpha)$_2$-subunit which occurs in a cell of the same type which does not contain a DNA from which the (alpha)$_1$-subunit or the (alpha)$_2$-subunit encoded by such a cDNA is expressed. Preferred among such cells are tho&e of mammalian origin, such as COS cells, NIH3T3 cells, mouse L cells or the like, or those of yeast such as S. cerevisiae or P. pastoris. Methods of making such cells of the invention, by transforming cells with suitable heterologous DNAs, o be maintained in the cell as episomes or (preferably) integrated into chromosomal DNA of the cell, and then culturing transformants or subcul turing (or passaging, in the case of mammalian cells) from such a culture or a subculture thereof, are well known to those of ordinary skill.

Among such cells of the invention, the invention entails also an eukaryotic cell with an heterologous calcium channel, said calcium channel made by a process comprising expression of a first cDNA, which codes for the precursor of the (alpha)$_1$-subunit of a calcium channel of an animal of a first species, and a second cDNA, which codes for the precursor of the (alpha)$_2$-subunit of a calcium channel of a second species, said first and second species being the same or different. Usually at least one of said precursor of said (alpha)$_1$-subunit and said precursor of said (alpha)$_2$-subunit is foreign to said cell. Again, preferred among such cells are those of mammalian origin or those of yeast such as S. cerevisiae cells or P. pastoris. In a preferred embodiment, such a cell will also contain another heterologous gens, which comprises a transcriptional control element (e.g., a promoter or promoter/enhancer combination), which is active in said cell and the transcriptional activity of which responds to an ion or molecule capable of entering said cell through a functional calcium channel (e.g., Ca$^{++}$Ba$^{++}$, Ca$^{++}$ ionophores), linked operatively for expression to a structural gens for an indicator protein, such a chloramphenicol acetyltransferase, luciferass or β-galactosidase.

These cells of the invention, which have functional, foreign calcium channels (i.e., functional calcium channels wherein at least one of the (alpha)$_1$-subunit and the (alpha)$_2$-subunit is foreign to the cell) will be useful for, among other purposes, assaying a compound for calcium channel agohist or antagonist activity. First, such a cell can be employed to measure the affinity of such a compound for the functional calcium channel. Secondly, such a cell can be employed to measure electrophysiologically the calcium channel activity in the presence of the compound being tested as well as a ion or molecule, such as Ca$^{++}$ or Ba$^{++}$, which is known to be capable of entering the cell through the functional channel. For similar studies which have been carried out with the acetylcholine receptor, see Claudio etal. Science 238 1688–1694 (1987). These methods for assaying a compound for calcium channel agohist or antagonist activity are also part of the present invention.

Such cells according to the invention, in the preferred embodiment, wherein the cell also contains an heterol ogous gens with a transcriptional control element, which is active in the cell and responsive to an ion or molecule capable of entering the cell through a functional calcium channel and is linked operatively for expression to a structural gene for an indicator protein, can also be employed, in another method according to he invention for assaying a compound for calcium channel agohist or antagonist activity. This method comprises exposing a culture of such cells to a solution of a compound being tested for such activity, together with an ion or molecule, which is capable of entering the cells through a functional calcium channel and affecting the activity of the transcriptional control element controlling transcription of the gens for the indicator protein, and comparing the level of expression, in the cells of the culture, of the gens for the indicator protein with the level of such expression in the cells of another, control culture of such cells.

A "control culture," as clearly understood by the skilled, will be a culture that is, and is treated, substantially the same as the culture exposed to the compound being assayed except that the control culture is not exposed to the compound being assayed. Levels of expression of the genes for the indicator proteins are ascertained readily by the skilled by known methods, which involve measurements of the concentration of indicator protein via assays for detectable compounds produced in reactions catalyzed by the indicator protein.

As indicated above, indicator proteins are enzymes whic are active in the cells of the invention and catalyze production of readily detectable compounds (e.g., chromogens, fluorescent compounds).

In a still further aspect, the invention is a method for diagnosing Lambert-Eaton Syndrome in a person by immunoassay which method comprises combining serum from the person with (alpha)$_1$-subunit of a first animal species and (alpha)$_2$-subunit of a second animal species (the same as or different from the first species) and ascertaining whether antibodies in the serum react with one or both of the subunits to a greater extent than antibodies in control serum (e.g., from a person or group of persons known to be free of the Syndrome). Any immunoassay procedure known in the art for detecting antibodies in serum against a given antigen can be employed in the method. Preferably, in the method, both of the (alpha) subunits are from a mammalian calcium channel, most preferably human.

The invention entails also a labeled (e.g., $^{32}$p or a biotinylated) RNA or single-stranded DNA of at least 12 (preferably at least 30) bases in length in a sequence which comprises. a sequence of at least 12 (preferably at least 30) contiguous bases between bases −238 and 3495, inclusive, in FIG. 2 below, or such a labeled RNA or single-stranded DNA with a sequence taken from the cDNA, described in Example 4, which encodes an human neuronal (alpha)$_2$-subunit. The use of such DNAs and RNAs as probes, to identify and isolate cDNAs coding calcium channel (alpha) $_2$-subunits or to identify tissue in which (alpha)$_2$-subunit mRNA is made, is clear to the skilled. In this regard, see, e.g., Example 4.

The primary strategy for cloning cDNAs encoding the (alpha)$_1$ and the (alpha)$_2$ polyeptide subunits of the DHP-sensitive calcium channels from rabbit skeletal muscle was to screen rabbit back skeletal muscle lambda gt11 cDNA expression libraries with antibody probes specific to each of the proteins. See generally Ausubel et al. Current Protocols in Molecular Biology, Wiley-interscience. New York (1987); Davis et al. Basic Methods in Molecular Biology, Elsevier Science Publishing Co., New York (1986). Monoclonal antibodies capable of immunoprecipitating the M$_r$ 155K–170K DHP receptor (alpha)$_1$ protein from rabbit skeletal muscle triads have been described previously by Leung, et al. J. Biol. Chem. 262, 7943–7946 (1987). Polyclonal antisera specific for the (alpha)$_2$ polypeptide subunit was prepared in guinea pigs using SDS polyacrylamide gel purified (alpha)$_2$ protein as described by Nakayama, et al. J. Biol. Chem. 262, 6572–6576 (1987). One of the (alpha)$_1$-specific monoclonal antibodies, designated as IIF7 by Leung, et al. supra, and the (alpha)$_2$-specific polyclonal antisera were used for screening of 1.0×10$^6$ recombinant phages of an oligo-dT primed lambda gt11 cDNA library. Probes based on the Tanabe et al. (alpha)$_1$-subunit cDNA sequence (Nature 328, 313–318 (1987)) could also be used to identify clones with fragments of the (alpha)$_1$-subunit cDNA.

Once a positive clone was found using an antibody-screening method, the clone was used to screen further for overlapping clones. A sequential series of overlapping clones was thus generated. These clones were sequenced and fragments were subcloned into either pIBI 24/25 (IBI, New Haven, Conn.) or M13 mp18/19. In cloning the (alpha)$_1$-subunit, the DNA sequence was compared to the primary sequence of the DHP receptor (alpha)$_1$-subunit reported by Tanabe et al. Nucleotide differences resulting in amino acid differences were confirmed by sequencing in both directions.

As pertains to the (alpha)$_1$-subunit, initially, two cDNA clones which reacted positively with the IIF7 monoclonal antibody were isolated and found to be related by cross-hybridization.

DNA sequencing of one of these clones revealed the presence of a cDNA insert of 453 base pairs (bp). Significantly, this insert coded for a 151 amino acid open reading frame with 28% homology to a region for the Electrophorus electroplax sodium channel sequence. The cDNA insert derived from this clone was used to rescreen the lambda gt11 cDNA library and a rabbit back skeletal muscle Okayama-Berg cDNA library (MacLennan, et al., Nature 316, 696–700 (1985)) to isolate overlapping cDNA clones. The cDNA clones were analyzed using the dideoxy chain-termination method of Sanger to determine the entire coding sequence of the (alpha)$_1$ subunit of the calcium channel and a restriction map was made for comparison and orientation of DNA sequences.

An oligo-dT-primed expression cDNA library was constructed in lambda g11, using young adult rabbit back skeletal muscle poly (A+) RNA (kindly provided by J. Robbins, University of Cincinnati) isolated in guanidine isothiocyanate (see Gubler, et al., Gene 25, 263–269 (1983) Lapeyre, et al., Gene 37,215–220 (1985) Huynh et. al, DNA Cloning: A Practical Approach, Vol. I 49–78 (IRL, Oxford, 1985)). Double-strand cDNA was synthesized and EcoRI adapaters were added. After the addition of the adapters, the double-strand cDNA was size-selected on a Sepharose CL-4B or Bio-Gel A-50 m column. Fragments>1500 bp were ligated into EcoRI digested, dephosphorylated lambda gt11. The library was packaged in vitro with Gigapack-plus, (Stratagene, San Diego, Calif.) and an efficiency of >95% recombinants was determined by plating in the presence of X-gal and IPTG. Two clones of a total 1×10$^6$ recombinants were identified by screening the expression library with monoclonal Ab IIF7 reactive with the M$_r$ 170,000 (alpha)$_1$ subunit of the rabbit skeletal muscle calcium channel. Positive plaques were visualized by binding HRP-goat anti-mouse IgG followed by color development with 4-chloro-1-naphthol. Each clone contained a ~500 bp insert and was related by cross-hybridization. One clone was DNA sequenced to identify an open reading frame (nts 2847–3300) and was used to identify a 6.5 Kb transcript by Northern analysis The 453 bp insert noted above was used to rescreen the lambda gill library and 8 of 1×10$^6$ clones were positive. One clone (1700 bp) extended the farthest 5' to nt 2237; its 522 bp PstI fragment, nts 2294–2816, was used to screen 1×10$^6$ transformants of a rabbit back skeletal muscle cDNA library constructed according to the method of Okayama and Berg (see MacLennan, et. al., Nature 316, 696–700 (1985)). Three positive clones were isolated, of which the largest (5.0 Kb) extended 5' to nt −750. The Okayama-Berg cDNA library was rescreened with a 5' 250 bp (PstI)-EcoRI fragment (the PstI site is donated by the Okayama-Berg vector) (nts −750–1006). The longest clone isolated, of 5 positives, was 5.3 Kb, extending 5' to nt −450. To clone the 5' end of (alpha)$_1$, a random primed rabbit back skeletal muscle lambda gt11 cDNA library was synthesized as described above with the following modifications: (1) pd(N)$_6$ hexamers (Pharmacia, Inc. Piscathaway, N.J.) were used to random prime the first strand cDNA reaction, (2) Adapters containing NcoI, KpnI, and EcoRI sites:

```
5'-CCATGGTACCTTCGTTGACG-3'
3'-GGTACCATGGAAGCAACTGCTTAA-5'
``` were ligated to the double-strand cDNA as described above, and (3) the double-strand cDNA was size-selected on a 1 ml Bio-Gel A50 column. Fragments>600 bp were ligated into lambda gt11. 1×10$^6$ recombinants of this library were screened in duplicate with the 1,648 bp EcoRI/XhoI fragment corresponding to nt 1006–2653 and an oligonucleotide probe spanning the initiating methionine: 5'-GGGAAGCCATGGAGCCATCCTCACCCCAGG-3'. Forty clones were positive with both probes, of which one (1.55 Kb) extended 78 nts 5' of the start codon and −450 bp 3' of the EcoRI site.

FIG. 1 (below) shows the 5,975 nucleotide sequence of the cDNA encoding the (alpha)$_1$-Subunit. There is a 5,619 nucleotide sequence reading frame which encodes a sequence of 1,873 amino acids (FIG. 1). The sequence context of the designated initiation codon is consistent with the proposed consensus sequence of Kozak, Nucleic Acids Res. 15, 8125–8132 (1987). The 3' non-coding sequence of the cDNA is 234 nucleotides in length, excluding the poly (dA) tract, and contains a consensus polyadenylation signal ATTAAA (nucleotides 5832–5837) 17 nucleotides upstream from the poly (dA) tract. This cDNA sequence is consistent with an −6,500 nucleotide DHP receptor (alpha)$_1$ mRNA. Furthermore, the DNA sequence is 99.4% identical to the cDNA sequence encoding the DHP receptor reported by Tanabe, et. al., supra. Nucleotide differences were identified at 33 positions, of which three, nucleotides 5423, 5444 and 5504 also result in amino acid changes.

As pertains to the (alpha)$_2$-subunit, in an initial screen with the guinea pig (alpha)$_2$-specific, polyclonal antisera, three cDNA clones were isolated and shown to be related to each other but not any (alpha)$_1$ cDNA sequences by cross-hybridization. Two of these cDNA clones were used to rescreen the lambda gt11 cDNA library to isolate overlapping cDNA clones. The cDNA clones were analyzed to establish the coding DNA sequence of the (alpha)$_2$ subunit of the calcium channel and a restriction map was made. Approximately 7,850 nucleotides of (alpha)$_2$ cDNA was cloned, which is consistent with an −8,000 nucleotide (alpha)$_2$ mRNA.

An oligo-dT-primed expression cDNA library was constructed in lambda gt11, using young adult rabbit back skeletal muscle poly (A+) RNA as described for the (alpha)$_1$-subunit. Double-stranded cDNA fragments>1500 bp were ligated into lambda gt11 and a primary plating of 1×10⁶ recombinants was screened with guinea pig anti-160 Kd (alpha)₂ polyclonal anti-sera. Three positive plaques were visualized by binding HRP-Protein A, followed by color development with 4-chloro-1-naphthol. Two clones, (2.5 Kb and 3.6 Kb) overlapped to encode 4.75 Kb of an ~8 Kb transcript identified by Northern analysis. (alpha)₂ cDNA clones extending in the 5' and 3' direction (oriented by DNA sequencing and identification of a long open reading frame) were isolated by rescreening the same lambda gt11 cDNA library with the (EcoRI)-HindIII fragment of one clone (nts 43–272, 5' proximal; EcoRI site from adapter) or the EcoRI—(EcoRI) fragment of a second clone (~1.0 Kb in the 3' untranslated region). A total of 14 clones were isolated, seven from each end, of which an overlapping pair of clones (one extending ~2,750 nts 3' and the other extending 350 nts 5') encoded ~7850 nts of the (alpha)₂ transcript; 308 nts of 5' untranslated sequence, 3318 nts of coding sequence, and ~4224 nts of 3' untranslated sequence. Only 176 nts of 3' untranslated sequence was confirmed in both directions and is reported.

FIG. 2 represents the 3,802 nucleotides of the cDNA sequence encoding the (alpha)₂-subunit and its precursor, including 308 nucleotides of 5' untranslated sequence, a 3,318 nucleotide open reading frame, and 176 nucleotides of 3' untranslated sequence.

FIG. 2 also shows the signal peptide of he (alpha)₂-subunit, shown as the first 26 negatively numbered amino acids. An arrow identifies he cleavage site between the signal peptide and he mature (alpha)₂-subunit. The N-terminal amino acid sequence previously determined is shown in bold sequence (Thr(+8), Trp(+12), and Asp(+14) were not previously determined.) The nucleotide sequence shown was determined from two clones which overlapped to span the coding sequence of the (alpha)₂-subunit. Five nucleotide differences among individual clones were observed resulting in four amino acid changes. Differences occurred in the sequence at positions 169, 347, 348, 984, and a deletion of nts 1858–1860. The amino acids were finally determined to be as follows: Asn at residue 31, Lys at residue 90, and a deletion of Ser at residue 594. An in-frame upstream stop codon is underlined as well as the start and stop codons of an upstream short open reading frame. Three putative transmembrane regions are enclosed in boxes. Potential N-glycosylation and phosphorylation sites are indicated as described for FIG. 1.

The open reading frame encodes a sequence of 1,106 amino acids (FIG. 2). The previously determined NH₂-terminal amino acid sequence of the (alpha)₂ protein is encoded by nucleotides 79–129 in the same open reading frame (amino acid residues 1–17, FIG. 2). The nucleotide sequence adjacent to the designated initiating codon agrees with the proposed consensus sequence. An in-frame termination codon is present upstream beginning at nucleotide −27. In addition, an out-of-frame potential initiation codon is located beginning at nucleotide −229 and is followed by a nonsense codon at nucleotides −179 to −181. The 5' untranslated sequence of the (alpha)₂ cDNA, 308 nucleotides cloned and sequenced thus far, is unusually long. This region is extremely G+C rich, approximately 80% G+C, which is similar to other relatively long 5' non-coding sequences which have been reported.

FIG. 1 shows the 1,873 amino acid sequence deduced from the cDNA of the (alpha)₁ subunit of the rabbit skeletal muscle calcium channel. Based on the identification of a clone using the (alpha)₁-specific IIF7 monoclonal antibody, we have determined that the protein sequence encoded by he 453 bp cDNA insert (amino acid residues 950–1,100) contains the epitope recognized by this monoclonal antibody. The complete sequence yields a calculated $M_r$ of 212,143 for the (alpha)₁ protein, in contrast to the observed $M_r$ 155K–170K, previously reported by others using SDS polyacrylamide gel electrophoresis. The amino acid sequence determined and reported here is 99.8% identical to that recently described by Tanabe et al., supra, showing three amino acid differences at residues 1,808 (Thr to Met), 1,815 (Ala to Val), and 1,835 (Ala to Glu). The calcium channel (alpha)₁-subunit protein contains five potential N-glycosylation sites at Asn residues 79, 257, 797, 1,464, and 1,674 and seven potential cAMP-dependent phosphorylation sites at Ser residues 687, 1,502, 1,575, 1,757, 1,772, and 1,854, and Thr 1,552. Analogous to the (alpha)-subunit of the sodium channel, the (alpha)₁-subunit of the skeletal muscle calcium channel contains four internal repeated sequence regions. An analysis of the hydropathy profile of the (alpha)₁-protein sequence reveals that each repeat contains five hydrophobic segments and one segment with strong positive charge. Since the (alpha)₁-protein sequence lacks an hydrophobic amino-terminal sequence characteristic of a signal peptide, it has been proposed that the segments of the four internally repeated regions represent twenty-four transmembrane segments and that the amino-and carboxy-termini extend intracellularly. That model is consistent with two of the potential glycosylation sites (Asn residues 79 and 257) being localized extracellularly and all of the potential phosphorylation cites being localized intracellularly. This generally agrees with previous biochemical studies suggesting that the (alpha)₁-subunit (which has been identified as the putative 1,4-dihydropyridine receptor) is not glycosylated but is phosphorylated.

FIG. 2 shows the 1,106 amino acid sequence deduced from the cDNA of the (alpha)₂-subunit of the rabbit skeletal muscle calcium channel. The sequence yields a calculated $M_r$ of 125,018 for this protein, in contrast to the observed $M_r$ 165K–175K (under non-reducing conditions $M_r$ 135K–150K under reducing conditions) determined previously by SDS polyacrylamide gel electrophoresis. The (alpha)₂ amino acid sequence deduced here from the cDNA confirms the sequence of 17 amino acids reported earlier as supposedly that of the amino terminal 17 amino acids of the (alpha)₂-subunit. The (alpha)₂-subunit precursor has a 26 amino acid (residues −1 to −26) signal peptide. While this proposed signal peptide is hydrophobic and of an appropriate length characteristic of signal sequences, it is somewhat unusual in that the peptide has Glu at position-1 and the Gln at position-12 defines a rather short central hydrophic region. The (alpha)₂ protein contains 18 potential N-glycosylation sites (Asn residues 68, 112, 160, 300, 324, 444, 451, 580, 589, 652, 671, 758, 801, 865, 872, 962, 975, and 1,005) and two potential cAMP-dependent phosphorylation sites at Thr 477 and Ser 822 (FIG. 2).

An analysis of the (alpha)₂ protein sequence for regional hydropathy reveals that, in distinct contrast to similar analysis of the (alpha)₁ protein, this protein is substantially hydrophilic, although it does contain a number of hydrophobic regions. Further characterization of the hydrophobic regions of polarity index and hydrophobic moment analyses indicates that three segments may represent transmembrane domains of the (alpha)a protein. The topography of the (alpha)₂ protein is not, however, easily predicted from the deduced primary amino acid sequence. This problem is further compounded by the determination that the (alpha)₂ protein lacks significant homology with any protein in the Dayhoff protein sequence database or with other known ion channel and receptor proteins. If the proposed (alpha)$_2$ signal sequence is, in fact, cleaved between the Glu-residue at position −1 and the Glu residue at position, then the amino terminus of the mature protein would be extracellular. Furthermore, assuming that the three hydrophobic segments function as transmembrane domains, and that there are only three such domains, the carboxyl-terminus of the (alpha)$_2$ protein would be intracellular. Such a transmembrane topography would be consistent with 8 out of the 18 potential N-glycosylation sites being localized extracellularly and the single potential phosphorylation site being localized intracellularly. Previous biochemical studies indicate that the (alpha)$_2$-subunit of the skeletal muscle calcium channel is not phosphorylated but is extensively glycosylated.

Rabbit and human genomic DNAs were digested with various restriction enzymes and Southern blots of these DNAs were hybridized with radiolabeled cDNA clones specific for the (alpha)$_1$-subunit or the (alpha)$_2$-subunit. Under conditions of high stringency, very few hybridizing bands were observed in rabbit genomic DNA with either the (alpha)$_1$- or (alpha)$_2$-specific probes. This result is consistent with a low-copy number, perhaps only a single-copy, of each of the (alpha)$_1$- and (alpha)$_2$-subunit genes in the rabbit genome. Southern blot of the same DNA preparations were also probed under conditions of low stringency with the same (alpha)$_1$- and (alpha)$_2$-specific probes. While additional hybridizing bands were observed in rabbit genomic DNA under low stringency conditions with both the (alpha)$_1$- and (alpha)$_2$-specific probes, substantially greater hybridization was observed with the (alpha)$_1$-specific cDNA probes. These results suggest that the (alpha)$_1$- and (alpha)$_2$-subunits of the skeletal muscle DHP-sensitive calcium channel may share significant homology with genes encoding other voltage-dependent DHP-sensitive calcium channels, voltage-dependent calcium channels which are not DHP-sensitive (e.g., T- and N-types), and possibly ligand-gated calcium channels (e.g., glutamate receptor). Interestingly, hybridization bands were observed in human genomic DNA with the (alpha)$_1$-specific cDNA probes under both high and low stringency conditions, whereas significant hybridization of (alpha)$_2$-specific cDNA probes were observed only under low stringency conditions. Thus, while there are human genes homologous to the rabbit (alpha)$_1$- and (alpha)$_1$-subunit genes, greater evolutionary sequence divergence may have occurred in the (alpha)$_2$ gene relative to the (alpha)$_1$ gene.

A further aspect of the invention provides for a diagnostic assay for Lambert Eaton Syndrome (LES). LES is an autoimmune disease characterized by an insufficient release of acetylcholine from motor nerve terminals which normally are responsive to nerve impulses. A recent publication (Kim and Neher, Science 239, 405–408 (1988)) demonstrates that IgG from LES patients block individual voltage-dependent calcium channels and thus prevent function. A diagnostic assay for LES based on immunological reactivity of LES IgG with calcium channel (alpha)$_2$-subunit alone or in combination with (alpha)$_1$-subunit is thus provided for. For example, such an assay may be based on immunoprecipitaion of LES IgG by the calcium channels subunits of the invention.

EXAMPLE 1

Isolation of RNA for cDNA Library

On the day before RNA is isolated, prepare the following. As a precaution, all glassware should be baked and all stock solutions in the list immediately below should be sterilized by autoclaving.

200 ml of 0.1 NaOAc, pH 5.2, 1 mM EDTA 50 ml of 0.2M Na$_2$ EDTA, pH 8.0.

50 ml of 1M Tris, pH 7.5

50 ml of 3.2 Tris, pH 7.2

50 ml of 0.01M Tris (pH 8.0), 1 mM EDTA 50 ml PK buffer (0.1M Tris, pH 7.2, 50 mM NaCl, 10 mM EDTA)

50 ml of 10% SDS, 4 l of ultrapure H$_2$O

On the morning of the RNA isolation, combine:

100 ml H$_2$O 100 g guanidine isothiocyanae (IBI)

10.6 ml 1M Tris, pH 7.5

10.6 ml 0.2M EDTA

Stir, but do not heat above 65° C. to dissolve guanidine isothiocyanate.

Dissect young adult rabbit back skeletal muscle on a clean glass plate and add about 10 g of muscle tissue (cut in −4mm pieces) to 50 ml of the guanidine isothiocyanate solution in e.g., a 100 ml Wheaton bottle.

Homogenize using "tissuemizer" from Tekman (large blade) for 10–20 sec., or until small pieces are no longer visible.

Place in 60° H$_2$O bath, add 30 ml of redistilled phenol which has been made 0.1% in 8-OH quinoline, 0.2% β-ME. Solution should be clear and homogenous after this addition.

Add 30 ml of a 1:1 solution of chloroform:acetate buffer.

Shake vigorously at 60° for 10 minutes; the solutions should appear opaque if not, add sufficient chloroform:acetate until it turns milky, Cool on ice, spin to separate phases (7000×g, 10–20 minutes)

Take off and pass it vigorously through a 22 gauge needle.

Treat with phenol:chloroform (1:1) saturated with acetate buffer. Extract aqueous larger with 3×volume of chloroform. Add 2 vol of −20° EtOH, and ppt for 1–2 hours, but no longer.

Collect precipitate; dry briefly (<5 minutes) under vacuum. Resuspend in 7 ml of PK buffer made 0.2% with respect to SDS. If precipitate develops, heat at 65° until solution clears. Add 1.5 mg of proteinase K.

Incubate 20 minutes at 37° (if you have dried for too long, RNA will be very difficult to get into solution and vigorous pipetting will be necessary throughout the incubation).

Extract reaction with 1:1 phenol:chloroform (made 0.1% in 8-OH quinoline, 0.2% β-ME, saturate with 100 mM Tris, pH 8.5 or PK buffer pH 7.7), 2×with chloroform, ppt by addition of 1/10 volume of 3.2M Tris, pH 7.5 and 2 vol. of EtOH. Poly A$^+$ RNA may then be isolated from the RNA mixture by well-known hybridization methods utilizing matrix-immobilized oligo (dT).

EXAMPLE 2 cDNA Cloning Procedure

1. First Strand Synthesis a. The following reagents and compositions are combine together and incubated on ice for 5 minutes:

| Reagent | Volume | Final Concentration |
|---|---|---|
| ~5 µg poly A+ RNA, plus water | to 10.5 µl | |
| 5X reverse transcriptase buffer | 10 µl | 1X |
| 0.5M DTT | 1 µl | 10 mM |
| RNasin (24 U/µl) | 2 µl | –IU/µl |
| 5X dNTPs | 10 µl | 1X |
| oligo dT (250 µg/ml) | 5 µl | 25 µg/ml | b. Next, the following three reagents are added to (a) and the mixture is incubated at 37° C. for 60 minutes:

| | | |
|---|---|---|
| actinomycin D (600 µg/ml) | 4 µl | ~50 µg/ml |
| $^{32}$P-gammadCTP (3200 Ci/mmol) | 2.5 µl | — |
| MMLV-reverse transcriptase (BRL-200 U/µl) | 5 µl | 200 U/µg RNA |
| | 50 µl | (total a + b) | c. The following reagents are added to (b) and the mixture is incubated at 37° C. for 30 minutes:

| | |
|---|---|
| RNasin (24 U/µl) | 1 µl |
| MMLV-reverse transcriptase (BRL-200 U/µl) | 3 µl | d. Take aliquots for analysis:

1 µl at time 0 for TCA

1 µl at 90 minutes for TCA 0.5 µl at 90 minutes for gel e. The reaction is stopped after 30 minutes adding 2 µl of 0.5M EDTA and performing one phenol/chloroform extraction, followed by one chloroform extraction. Then 10 µl of 10M NH$_4$OAc plus two volumes of ethanol are added to precipitate the first strand.

f. To analyze the synthesis, 0.5 µl of the reaction are run on a 1.5% agarose mini-gel, the gel is photographed, dried, and placed under film (generally an overnight exposure with an intensifying screen is adequate).

g. Calculate the mass of cDNA from the percent incorporation of label above background. 1 µg ss cDNA=1.4% incorporation.

2. Second Strand Synthesis a. The cDNA-RNA is spun down by centrifugation in a benchtop microfuge for 15 minutes. The pellet is washed in 95% ethanol and dried.

b. The following mixture is assembled and incubated at 12° C. for 60 minutes.

| | Volume | Final Concentration |
|---|---|---|
| cDNA RNA, plus water | to 68 µl | |
| 5X 2nd strand buffer | 20 µl | 1X |
| 10 mM β-NAD | 1.5 µl | 0.15 mM |
| 4 mM dNTPs | 5 µl | 200 µM/ml |
| DNA polymerase I (10 U/µl) | 2.5 µl | 250 U/ml |
| E. coli DNA ligase (2 U/µl) | 2 µl | 40 U/ml |
| RNase H (2.3 U/µl) | 1 µl | 23 U/ml |
| | 100 µl | | c. To this mix is added the following, and incubation continues at 22° C. for 60 minutes:

| | |
|---|---|
| DNA polymerase I (10 U/µl) | 1.5 µl |
| E. coli DNA ligase (2 U/µl) | 1.5 µl | d. The reaction is stopped after 60 minutes by adding 4 µl of 0.5M EDTA and performing one phenol/chloroform extraction and one chloroform extraction.

e. The aqueous phase is run over a G-50 column in a short Pasteur piper and 100 µl fractions are collected. The 500 µls containing the cDNA is collected and pooled, and butanol extracted down to a volume of ~50 µl. The cDNA is precipitated by adding 10 µl of 10M NH$_4$OAc plus two volumes of ethanol.

3. T4 Polymerase Reaction a. The cDNA is spun down in a microfuge for 15 minutes. A 95% ethanol wash is performed and the cDNA pellet is dried. The dry pellet is counted in a scintillation counter. Assume 100% efficiency of the 2nd strand reaction, and calculate mass of double-stranded cDNA from the first strand calculation.

b. To the cDNA is added the following, and mixture is incubated at 37° C. for 20 minutes.

| | |
|---|---|
| cDNA | + |
| 10X T4 buffer | 5 µl |
| H$_2$O | 40.75 µl |
| 4 mM dNTPs | 1.25 µl |
| 0.1 mM DTT | 2.5 µl |
| T4 polymerase (10 U/µl) | 0.5 µl |
| | 50 µl | c. Aliquots are taken:

0.5 µl for gel at time 0

0.5 µl for gel at 20 minutes d. The reaction is stopped after 20 minutes by adding 2 µl of 0.5M EDTA; followed by a phenol/chloroform extraction and a chloroform extraction.

e. The aqueous phase is run over a G-50 column in a short Pasteur piper and 100 µl fractions are collected. The 500 µls containing the cDNA is collected and pooled, and butanol extracted down to a volume of ~50 µl. The cDNA is precipitated by adding 10 µl of 10M NH$_4$OAc plus two volumes of ethanol.

f. The 0.5 µl samples taken at time 0 and 20 minutes are run on a 1.5% agarose mini-gel, which is subsequently photographed, dried, and placed under film.

4. Addition of EcoRI Adapters (for insertion into lambda gt11)

a. Oligos are synthesized having the following sequences:

20 mer: 5'-CCATGGTACCTTCGTTGACG-3'

24 mer: 3'-GGTACCATGGAAGCAACTGCTTAA-5' b. The 20 mer is phosphorylated by combining the following reagents and incubated at 37° C. for 15 minutes:

| | |
|---|---|
| 225 pmoles 20 mer | + |
| water | 6.8 µl |
| 10X kinase buffer | 1.2 µl |
| $^{32}$P-gammaATP (7000 Ci/mmole) | 1.0 µl |
| kinase (2 U/µl) | 1.0 µl |
| | 10 µl | c. The following two reagents are added to above mixture and it is incubated at 37° C. for 30 minutes:

| | |
|---|---|
| 10 mM ATP | 1 μl |
| kinase (2 U/ml) | 1 μl |
| | 12 μl (total b + c) | d. The enzyme is then inactivated by boiling for 10 minutes.

e. The 24 mer is hybridized to the phosphorylated 20 mer by addition of 225 pmoles of the 24 mer (plus water to bring volume to 15 μl), and incubation at 65° C. for 5 minutes. The reaction is then allowed to slow cool to room temperature.

The adapters are now present at a concentration of 15 pmoles/μl, and are ready for cDNA-vector ligation.

f. Combine the following:

| | |
|---|---|
| cDNA + hybridized adapters (15 pmol/μl) | 50-fold molar excess over cDNA |
| water | 16 μl |
| 10x ligase buffer | 2 μl |
| ligase (10 U/μl) | 2 μl |
| | 20 μl |

5. Phosphorylation of cDNA a. The ligase is inactivated by heating the mixture to 72° C. for 15 minutes.

b. The following reagents are added to the cDNA ligation reaction and it is heated at 37° C. for 30 minutes:

| | |
|---|---|
| cDNA ligation reaction | 20 μl |
| water | 24 μl |
| 10X kinase buffer | 3 μl |
| 10 mM ATP | 1 μl |
| kinase (2 U/μl) | 2 μl |
| | 50 μl | c. The reaction is stopped by the addition of 2 μl 0.5M EDTA, followed by one phenol/chloroform extraction and one chloroform extraction.

6. Purification and Size-Selection of cDNA a. The cDNA is run over a BIO-GEL A-50 column that has been washed with ≧5 ml of TE buffer. The column has 0.8 ml bed resin in a 0.2 cm (inner diameter)×30 cm siliconized glass tube with a glass wool plug in a yellow pipet tip at he bottom.

b. The cDNA is dried down in a speed vac to ~20 μl. 2.5 μl of gel loading dye is added and the cDNA is run over the column. The counts begin coming off after running 200–250 μl TE buffer through the column. 5 minute fractions (~30 μl) are collected and counted in a scintillation counter. Free adapters may begin to elute off 350–400 μl after the cDNA starts to elute.

c. 0.5 μl of several of the collected fractions are run on a 1.5% agarose minigel. The gel is photographed, dried down, and placed under film.

7. Ligation of cDNA to lambda gt11 vector a. The fractions containing cDNA are pooled, butanol extracted down to 20–30 μl, and 5 μl of 10M NH₄OAc plus two volumes of ethanol is added to precipitate the cDNA. It is spun in a microfuge for 15 minutes, and then subjected to a 95% ethanol wash and dry.

b. The pellet is counted, and the mass of cDNA is calculated relative to the mass after the second strand synthesis.

c. The cDNA is resuspended in TE (~0.10 pmol/μl).

d. The ligation reaction contains the following, which is incubated at 14°–16° C. overnight:

| (use 1 μg of lambda gt11 vector = 0.035 pmol vector) | |
|---|---|
| lambda gt11 (1 μg/μl) | 1 μl |
| cDNA insert | (2–4 fold molar excess of cDNA over vector) |
| water | to 3 μl |
| 5X ligase buffer | 1 μl |
| ligase (10 U/μl) | 1 μl |
| | 5 μl |

8. Packaging

The vector is packaged using the Gigapack in vitro packaging kit supplied by Strategene, and following the instructions contained therein.

| REAGENTS | |
|---|---|
| 5x RT buffer | |
| 250 mM Tris, pH 7.4 | 250 μl of 1M |
| 375 mM KCl | 375 μl of 1M |
| 15 mM MgCl₂ | 75 μl of 0.2M |
| H₂O | 300 μl |
| | 1000 μl |
| 5X dNTPs | |
| 5 mM dATP | 14.1 μl |
| 5 mM dCTP | 9.1 μl |
| 5 mM dGTP | 13.6 μl |
| 5 mM dTTP | 13.3 μl |
| | 50 μl |
| 5X 2nd Strand Buffer | |
| 100 mM Tris, pH 7.5 | 100 μl of 1M |
| 500 mM KCl | 500 μl of 1M |
| 50 mM (NH₄)₂SO₄ | 50 μl of 1M |
| 25 mM MgCl₂ | 125 μl of 0.2M |
| 250 μg/ml BSA | 5 μl of 50 mg/ml |
| water | 220 μl |
| | 1000 μl |
| 10X T4 buffer | |
| 670 mM Tris, pH 8.0 | 670 μl of 1M |
| 167 mM (NH₄)₂SO₄ | 167 μl of 1M |
| 67 mM MgCl₂ | 67 μl of 1M |
| H₂O | 96 μl |
| | 1000 μl |

EXAMPLE 3

Screening cDNA Library with Antibody

Plate lambda gt11 library on Y1090 in LB agar and 50 g/ml ampicillin. Grow overnight in 15 ml of LB, 0.2% maltose and 50 μg/ml ampicillin. Pellet the cells and resuspend in 3 ml of 10 mM MgSO₄. Plate four plates at 250,000 plaques/plate using 25 μl of phage (10,000/μl) and 300 μl of said 3 ml solution of cells in 10 ml soft agar containing 50 μg/ml ampicillin.

Grow at 42° C. for 2.5 hours and overlay IPTG-treated filters which were soaked in 10 mM IPTG (Boehringer Mannhiem Biochemicals, Indianapolis, Ind.). Dry filters until just moist, lay them in the plates and incubate overnight at 37° C.

Orient the plates and spot 0.5μl of purified DHP receptor on one plate as a positive control. Wash the filters for 10 min at room temperature TBS (50 mM TRIS, 150 mM NaCl, pH 8.0). Wash filters in TBS, 20% FCS (filtered) for 30 min at room temp.

Incubate the filters for 2 hours in TBS, 20% FCS, anti-DHS-receptor antibody (monoclonal or polyclonal). Wash for 10 min in TBS. Transfer filters to new plates and wash for 1 min in TBS, 0.1% $NP_4O$. Wash for 10 min in TBS and transfer to new plates.

Incubate for at least 1 hour with TBS, 20% FCS containing an appropriate second antiboby (e.g. HRP-Protein A; or HRP-goat anti-mouse IgG).

Wash filters as described above for the first antibody.

Develop the positive clones using about 40 ml/plate of 4-chloro-1-naphthol reagent which is made by dissolving 60 mg of said developer in 20 ml of ice cold MeOH and mixing 4-chloro-1-naphthol (Aldrich Chemical Company, Milwaukee, Wis.) into 100 ml of TBS containing 60 μl of 30% $H_2O_2$.

EXAMPLE 4

An Human Neuronal Calcium Channel (Alpha)$_2$-Subunit-Encoding cDNA

Because of the indications, mentioned supra, that human calcium channel (alpha)$_2$-subunit genes had diverged somewhat from rabbit calcium channel (alpha)$_2$-subunit genes, human (alpha)$_2$-subunit-encoding fragments were isolated to use as probes to screen human brain cDNA libraries under high stringency conditions.

Thus, an EcoRI-digested human genomic Southern blot was probed under both low and high stringency conditions with a fragment of rabbit (alpha)$_2$-subunit-encoding cDNA (the fragment from nucleotide 43 to nucleotide 272 indicated in FIG. 2). Under low stringency conditions, two genomic fragments were identified, of 3.0 kbp and 3.5 kbp in size. Under high stringency conditions, only the 3.5 kbp fragment maintained a stable hybrid. These two fragments were cloned into lambda-gt11. The 3.5 kbp fragment includes a small PstI-XbaI fragment, of about 300 bp, which includes an 82 bp exon with 96.4% homology to nucleotides 102 to 183 of the sequence in FIG. 2. This exon is preceded by the dinucleotide AG (splice donor) and followed by the dinucleotide GT (splice acceptor), as understood in the art. The 3.0 kbp fragment includes an XbaI-BglII fragment, of about 585 bp, which includes 104 bp of an exon (which includes the BglII site at its downstream end) which, in the 104 bp, has 93.3% homology to nucleotides 184 to 287 of the sequence in FIG. 2. Both the 300 bp, PstI-XbaI fragment and the 585 bp, XbaI-BglII fragments were used to probe duplicate lifts of a human basal ganglia cDNA library in lambda-gt11 (the library having been obtained from the American Type Culture Collection, Pockville, Md., USA, and containing about $10^6$ independent recombinants with an average insert size of 800–1000 bp). Three positive clones were identified which hybridized to both probes under high stringency conditions, one with an insert size of about 1150 bp, another with an insert size of about 790 bp, and the third with an insert size of about 670 bp. The 1150 bp insert in the one clone extended into the coding region from about nucleotide 200 in the coding region and was found to have a sequence more than 90% homologous to that of the corresponding segment of the cDNA whose sequence is presented in FIG. 2. Using the lambda genome with the 1150 bp insert as probe, an human brain stem cDNA library (also purchased from the American Type Culture Collection, and having about $4\times10^6$ independent recombinants with an average insert size of 800–1000 bp) was probed under high stringency conditions. In this probing, four positive clones were identified, with inserts of about 950 bp, 1120 bp, 3000 bp and 2500 bp. Most of the 1120 bp insert overlapped the 1150 bp insert of the DNA used as probe but extended somewhat upstream from the upstream end of the 1150 bp insert. The 2500 bp insert extended downstream from about 650 bp from the 5'-end of the 1120 bp insert. The DNA with the 2500 bp insert was used to again probe the brain stem library, and a clone with a 2750 bp insert was found. The 2750 bp insert was found by restriction analysis and sequencing to extend in the 3'-direction beyond the translational stop signal of a reading frame that was found to begin in the 1120 bp insert described above. The 2750 bp insert and 1120 bp insert have a PvuII site in common and have been ligated using the PvuII site to provide a cDNA that encodes a human neuronal calcium channel (alpha)$_2$-subunit. The 5'-1560 bp of this cDNA have been sequenced and, as illustrated in FIG. 3, found to be 91.2% homologous with the corresponding 1575 bp segment indicated in FIG. 2.

The human (alpha)$_2$-subunit-encoding cDNA will be subcloned into the mammalian expression vector pSV2DHFR, which is available in the art, for expression in mammalian tissue culture cells.

We obtained the human neuroblastoma cell line IMR32 from the American Type Culture Collection (accession no. CCL127). A northern blot analysis was carried out on poly A$^+$ RNA from this cell line using the full-length human (alpha)$_2$-subunit-encoding cDNA. Under low stringency washing, a single 8.2 kb fragment was found. The rabbit skeletal muscle (alpha)$_2$-encoding messenger RNA also had a size similar to 8.2 kb While he invention has been described herein with some specificity, the ordinarily skilled in the art will recognize numerous variations and modifications, in what is described, hat are within the spirit of he invention. Such variations and modifications are within the scope of the invention as described in the claims herein.

Various features of he invention are also described in the following claims.

What is claimed is:

1. A substantially pure (alpha)$_2$-subunit of a human calcium channel encoded by DNA comprising a sequence of nucleotides that encodes the (alpha)$_2$-subunit of a human calcium channel, wherein the sequence of nucleotides hybridizes under conditions of high stringency with a naturally occuring complementary DNA encoding a human calcium changed subunit that includes all or a portion of the nucleotide sequence set forth in FIG. 2a to 2f and the portion includes at least nucleotides 43–272 set forth in FIGS. 2a to 2f.

2. A substantially pure subunit of claim 1 that is a subunit of a skeletal muscle, cardiac or neuronal calcium channel.

3. A substantially pure subunit of claim 1 that is made by expressing in a eukaryotic cell cDNA encoding a subunit that comprises the sequence of amino acids set forth in SEQ ID No. 6.

4. A substantially pure subunit of claim 3, wherein the eukaryotic cell is a yeast cell or a mammalian cell.

5. The substantially pure subunit of claim 1, comprising a sequence of amino acids encoded by nucleotides 35–1558 of SEQ ID No. 3.

6. A substantially pure subunit of claim 1, that is a subunit of a human neuronal calcium channel.

7. A substantially pure subunit of claim 6 that is made by expressing in a eukaryotic cell a cDNA encoding a subunit that comprises the sequence of amino acids set forth in SEQ ID No. 3.

8. A substantially pure subunit of claim 7, wherein the eukaryotic cell is a yeast cell or a mammalian cell.

* * * * *

UNITED STATES PATENT AND TRADEMARK OFFICE
CERTIFICATE OF CORRECTION

PATENT NO. : 5,710,250  Page 1 of 2
DATED : January 20, 1998
INVENTOR(S) : Ellis *et al.*

It is certified that error appears in the above-identified patent and that said Letters Patent is hereby corrected as shown below:

IN THE TITLE PAGES:

In item [75], entitled Inventors, delete "Jean Sartor" as an inventor at column 1, line 36 replace "he" with —the—
at column 3, lines 11, 14 replace "gens" with —genes—
at column 3, line 18 replace "pan" with —part—
at column 4, line 21 replace "Figure 3 compares the sequences of the DNA encoding the rabbit skeletal $a_2$-subunit" with —Figure 3 compares the sequences of the DNA encoding the human neuronal $a_2$-subunit with that encoding the rabbit skeletal $a_2$-subunit—
at column 5, line 37 replace "gens" with —genes—
at column 5, line 18 replace "o" with —to—
at column 5, line 5 replace "agohist" with —agonist—
at column 5, line 64 delete the space between "heterol" and "ogous"
at column 6, line 3 replace "he" with —the—
at column 6, line 4 replace "agohist" with —agonist—
at column 6, line 26 replace "whic" with —which—
at column 10, line 27 replace "Ash" with —Asn—
at column 12, line 41 replace "larger" with —layer—
at column 18, line 2 replace "Pockville" with —Rockville—
at column 18, lines 53, 58, 62 replace "he" with —the—
at column 18, line 57, replace "hat" with —that—
at column 5, line 14, replace "thote" with --those--.

UNITED STATES PATENT AND TRADEMARK OFFICE
CERTIFICATE OF CORRECTION

PATENT NO. : 5,710,250

DATED : January 20, 1998

INVENTOR(S) : Ellis *et al.*

It is certified that error appears in the above-identified patent and that said Letters Patent is hereby corrected as shown below:

IN THE CLAIMS:
Delete claim 1 and replace with the following claim:

— 1. A substantially pure $(alpha)_2$-subunit of a human calcium channel encoded by DNA comprising a sequence of nucleotides that encodes the $(alpha)_2$-subunit of a human calcium channel, wherein the sequence of nucleotides hybridizes under conditions of high stringency with a naturally occurring complementary DNA encoding a human calcium channel subunit that includes all or a portion of the nucleotide sequence set forth in Figs. 2a to 2f and the portion includes at least nucleotides 43-272 set forth in Figs 2a to 2f. —

Signed and Sealed this

Eighteenth Day of May, 1999

Attest:

Q. TODD DICKINSON

*Attesting Officer*      *Acting Commissioner of Patents and Trademarks*

SEQUENCE LISTING ( 1 ) GENERAL INFORMATION:

( i i i ) NUMBER OF SEQUENCES: 6

( 2 ) INFORMATION FOR SEQ ID NO:1:

( i ) SEQUENCE CHARACTERISTICS:
        ( A ) LENGTH: 5975 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: Coding Sequence
        ( B ) LOCATION: 79...5700
        ( D ) OTHER INFORMATION:

( x i ) SEQUENCE DESCRIPTION: SEQ ID NO:1:

```
GCGGGAACA  CTGGGGACGC  AGGGAAGAGA  GGGCCGCGGG  GTGGGGGAGC  AGCAGGAAGC              60

GCCGTGGCCA  GGGAAGCC  ATG GAG CCA TCC TCA CCC CAG GAT GAG GGC CTG                 111
                     Met Glu Pro Ser Ser Pro Gln Asp Glu Gly Leu
                      1           5                      10

AGG AAG AAA CAG CCC AAG AAG CCC CTG CCC GAG GTC CTG CCC AGG CCG                   159
Arg Lys Lys Gln Pro Lys Lys Pro Leu Pro Glu Val Leu Pro Arg Pro
         15              20                  25

CCG CGG GCT CTG TTC TGC CTG ACC CTG CAG AAC CCG CTG AGG AAG GCG                   207
Pro Arg Ala Leu Phe Cys Leu Thr Leu Gln Asn Pro Leu Arg Lys Ala
             30                  35                  40

TGC ATC AGC ATC GTG GAA TGG AAA CCC TTC GAG ACC ATC ATC CTG CTC                   255
Cys Ile Ser Ile Val Glu Trp Lys Pro Phe Glu Thr Ile Ile Leu Leu
 45                  50                  55

ACC ATC TTT GCC AAC TGT GTG GCC CTG GCC GTG TAC CTG CCC ATG CCC                   303
Thr Ile Phe Ala Asn Cys Val Ala Leu Ala Val Tyr Leu Pro Met Pro
 60                  65                  70                  75

GAG GAT GAC AAC AAC TCC CTG AAC CTG GGC CTG GAG AAG CTG GAG TAC                   351
Glu Asp Asp Asn Asn Ser Leu Asn Leu Gly Leu Glu Lys Leu Glu Tyr
                 80                  85                  90

TTC TTC CTC ACC GTC TTC TCC ATC GAA GCC GCC ATG AAG ATC ATC GCC                   399
Phe Phe Leu Thr Val Phe Ser Ile Glu Ala Ala Met Lys Ile Ile Ala
             95                 100                 105

TAC GGC TTC CTG TTC CAC CAG GAC GCC TAC CTG CGC AGC GGC TGG AAC                   447
Tyr Gly Phe Leu Phe His Gln Asp Ala Tyr Leu Arg Ser Gly Trp Asn
        110                 115                 120

GTG CTG GAC TTC ATC ATC GTC TTC CTG GGG GTC TTC ACG GCG ATT CTG                   495
Val Leu Asp Phe Ile Ile Val Phe Leu Gly Val Phe Thr Ala Ile Leu
    125                 130                 135

GAA CAG GTC AAC GTC ATC CAG AGC AAC ACG GCC CCG ATG AGC AGC AAA                   543
Glu Gln Val Asn Val Ile Gln Ser Asn Thr Ala Pro Met Ser Ser Lys
140                 145                 150                 155

GGA GCC GGC CTG GAC GTC AAG GCC CTG AGG GCC TTC CGT GTG CTC AGA                   591
Gly Ala Gly Leu Asp Val Lys Ala Leu Arg Ala Phe Arg Val Leu Arg
            160                 165                 170

CCC CTC CGG CTG GTG TCG GGG GTG CCT AGT TTG CAG GTG GTC CTC AAC                   639
Pro Leu Arg Leu Val Ser Gly Val Pro Ser Leu Gln Val Val Leu Asn
        175                 180                 185

TCC ATC TTC AAG GCC ATG CTC CCC CTG TTC CAC ATC GCC CTG CTC GTC                   687
Ser Ile Phe Lys Ala Met Leu Pro Leu Phe His Ile Ala Leu Leu Val
        190                 195                 200

CTC TTC ATG GTC ATC ATC TAC GCC ATC ATC GGG CTG GAG CTC TTC AAG                   735
```

```
Leu Phe Met Val Ile Ile Tyr Ala Ile Ile Gly Leu Glu Leu Phe Lys
    205             210                 215

GGC AAG ATG CAC AAG ACC TGC TAC TAC ATC GGG ACA GAC ATC GTG GCC    783
Gly Lys Met His Lys Thr Cys Tyr Tyr Ile Gly Thr Asp Ile Val Ala
220             225             230                 235

ACA GTG GAG AAT GAG AAG CCC TCG CCC TGC GCT AGG ACG GGC TCG GGG    831
Thr Val Glu Asn Glu Lys Pro Ser Pro Cys Ala Arg Thr Gly Ser Gly
                240             245             250

CGC CCC TGC ACC ATC AAC GGC AGC GAG TGC CGG GGC GGC TGG CCG GGG    879
Arg Pro Cys Thr Ile Asn Gly Ser Glu Cys Arg Gly Gly Trp Pro Gly
            255             260             265

CCC AAC CAC GGC ATC ACG CAC TTC GAC AAC TTC GGC TTC TCC ATG CTC    927
Pro Asn His Gly Ile Thr His Phe Asp Asn Phe Gly Phe Ser Met Leu
        270             275             280

ACC GTG TAC CAG TGC ATC ACC ATG GAG GGC TGG ACA GAT GTC CTC TAC    975
Thr Val Tyr Gln Cys Ile Thr Met Glu Gly Trp Thr Asp Val Leu Tyr
    285             290             295

TGG GTC AAC GAT GCC ATC GGG AAC GAG TGG CCC TGG ATC TAC TTT GTC   1023
Trp Val Asn Asp Ala Ile Gly Asn Glu Trp Pro Trp Ile Tyr Phe Val
300             305             310                 315

ACT CTC ATC CTG CTG GGG TCC TTC TTC ATC CTC AAC CTG GTG CTG GGC   1071
Thr Leu Ile Leu Leu Gly Ser Phe Phe Ile Leu Asn Leu Val Leu Gly
                320             325             330

GTC CTG AGT GGG GAA TTC ACC AAG GAG CGG GAG AAG GCC AAG TCC AGG   1119
Val Leu Ser Gly Glu Phe Thr Lys Glu Arg Glu Lys Ala Lys Ser Arg
            335             340             345

GGA ACC TTC CAG AAG CTG CGG GAG AAG CAG CAG CTG GAG GAG GAC CTT   1167
Gly Thr Phe Gln Lys Leu Arg Glu Lys Gln Gln Leu Glu Glu Asp Leu
        350             355             360

CGG GGC TAC ATG AGC TGG ATC ACG CAG GGC GAG GTC ATG GAC GTG GAG   1215
Arg Gly Tyr Met Ser Trp Ile Thr Gln Gly Glu Val Met Asp Val Glu
    365             370             375

GAC CTG AGA GAA GGA AAG CTG TCC TTG GAA GAG GGA GGC TCC GAC ACG   1263
Asp Leu Arg Glu Gly Lys Leu Ser Leu Glu Glu Gly Gly Ser Asp Thr
380             385             390                 395

GAA AGC CTG TAC GAA ATC GAG GGC TTG AAC AAA ATC ATC CAG TTC ATC   1311
Glu Ser Leu Tyr Glu Ile Glu Gly Leu Asn Lys Ile Ile Gln Phe Ile
                400             405             410

CGA CAC TGG AGG CAG TGG AAC CGT GTC TTT CGC TGG AAG TGC CAT GAC   1359
Arg His Trp Arg Gln Trp Asn Arg Val Phe Arg Trp Lys Cys His Asp
            415             420             425

CTG GTG AAG TCG AGA GTC TTC TAC TGG CTG GTC ATC CTG ATC GTG GCC   1407
Leu Val Lys Ser Arg Val Phe Tyr Trp Leu Val Ile Leu Ile Val Ala
        430             435             440

CTC AAC ACC CTG TCC ATC GCC TCG GAG CAC CAC AAC CAG CCG CTC TGG   1455
Leu Asn Thr Leu Ser Ile Ala Ser Glu His His Asn Gln Pro Leu Trp
    445             450             455

CTG ACC CAC TTG CAA GAC ATC GCC AAT CGA GTG CTG CTG TCA CTC TTC   1503
Leu Thr His Leu Gln Asp Ile Ala Asn Arg Val Leu Leu Ser Leu Phe
460             465             470                 475

ACC ATC GAG ATG CTG CTG AAG ATG TAC GGG CTG GGC CTG CGC CAG TAC   1551
Thr Ile Glu Met Leu Leu Lys Met Tyr Gly Leu Gly Leu Arg Gln Tyr
                480             485             490

TTC ATG TCC ATC TTC AAC CGC TTC GAC TGC TTC GTG GTG TGC AGC GGC   1599
Phe Met Ser Ile Phe Asn Arg Phe Asp Cys Phe Val Val Cys Ser Gly
            495             500             505

ATC CTG GAG CTG CTG CTG GTG GAG TCG GGC GCC ATG ACG CCG CTG GGC   1647
Ile Leu Glu Leu Leu Leu Val Glu Ser Gly Ala Met Thr Pro Leu Gly
        510             515             520

ATC TCC GTG TTG CGC TGC ATC CGC CTC CTG AGG CTC TTC AAG ATC ACC   1695
```

| | | | | | | | | | | | | | | | | |
|---|---|---|---|---|---|---|---|---|---|---|---|---|---|---|---|---|
| Ile | Ser | Val | Leu | Arg | Cys | Ile | Arg | Leu | Leu | Arg | Leu | Phe | Lys | Ile | Thr | |
| | 525 | | | | 530 | | | | | | 535 | | | | | |
| AAG | TAC | TGG | ACG | TCG | CTC | AGC | AAC | CTG | GTG | GCC | TCC | CTG | CTC | AAC | TCC | 1743 |
| Lys | Tyr | Trp | Thr | Ser | Leu | Ser | Asn | Leu | Val | Ala | Ser | Leu | Leu | Asn | Ser | |
| 540 | | | | | 545 | | | | | 550 | | | | | 555 | |
| ATC | CGC | TCC | ATC | GCC | TCG | CTG | CTG | CTG | CTC | TTC | CTC | TTC | ATC | ATC | | 1791 |
| Ile | Arg | Ser | Ile | Ala | Ser | Leu | Leu | Leu | Leu | Phe | Leu | Phe | Ile | Ile | | |
| | | | | 560 | | | | | 565 | | | | | 570 | | |
| ATC | TTC | GCC | CTG | CTG | GGC | ATG | CAG | CTC | TTC | GGG | GGG | CGG | TAC | GAC | TTC | 1839 |
| Ile | Phe | Ala | Leu | Leu | Gly | Met | Gln | Leu | Phe | Gly | Gly | Arg | Tyr | Asp | Phe | |
| | | | | 575 | | | | | 580 | | | | | 585 | | |
| GAG | GAC | ACG | GAA | GTG | CGA | CGC | AGC | AAC | TTC | GAC | AAC | TTC | CCC | CAG | GCC | 1887 |
| Glu | Asp | Thr | Glu | Val | Arg | Arg | Ser | Asn | Phe | Asp | Asn | Phe | Pro | Gln | Ala | |
| | | | 590 | | | | | 595 | | | | | 600 | | | |
| CTC | ATC | AGC | GTC | TTC | CAG | GTG | CTG | ACG | GGT | GAG | GAC | TGG | AAC | TCC | GTG | 1935 |
| Leu | Ile | Ser | Val | Phe | Gln | Val | Leu | Thr | Gly | Glu | Asp | Trp | Asn | Ser | Val | |
| | 605 | | | | | 610 | | | | | 615 | | | | | |
| ATG | TAC | AAC | GGG | ATC | ATG | GCC | TAC | GGA | GGC | CCG | TCC | TAC | CCG | GGC | GTT | 1983 |
| Met | Tyr | Asn | Gly | Ile | Met | Ala | Tyr | Gly | Gly | Pro | Ser | Tyr | Pro | Gly | Val | |
| 620 | | | | | 625 | | | | | 630 | | | | | 635 | |
| CTC | GTG | TGC | ATC | TAT | TTC | ATC | ATC | CTT | TTT | GTC | TGC | GGC | AAC | TAT | ATC | 2031 |
| Leu | Val | Cys | Ile | Tyr | Phe | Ile | Ile | Leu | Phe | Val | Cys | Gly | Asn | Tyr | Ile | |
| | | | | 640 | | | | | 645 | | | | | 650 | | |
| CTG | CTG | AAT | GTC | TTC | CTG | GCC | ATC | GCC | GTG | GAC | AAC | CTG | GCC | GAG | GCC | 2079 |
| Leu | Leu | Asn | Val | Phe | Leu | Ala | Ile | Ala | Val | Asp | Asn | Leu | Ala | Glu | Ala | |
| | | | | 655 | | | | | 660 | | | | | 665 | | |
| GAG | AGC | CTG | ACT | TCC | GCG | CAA | AAG | GCC | AAG | GCC | GAG | GAG | AGG | AAA | CGT | 2127 |
| Glu | Ser | Leu | Thr | Ser | Ala | Gln | Lys | Ala | Lys | Ala | Glu | Glu | Arg | Lys | Arg | |
| | | 670 | | | | | 675 | | | | | 680 | | | | |
| AGG | AAG | ATG | TCC | AGG | GGT | CTC | CCT | GAC | AAG | ACG | GAG | GAG | GAG | AAG | TCT | 2175 |
| Arg | Lys | Met | Ser | Arg | Gly | Leu | Pro | Asp | Lys | Thr | Glu | Glu | Glu | Lys | Ser | |
| | 685 | | | | | 690 | | | | | 695 | | | | | |
| GTG | ATG | GCC | AAG | AAG | CTG | GAG | CAG | AAG | CCC | AAG | GGG | GAG | GGC | ATC | CCC | 2223 |
| Val | Met | Ala | Lys | Lys | Leu | Glu | Gln | Lys | Pro | Lys | Gly | Glu | Gly | Ile | Pro | |
| 700 | | | | | 705 | | | | | 710 | | | | | 715 | |
| ACC | ACT | GCC | AAG | CTC | AAG | GTC | GAT | GAG | TTC | GAA | TCT | AAC | GTC | AAC | GAG | 2271 |
| Thr | Thr | Ala | Lys | Leu | Lys | Val | Asp | Glu | Phe | Glu | Ser | Asn | Val | Asn | Glu | |
| | | | | 720 | | | | | 725 | | | | | 730 | | |
| GTG | AAG | GAC | CCC | TAC | CCT | TCA | GCT | GAC | TTC | CCA | GGG | GAT | GAT | GAG | GAG | 2319 |
| Val | Lys | Asp | Pro | Tyr | Pro | Ser | Ala | Asp | Phe | Pro | Gly | Asp | Asp | Glu | Glu | |
| | | | 735 | | | | | 740 | | | | | 745 | | | |
| GAC | GAG | CCT | GAG | ATC | CCA | GTG | AGC | CCC | CGA | CCG | CGC | CCG | CTG | GCC | GAG | 2367 |
| Asp | Glu | Pro | Glu | Ile | Pro | Val | Ser | Pro | Arg | Pro | Arg | Pro | Leu | Ala | Glu | |
| | | 750 | | | | | 755 | | | | | 760 | | | | |
| CTG | CAG | CTC | AAA | GAG | AAG | GCA | GTG | CCC | ATC | CCG | GAA | GCC | AGC | TCC | TTC | 2415 |
| Leu | Gln | Leu | Lys | Glu | Lys | Ala | Val | Pro | Ile | Pro | Glu | Ala | Ser | Ser | Phe | |
| | 765 | | | | | 770 | | | | | 775 | | | | | |
| TTC | ATC | TTC | AGT | CCC | ACC | AAT | AAG | GTC | CGT | GTC | CTG | TGT | CAC | CGC | ATC | 2463 |
| Phe | Ile | Phe | Ser | Pro | Thr | Asn | Lys | Val | Arg | Val | Leu | Cys | His | Arg | Ile | |
| 780 | | | | | 785 | | | | | 790 | | | | | 795 | |
| GTC | AAC | GCC | ACC | TGG | TTC | ACC | AAC | TTC | ATC | CTG | CTC | TTC | ATC | CTG | CTC | 2511 |
| Val | Asn | Ala | Thr | Trp | Phe | Thr | Asn | Phe | Ile | Leu | Leu | Phe | Ile | Leu | Leu | |
| | | | | 800 | | | | | 805 | | | | | 810 | | |
| AGC | AGT | GCT | GCG | CTG | GCC | GCC | GAG | GAC | CCC | ATC | CGG | GCG | GAG | TCC | GTG | 2559 |
| Ser | Ser | Ala | Ala | Leu | Ala | Ala | Glu | Asp | Pro | Ile | Arg | Ala | Glu | Ser | Val | |
| | | | | 815 | | | | | 820 | | | | | 825 | | |
| AGG | AAT | CAG | ATC | CTT | GGA | TAT | TTT | GAT | ATT | GCC | TTC | ACC | TCT | GTC | TTC | 2607 |
| Arg | Asn | Gln | Ile | Leu | Gly | Tyr | Phe | Asp | Ile | Ala | Phe | Thr | Ser | Val | Phe | |
| | | | | 830 | | | | | 835 | | | | | 840 | | |
| ACT | GTG | GAG | ATT | GTC | CTC | AAG | ATG | ACA | ACC | TAC | GGC | GCC | TTC | CTG | CAC | 2655 |

```
        Thr Val Glu Ile Val Leu Lys Met Thr Thr Tyr Gly Ala Phe Leu His
            845                 850                 855

AAG GGC TCC TTC TGC CGC AAC TAC TTC AAC ATC CTG GAC CTG CTG GTG        2703
Lys Gly Ser Phe Cys Arg Asn Tyr Phe Asn Ile Leu Asp Leu Leu Val
860                 865                 870                 875

GTG GCC GTG TCT CTC ATC TCC ATG GGT CTC GAG TCC AGC ACC ATC TCC        2751
Val Ala Val Ser Leu Ile Ser Met Gly Leu Glu Ser Ser Thr Ile Ser
                880                 885                 890

GTG GTA AAG ATC CTG AGA GTG CTA AGG GTG CTC CGG CCC CTG CGA GCC        2799
Val Val Lys Ile Leu Arg Val Leu Arg Val Leu Arg Pro Leu Arg Ala
            895                 900                 905

ATC AAC AGA GCC AAA GGG TTG AAG CAC GTG GTC CAG TGC GTG TTC GTG        2847
Ile Asn Arg Ala Lys Gly Leu Lys His Val Val Gln Cys Val Phe Val
        910                 915                 920

GCC ATC CGC ACC ATC GGG AAC ATC GTC CTG GTC ACC ACG CTC CTG CAG        2895
Ala Ile Arg Thr Ile Gly Asn Ile Val Leu Val Thr Thr Leu Leu Gln
    925                 930                 935

TTC ATG TTC GCC TGC ATC GGT GTC CAG CTC TTC AAG GGC AAG TTC TTC        2943
Phe Met Phe Ala Cys Ile Gly Val Gln Leu Phe Lys Gly Lys Phe Phe
940                 945                 950                 955

AGC TGC AAT GAC CTA TCC AAG ATG ACA GAA GAG GAG TGC AGG GGC TAC        2991
Ser Cys Asn Asp Leu Ser Lys Met Thr Glu Glu Glu Cys Arg Gly Tyr
                960                 965                 970

TAC TAT GTG TAC AAG GAC GGG GAC CCC ACG CAG ATG GAG CTG CGC CCC        3039
Tyr Tyr Val Tyr Lys Asp Gly Asp Pro Thr Gln Met Glu Leu Arg Pro
            975                 980                 985

CGC CAG TGG ATA CAC AAT GAC TTC CAC TTT GAC AAC GTG CTG TCG GCC        3087
Arg Gln Trp Ile His Asn Asp Phe His Phe Asp Asn Val Leu Ser Ala
        990                 995                 1000

ATG ATG TCG CTC TTC ACG GTG TCC ACC TTC GAG GGA TGG CCC CAG CTG        3135
Met Met Ser Leu Phe Thr Val Ser Thr Phe Glu Gly Trp Pro Gln Leu
    1005                1010                1015

CTG TAC AGG GCC ATA GAC TCC AAC GAG GAG GAC ATG GGC CCC GTT TAC        3183
Leu Tyr Arg Ala Ile Asp Ser Asn Glu Glu Asp Met Gly Pro Val Tyr
1020                1025                1030                1035

AAC AAC CGA GTG GAG ATG GCC ATC TTC TTC ATC ATC TAC ATC ATC CTC        3231
Asn Asn Arg Val Glu Met Ala Ile Phe Phe Ile Ile Tyr Ile Ile Leu
                1040                1045                1050

ATT GCC TTC TTC ATG ATG AAC ATC TTT GTG GGC TTT GTC ATC GTC ACC        3279
Ile Ala Phe Phe Met Met Asn Ile Phe Val Gly Phe Val Ile Val Thr
            1055                1060                1065

TTC CAG GAG CAG GGG GAG ACG GAG TAC AAG AAC TGC GAG CTG GAC AAG        3327
Phe Gln Glu Gln Gly Glu Thr Glu Tyr Lys Asn Cys Glu Leu Asp Lys
        1070                1075                1080

AAC CAG CGC CAG TGT GTG CAG TAT GCC CTG AAG GCC CGC CCA CTT CGG        3375
Asn Gln Arg Gln Cys Val Gln Tyr Ala Leu Lys Ala Arg Pro Leu Arg
    1085                1090                1095

TGC TAC ATC CCC AAG AAC CCA TAC CAG TAC CAG GTG TGG TAC GTC GTC        3423
Cys Tyr Ile Pro Lys Asn Pro Tyr Gln Tyr Gln Val Trp Tyr Val Val
1100                1105                1110                1115

ACC TCC TCC TAC TTT GAA TAC CTG ATG TTC GCC CTC ATC ATG CTC AAC        3471
Thr Ser Ser Tyr Phe Glu Tyr Leu Met Phe Ala Leu Ile Met Leu Asn
                1120                1125                1130

ACC ATC TGC CTG GGC ATG CAG CAC TAC CAC CAG TCG GAG GAG ATG AAC        3519
Thr Ile Cys Leu Gly Met Gln His Tyr His Gln Ser Glu Glu Met Asn
            1135                1140                1145

CAC ATC TCA GAC ATC CTC AAT GTG GCC TTC ACC ATC ATC TTC ACG CTG        3567
His Ile Ser Asp Ile Leu Asn Val Ala Phe Thr Ile Ile Phe Thr Leu
        1150                1155                1160

GAG ATG ATT CTC AAG CTC TTG GCG TTC AAG GCC AGG GGC TAT TTC GGA        3615
```

| | | | | | | | | | | | | | | | | |
|---|---|---|---|---|---|---|---|---|---|---|---|---|---|---|---|---|
| Glu | Met | Ile | Leu | Lys | Leu | Leu | Ala | Phe | Lys | Ala | Arg | Gly | Tyr | Phe | Gly | |
| | 1165 | | | | 1170 | | | | | 1175 | | | | | | |
| GAC | CCC | TGG | AAT | GTG | TTC | GAC | TTC | CTG | ATC | GTC | ATC | GGC | AGC | ATC | ATT | 3663 |
| Asp | Pro | Trp | Asn | Val | Phe | Asp | Phe | Leu | Ile | Val | Ile | Gly | Ser | Ile | Ile | |
| 1180 | | | | | 1185 | | | | | 1190 | | | | | 1195 | |
| GAC | GTC | ATC | CTC | AGC | GAG | ATC | GAC | ACT | TTC | CTG | GCC | TCC | AGC | GGG | GGA | 3711 |
| Asp | Val | Ile | Leu | Ser | Glu | Ile | Asp | Thr | Phe | Leu | Ala | Ser | Ser | Gly | Gly | |
| | | | | 1200 | | | | | 1205 | | | | | 1210 | | |
| CTG | TAT | TGC | CTG | GGT | GGC | GGC | TGC | GGG | AAC | GTT | GAC | CCA | GAC | GAG | AGC | 3759 |
| Leu | Tyr | Cys | Leu | Gly | Gly | Gly | Cys | Gly | Asn | Val | Asp | Pro | Asp | Glu | Ser | |
| | | | 1215 | | | | | 1220 | | | | | 1225 | | | |
| GCC | CGC | ATC | TCC | AGT | GCC | TTC | TTC | CGC | CTG | TTC | CGG | GTT | ATG | AGG | CTG | 3807 |
| Ala | Arg | Ile | Ser | Ser | Ala | Phe | Phe | Arg | Leu | Phe | Arg | Val | Met | Arg | Leu | |
| | | 1230 | | | | | 1235 | | | | | 1240 | | | | |
| ATC | AAG | CTG | CTG | AGT | CGG | GCC | GAG | GGC | GTG | CGC | ACG | CTG | CTG | TGG | ACG | 3855 |
| Ile | Lys | Leu | Leu | Ser | Arg | Ala | Glu | Gly | Val | Arg | Thr | Leu | Leu | Trp | Thr | |
| 1245 | | | | | 1250 | | | | | 1255 | | | | | | |
| TTC | ATC | AAG | TCC | TTC | CAG | GCC | CTG | CCC | TAC | GTG | GCC | CTG | CTC | ATC | GTC | 3903 |
| Phe | Ile | Lys | Ser | Phe | Gln | Ala | Leu | Pro | Tyr | Val | Ala | Leu | Leu | Ile | Val | |
| 1260 | | | | | 1265 | | | | | 1270 | | | | | 1275 | |
| ATG | CTG | TTC | TTC | ATC | TAC | GCC | GTC | ATC | GGC | ATG | CAG | ATG | TTT | GGA | AAG | 3951 |
| Met | Leu | Phe | Phe | Ile | Tyr | Ala | Val | Ile | Gly | Met | Gln | Met | Phe | Gly | Lys | |
| | | | | 1280 | | | | | 1285 | | | | | 1290 | | |
| ATC | GCC | CTG | GTG | GAC | GGG | ACC | CAG | ATC | AAC | CGC | AAC | AAC | AAC | TTC | CAG | 3999 |
| Ile | Ala | Leu | Val | Asp | Gly | Thr | Gln | Ile | Asn | Arg | Asn | Asn | Asn | Phe | Gln | |
| | | | 1295 | | | | | 1300 | | | | | 1305 | | | |
| ACC | TTC | CCG | CAG | GCC | GTG | CTG | CTG | CTC | TTC | AGG | TGT | GCG | ACA | GGG | GAG | 4047 |
| Thr | Phe | Pro | Gln | Ala | Val | Leu | Leu | Leu | Phe | Arg | Cys | Ala | Thr | Gly | Glu | |
| | | 1310 | | | | | 1315 | | | | | 1320 | | | | |
| GCG | TGG | CAA | GAG | ATC | CTG | CTG | GCC | TGC | AGC | TAC | GGG | AAG | TTG | TGC | GAC | 4095 |
| Ala | Trp | Gln | Glu | Ile | Leu | Leu | Ala | Cys | Ser | Tyr | Gly | Lys | Leu | Cys | Asp | |
| | 1325 | | | | | 1330 | | | | | 1335 | | | | | |
| CCA | GAG | TCA | GAC | TAC | GCC | CCG | GGC | GAG | GAG | TAC | ACG | TGT | GGC | ACC | AAC | 4143 |
| Pro | Glu | Ser | Asp | Tyr | Ala | Pro | Gly | Glu | Glu | Tyr | Thr | Cys | Gly | Thr | Asn | |
| 1340 | | | | | 1345 | | | | | 1350 | | | | | 1355 | |
| TTC | GCC | TAC | TAC | TAC | TTC | ATC | AGC | TTC | TAC | ATG | CTC | TGC | GCC | TTC | CTG | 4191 |
| Phe | Ala | Tyr | Tyr | Tyr | Phe | Ile | Ser | Phe | Tyr | Met | Leu | Cys | Ala | Phe | Leu | |
| | | | | 1360 | | | | | 1365 | | | | | 1370 | | |
| ATC | ATC | AAC | CTC | TTC | GTG | GCT | GTC | ATC | ATG | GAC | AAC | TTT | GAC | TAC | CTG | 4239 |
| Ile | Ile | Asn | Leu | Phe | Val | Ala | Val | Ile | Met | Asp | Asn | Phe | Asp | Tyr | Leu | |
| | | | 1375 | | | | | 1380 | | | | | 1385 | | | |
| ACA | CGC | GAC | TGG | TCC | ATC | CTG | GGC | CCT | CAC | CAC | CTG | GAC | GAG | TTC | AAG | 4287 |
| Thr | Arg | Asp | Trp | Ser | Ile | Leu | Gly | Pro | His | His | Leu | Asp | Glu | Phe | Lys | |
| | | 1390 | | | | | 1395 | | | | | 1400 | | | | |
| GCC | ATC | TGG | GCA | GAG | TAT | GAC | CCA | GAG | GCC | AAG | GGG | CGA | ATC | AAG | CAC | 4335 |
| Ala | Ile | Trp | Ala | Glu | Tyr | Asp | Pro | Glu | Ala | Lys | Gly | Arg | Ile | Lys | His | |
| | 1405 | | | | | 1410 | | | | | 1415 | | | | | |
| CTG | GAC | GTG | GTG | ACC | CTG | CTG | AGA | AGG | ATC | CAG | CCC | CCT | CTG | GGC | TTC | 4383 |
| Leu | Asp | Val | Val | Thr | Leu | Leu | Arg | Arg | Ile | Gln | Pro | Pro | Leu | Gly | Phe | |
| 1420 | | | | | 1425 | | | | | 1430 | | | | | 1435 | |
| GGG | AAG | TTC | TGT | CCA | CAC | CGG | GTG | GCC | TGT | AAG | CGC | CTG | GTG | GGC | ATG | 4431 |
| Gly | Lys | Phe | Cys | Pro | His | Arg | Val | Ala | Cys | Lys | Arg | Leu | Val | Gly | Met | |
| | | | | 1440 | | | | | 1445 | | | | | 1450 | | |
| AAC | ATG | CCC | CTG | AAC | AGT | GAC | GGC | ACG | GTC | ACC | TTC | AAT | GCC | ACG | CTC | 4479 |
| Asn | Met | Pro | Leu | Asn | Ser | Asp | Gly | Thr | Val | Thr | Phe | Asn | Ala | Thr | Leu | |
| | | | 1455 | | | | | 1460 | | | | | 1465 | | | |
| TTT | GCC | CTG | GTG | CGC | ACG | GCC | CTC | AAG | ATC | AAG | ACA | GAA | GGT | AAC | TTC | 4527 |
| Phe | Ala | Leu | Val | Arg | Thr | Ala | Leu | Lys | Ile | Lys | Thr | Glu | Gly | Asn | Phe | |
| | | 1470 | | | | | 1475 | | | | | 1480 | | | | |
| GAG | CAG | GCC | AAC | GAG | GAG | CTG | AGG | GCC | ATC | ATC | AAG | AAG | ATC | TGG | AAG | 4575 |

```
        Glu Gln Ala Asn Glu Glu Leu Arg Ala Ile Ile Lys Lys Ile Trp Lys
            1485                1490                1495

AGA ACC AGC ATG AAG CTA CTG GAC CAG GTC ATC CCT CCC ATA GGA GAT             4623
Arg Thr Ser Met Lys Leu Leu Asp Gln Val Ile Pro Pro Ile Gly Asp
1500                1505                1510                1515

GAC GAG GTG ACC GTG GGG AAG TTC TAC GCC ACA TTC CTC ATC CAG GAG             4671
Asp Glu Val Thr Val Gly Lys Phe Tyr Ala Thr Phe Leu Ile Gln Glu
                1520                1525                1530

CAC TTC CGG AAG TTC ATG AAG CGC CAG GAG GAA TAT TAT GGG TAT CGG             4719
His Phe Arg Lys Phe Met Lys Arg Gln Glu Glu Tyr Tyr Gly Tyr Arg
        1535                1540                1545

CCC AAG AAG GAC ACC GTG CAG ATC CAG GCT GGG CTG CGG ACC ATA GAG             4767
Pro Lys Lys Asp Thr Val Gln Ile Gln Ala Gly Leu Arg Thr Ile Glu
            1550                1555                1560

GAG GAG GCG GCC CCT GAG ATC CGC CGC ACC ATC TCA GGA GAC CTG ACC             4815
Glu Glu Ala Ala Pro Glu Ile Arg Arg Thr Ile Ser Gly Asp Leu Thr
1565                1570                1575

GCC GAG GAG GAG CTG GAG AGA GCC ATG GTG GAG GCT GCG ATG GAG GAG             4863
Ala Glu Glu Glu Leu Glu Arg Ala Met Val Glu Ala Ala Met Glu Glu
1580                1585                1590                1595

AGG ATC TTC CGG AGG ACC GGA GGC CTG TTT GGC CAG GTG GAC ACC TTC             4911
Arg Ile Phe Arg Arg Thr Gly Gly Leu Phe Gly Gln Val Asp Thr Phe
                1600                1605                1610

CTG GAA AGG ACC AAC TCC CTA CCC CCG GTG ATG GCC AAC CAA AGA CCG             4959
Leu Glu Arg Thr Asn Ser Leu Pro Pro Val Met Ala Asn Gln Arg Pro
        1615                1620                1625

CTC CAG TTT GCT GAG ATA GAA ATG GAA GAG CTT GAG TCG CCT GTC TTC             5007
Leu Gln Phe Ala Glu Ile Glu Met Glu Glu Leu Glu Ser Pro Val Phe
            1630                1635                1640

TTG GAG GAC TTC CCT CAA GAC GCA AGA ACC AAC CCT CTC GCT CGT GCC             5055
Leu Glu Asp Phe Pro Gln Asp Ala Arg Thr Asn Pro Leu Ala Arg Ala
1645                1650                1655

AAT ACC AAC AAC GCC AAT GCC AAT GTT GCC TAT GGC AAC AGC AAC CAT             5103
Asn Thr Asn Asn Ala Asn Ala Asn Val Ala Tyr Gly Asn Ser Asn His
1660                1665                1670                1675

AGC AAC AAC CAG ATG TTT TCC AGC GTC CAC TGT GAA AGG GAG TTC CCG             5151
Ser Asn Asn Gln Met Phe Ser Ser Val His Cys Glu Arg Glu Phe Pro
                1680                1685                1690

GGA GAG GCG GAG ACA CCG GCT GCC GGA CGA GGA GCC CTC AGC CAC TCC             5199
Gly Glu Ala Glu Thr Pro Ala Ala Gly Arg Gly Ala Leu Ser His Ser
        1695                1700                1705

CAC AGG GCC CTG GGA CCT CAC AGC AAG CCC TGT GCT GGA AAA CTG AAT             5247
His Arg Ala Leu Gly Pro His Ser Lys Pro Cys Ala Gly Lys Leu Asn
            1710                1715                1720

GGG CAG CTG GTC CAG CCG GGA ATG CCC ATC AAC CAG GCA CCT CCT GCC             5295
Gly Gln Leu Val Gln Pro Gly Met Pro Ile Asn Gln Ala Pro Pro Ala
1725                1730                1735

CCC TGC CAG CAG CCT AGC ACA GAT CCC CCA GAG CGC GGG CAG AGG AGG             5343
Pro Cys Gln Gln Pro Ser Thr Asp Pro Pro Glu Arg Gly Gln Arg Arg
1740                1745                1750                1755

ACC TCC CTG ACA GGG TCT CTG CAA GAC GAA GCA CCC CAG AGG AGG AGC             5391
Thr Ser Leu Thr Gly Ser Leu Gln Asp Glu Ala Pro Gln Arg Arg Ser
                1760                1765                1770

TCC GAG GGG AGC ACC CCC AGG CGC CCG GCT CCT GCT ACA GCT CTG CTG             5439
Ser Glu Gly Ser Thr Pro Arg Arg Pro Ala Pro Ala Thr Ala Leu Leu
        1775                1780                1785

ATC CAA GAG GCT CTG GTT CGA GGG GGC CTG GAC ACC TTG GCA GCT GAT             5487
Ile Gln Glu Ala Leu Val Arg Gly Gly Leu Asp Thr Leu Ala Ala Asp
            1790                1795                1800

GCT GGC TTC GTC ATG GCA ACA AGC CAG GCC CTG GTA GAC GCC TGT CAG             5535
```

| | | | | | | | | | | | | | | | |
|---|---|---|---|---|---|---|---|---|---|---|---|---|---|---|---|
| Ala | Gly | Phe | Val | Met | Ala | Thr | Ser | Gln | Ala | Leu | Val | Asp | Ala | Cys | Gln |
| | 1805 | | | | 1810 | | | | | 1815 | | | | | |

| ATG | GAA | CCG | GAG | GAA | GTA | GAG | GTC | GCA | GCC | ACA | GAG | CTA | CTG | AAA | GAG | 5583 |
|---|---|---|---|---|---|---|---|---|---|---|---|---|---|---|---|---|
| Met | Glu | Pro | Glu | Glu | Val | Glu | Val | Ala | Ala | Thr | Glu | Leu | Leu | Lys | Glu | |
| 1820 | | | | | 1825 | | | | 1830 | | | | | | 1835 | |

| CGA | GAG | TCC | GTC | CAG | GGC | ATG | GCC | AGT | GTC | CCG | GGA | AGC | CTG | AGC | CGC | 5631 |
|---|---|---|---|---|---|---|---|---|---|---|---|---|---|---|---|---|
| Arg | Glu | Ser | Val | Gln | Gly | Met | Ala | Ser | Val | Pro | Gly | Ser | Leu | Ser | Arg | |
| | | | | 1840 | | | | | 1845 | | | | | 1850 | | |

| AGG | TCC | TCC | CTG | GGC | AGC | CTT | GAC | CAG | GTC | CAG | GGC | TCC | CAG | GAA | ACC | 5679 |
|---|---|---|---|---|---|---|---|---|---|---|---|---|---|---|---|---|
| Arg | Ser | Ser | Leu | Gly | Ser | Leu | Asp | Gln | Val | Gln | Gly | Ser | Gln | Glu | Thr | |
| | | | 1855 | | | | | 1860 | | | | | 1865 | | | |

| CTT | ATT | CCT | CCC | AGG | CCG | TGA | TGGCTGTGCA | GTGTCCACAT | GACCAAGGCG | AGGGG | 5735 |
|---|---|---|---|---|---|---|---|---|---|---|---|
| Leu | Ile | Pro | Pro | Arg | Pro | * | | | | | |
| | | 1870 | | | | | | | | | |

| GACAGTGCGT | GCAGAAGCTC | AGCCCTGCAT | GGCAGCCTCC | CTCTGTCTCA | GCCCTCCTGC | 5795 |
|---|---|---|---|---|---|---|
| TGAGCTGGGG | CGGTCTGGAA | CCGACCAGGA | AGCCAGGAGC | CTCCCTGGC | CAGCAAGAGG | 5855 |
| CATGATTCTA | AAGCATCCAG | AAAGGCCTGG | TCAGTGCCAC | TCCCCAGCAG | GACATTAAAG | 5915 |
| TCTCTAGGTC | TGTGGCAAAA | AAAAAAAAAA | AAAAAAAAAA | AAAAAAAAAA | AAAAAAAAAA | 5975 |

( 2 ) INFORMATION FOR SEQ ID NO:2:

( i ) SEQUENCE CHARACTERISTICS:
        ( A ) LENGTH: 3802 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: Coding Sequence
        ( B ) LOCATION: 309...3630
        ( A ) NAME/KEY: mat_peptide
        ( B ) LOCATION: 387...3626
        ( D ) OTHER INFORMATION:

( x i ) SEQUENCE DESCRIPTION: SEQ ID NO:2:

| AGAAGGGAGG | GCGAGCGTGG | TGTGTGCGCG | CTCGGGCGCC | GGCGGCACCG | CCGAGGTCTG | 60 |
|---|---|---|---|---|---|---|
| TTGGCAAAAG | TCGCCCTTGA | TGGCGGCGGA | GGCGAGGCAG | CCGCGGCGCC | GAACAGCCGA | 120 |
| CGCGCGCTAG | CGGGGTCCGC | CCGCCCCTTT | CCAGAGCCC | AGCGCCGCCG | TTCGCCGCCG | 180 |
| CCGCCGCCCG | CCCGCGCGCC | GTTCGCCGCC | GCCGCCGCCC | GCGGGTGGCA | GCGCCGCTCG | 240 |
| GTCCCCGGCC | CCGGGGCCGG | CTGGGGGGCG | GTCGGGCGT | GTGAGGGGCT | TGCTCCCAGC | 300 |

| TCGCGAAG | ATG | GCT | GCG | GGC | CGC | CCG | CTG | GCC | TGG | ACG | CTG | ACA | CTT | TGG | 350 |
|---|---|---|---|---|---|---|---|---|---|---|---|---|---|---|---|
| | Met | Ala | Ala | Gly | Arg | Pro | Leu | Ala | Trp | Thr | Leu | Thr | Leu | Trp | |
| | -26 | -25 | | | | -20 | | | | | -15 | | | | |

| CAG | GCG | TGG | CTG | ATC | CTG | ATC | GGG | CCC | TCG | TCG | GAG | GAG | CCG | TTC | CCT | 398 |
|---|---|---|---|---|---|---|---|---|---|---|---|---|---|---|---|---|
| Gln | Ala | Trp | Leu | Ile | Leu | Ile | Gly | Pro | Ser | Ser | Glu | Glu | Pro | Phe | Pro | |
| | -10 | | | | | -5 | | | | | -1 | 1 | | | | |

| TCA | GCC | GTC | ACT | ATC | AAG | TCA | TGG | GTG | GAT | AAG | ATG | CAA | GAA | GAC | CTG | 446 |
|---|---|---|---|---|---|---|---|---|---|---|---|---|---|---|---|---|
| Ser | Ala | Val | Thr | Ile | Lys | Ser | Trp | Val | Asp | Lys | Met | Gln | Glu | Asp | Leu | |
| 5 | | | | | 10 | | | | | 15 | | | | | 20 | |

| GTC | ACA | CTG | GCA | AAA | ACA | GCA | AGT | GGA | GTC | AAT | CAG | CTT | GTT | GAT | ATT | 494 |
|---|---|---|---|---|---|---|---|---|---|---|---|---|---|---|---|---|
| Val | Thr | Leu | Ala | Lys | Thr | Ala | Ser | Gly | Val | Asn | Gln | Leu | Val | Asp | Ile | |
| | | | | 25 | | | | | 30 | | | | | 35 | | |

| TAT | GAG | AAA | TAT | CAA | GAT | TTG | TAT | ACT | GTG | GAA | CCA | AAT | AAT | GCA | CGT | 542 |
|---|---|---|---|---|---|---|---|---|---|---|---|---|---|---|---|---|
| Tyr | Glu | Lys | Tyr | Gln | Asp | Leu | Tyr | Thr | Val | Glu | Pro | Asn | Asn | Ala | Arg | |
| | | | 40 | | | | | 45 | | | | | 50 | | | |

| CAG | CTG | GTG | GAA | ATT | GCA | GCC | AGA | GAC | ATT | GAG | AAG | CTT | CTC | AGC | AAC | 590 |
|---|---|---|---|---|---|---|---|---|---|---|---|---|---|---|---|---|
| Gln | Leu | Val | Glu | Ile | Ala | Ala | Arg | Asp | Ile | Glu | Lys | Leu | Leu | Ser | Asn | |
| | | 55 | | | | | 60 | | | | | 65 | | | | |

```
AGA TCT AAA GCC CTG GTG CGC CTG GCT TTG GAA GCA GAG AAA GTT CAA        638
Arg Ser Lys Ala Leu Val Arg Leu Ala Leu Glu Ala Glu Lys Val Gln
    70              75              80

GCA GCC CAC CAA TGG AGG GAA GAT TTT GCA AGC AAT GAA GTT GTC TAC        686
Ala Ala His Gln Trp Arg Glu Asp Phe Ala Ser Asn Glu Val Val Tyr
85              90              95              100

TAT AAC GCG AAG GAT GAT CTT GAT CCT GAA AAA AAT GAC AGT GAA CCA        734
Tyr Asn Ala Lys Asp Asp Leu Asp Pro Glu Lys Asn Asp Ser Glu Pro
                105             110             115

GGC AGC CAG AGG ATC AAA CCT GTT TTC ATT GAC GAT GCT AAC TTT AGA        782
Gly Ser Gln Arg Ile Lys Pro Val Phe Ile Asp Asp Ala Asn Phe Arg
            120             125             130

AGA CAA GTA TCC TAT CAG CAC GCA GCT GTC CAT ATC CCC ACT GAC ATC        830
Arg Gln Val Ser Tyr Gln His Ala Ala Val His Ile Pro Thr Asp Ile
        135             140             145

TAT GAA GGA TCG ACA ATC GTG TTA AAC GAA CTC AAC TGG ACA AGT GCC        878
Tyr Glu Gly Ser Thr Ile Val Leu Asn Glu Leu Asn Trp Thr Ser Ala
150             155             160

TTA GAT GAC GTT TTC AAA AAA AAT CGA GAG GAA GAC CCT TCA CTG TTG        926
Leu Asp Asp Val Phe Lys Lys Asn Arg Glu Glu Asp Pro Ser Leu Leu
165             170             175             180

TGG CAG GTG TTT GGC AGT GCC ACT GGC CTG GCC CGG TAT TAC CCA GCT        974
Trp Gln Val Phe Gly Ser Ala Thr Gly Leu Ala Arg Tyr Tyr Pro Ala
                185             190             195

TCT CCA TGG GTT GAT AAT AGC CGA ACC CCA AAC AAG ATT GAT CTT TAT       1022
Ser Pro Trp Val Asp Asn Ser Arg Thr Pro Asn Lys Ile Asp Leu Tyr
            200             205             210

GAT GTA CGC AGA AGA CCA TGG TAC ATC CAA GGT GCT GCA TCC CCT AAA       1070
Asp Val Arg Arg Arg Pro Trp Tyr Ile Gln Gly Ala Ala Ser Pro Lys
        215             220             225

GAT ATG CTT ATT CTG GTG GAT GTG AGT GGA AGC GTT AGT GGA CTG ACA       1118
Asp Met Leu Ile Leu Val Asp Val Ser Gly Ser Val Ser Gly Leu Thr
230             235             240

CTC AAA CTC ATC CGG ACA TCC GTC TCC GAA ATG TTG GAA ACC CTC TCA       1166
Leu Lys Leu Ile Arg Thr Ser Val Ser Glu Met Leu Glu Thr Leu Ser
245             250             255             260

GAT GAT GAT TTT GTG AAC GTG GCT TCA TTT AAC AGC AAT GCT CAG GAT       1214
Asp Asp Asp Phe Val Asn Val Ala Ser Phe Asn Ser Asn Ala Gln Asp
                265             270             275

GTA AGC TGC TTT CAG CAC CTT GTC CAA GCA AAT GTA AGA AAT AAG AAA       1262
Val Ser Cys Phe Gln His Leu Val Gln Ala Asn Val Arg Asn Lys Lys
            280             285             290

GTG TTG AAA GAT GCA GTG AAT AAT ATC ACA GCA AAA GGA ATC ACA GAT       1310
Val Leu Lys Asp Ala Val Asn Asn Ile Thr Ala Lys Gly Ile Thr Asp
        295             300             305

TAT AAG AAG GGC TTT AGT TTT GCT TTT GAG CAG CTG CTT AAT TAT AAT       1358
Tyr Lys Lys Gly Phe Ser Phe Ala Phe Glu Gln Leu Leu Asn Tyr Asn
310             315             320

GTA TCC AGA GCC AAC TGC AAT AAG ATT ATC ATG TTG TTC ACG GAC GGA       1406
Val Ser Arg Ala Asn Cys Asn Lys Ile Ile Met Leu Phe Thr Asp Gly
325             330             335             340

GGA GAA GAG AGA GCC CAG GAG ATA TTT GCC AAA TAC AAT AAA GAC AAG       1454
Gly Glu Glu Arg Ala Gln Glu Ile Phe Ala Lys Tyr Asn Lys Asp Lys
                345             350             355

AAA GTA CGT GTA TTC ACA TTC TCA GTT GGC CAA CAT AAT TAC GAC AGA       1502
Lys Val Arg Val Phe Thr Phe Ser Val Gly Gln His Asn Tyr Asp Arg
            360             365             370

GGA CCT ATT CAG TGG ATG GCT TGC GAA AAT AAA GGT TAT TAT TAT GAA       1550
Gly Pro Ile Gln Trp Met Ala Cys Glu Asn Lys Gly Tyr Tyr Tyr Glu
        375             380             385
```

-continued

| | | | | | | | | | | | | | | | | |
|---|---|---|---|---|---|---|---|---|---|---|---|---|---|---|---|---|
| ATT | CCA | TCC | ATT | GGA | GCC | ATA | AGA | ATT | AAT | ACT | CAG | GAA | TAC | CTA | GAT | 1598 |
| Ile | Pro | Ser | Ile | Gly | Ala | Ile | Arg | Ile | Asn | Thr | Gln | Glu | Tyr | Leu | Asp | |
| | 390 | | | | 395 | | | | | 400 | | | | | | |
| GTT | CTG | GGA | AGA | CCG | ATG | GTT | TTA | GCA | GGA | GAC | AAA | GCT | AAG | CAA | GTC | 1646 |
| Val | Leu | Gly | Arg | Pro | Met | Val | Leu | Ala | Gly | Asp | Lys | Ala | Lys | Gln | Val | |
| 405 | | | | | 410 | | | | | 415 | | | | | 420 | |
| CAA | TGG | ACA | AAT | GTG | TAC | CTG | GAT | GCA | CTG | GAA | CTG | GGA | CTT | GTC | ATT | 1694 |
| Gln | Trp | Thr | Asn | Val | Tyr | Leu | Asp | Ala | Leu | Glu | Leu | Gly | Leu | Val | Ile | |
| | | | | 425 | | | | | 430 | | | | | 435 | | |
| ACT | GGA | ACT | CTT | CCG | GTC | TTC | AAC | ATA | ACT | GGC | CAA | TTT | GAA | AAT | AAG | 1742 |
| Thr | Gly | Thr | Leu | Pro | Val | Phe | Asn | Ile | Thr | Gly | Gln | Phe | Glu | Asn | Lys | |
| | | | 440 | | | | | 445 | | | | | 450 | | | |
| ACA | AAC | TTA | AAG | AAC | CAG | CTG | ATT | CTT | GGA | GTG | ATG | GGA | GTT | GAT | GTG | 1790 |
| Thr | Asn | Leu | Lys | Asn | Gln | Leu | Ile | Leu | Gly | Val | Met | Gly | Val | Asp | Val | |
| | | 455 | | | | 460 | | | | | 465 | | | | | |
| TCT | TTG | GAA | GAT | ATT | AAA | AGA | CTG | ACA | CCA | CGT | TTT | ACA | CTC | TGC | CCC | 1838 |
| Ser | Leu | Glu | Asp | Ile | Lys | Arg | Leu | Thr | Pro | Arg | Phe | Thr | Leu | Cys | Pro | |
| | 470 | | | | 475 | | | | | 480 | | | | | | |
| AAT | GGC | TAC | TAT | TTT | GCA | ATT | GAT | CCT | AAT | GGT | TAT | GTG | TTA | TTA | CAT | 1886 |
| Asn | Gly | Tyr | Tyr | Phe | Ala | Ile | Asp | Pro | Asn | Gly | Tyr | Val | Leu | Leu | His | |
| 485 | | | | | 490 | | | | | 495 | | | | | 500 | |
| CCA | AAT | CTT | CAG | CCA | AAG | CCT | ATT | GGT | GTA | GGT | ATA | CCA | ACA | ATT | AAT | 1934 |
| Pro | Asn | Leu | Gln | Pro | Lys | Pro | Ile | Gly | Val | Gly | Ile | Pro | Thr | Ile | Asn | |
| | | | | 505 | | | | | 510 | | | | | 515 | | |
| TTG | AGA | AAA | AGG | AGA | CCC | AAT | GTT | CAG | AAC | CCC | AAA | TCT | CAG | GAG | CCA | 1982 |
| Leu | Arg | Lys | Arg | Arg | Pro | Asn | Val | Gln | Asn | Pro | Lys | Ser | Gln | Glu | Pro | |
| | | | 520 | | | | | 525 | | | | | 530 | | | |
| GTG | ACA | TTG | GAT | TTC | CTC | GAT | GCA | GAG | TTG | GAG | AAT | GAC | ATT | AAA | GTG | 2030 |
| Val | Thr | Leu | Asp | Phe | Leu | Asp | Ala | Glu | Leu | Glu | Asn | Asp | Ile | Lys | Val | |
| | | 535 | | | | 540 | | | | | 545 | | | | | |
| GAG | ATT | CGA | AAT | AAA | ATG | ATC | GAT | GGA | GAA | AGT | GGA | GAA | AAA | ACA | TTC | 2078 |
| Glu | Ile | Arg | Asn | Lys | Met | Ile | Asp | Gly | Glu | Ser | Gly | Glu | Lys | Thr | Phe | |
| 550 | | | | | 555 | | | | | 560 | | | | | | |
| AGA | ACT | CTG | GTT | AAA | TCT | CAA | GAT | GAG | AGA | TAT | ATT | GAC | AAA | GGA | AAC | 2126 |
| Arg | Thr | Leu | Val | Lys | Ser | Gln | Asp | Glu | Arg | Tyr | Ile | Asp | Lys | Gly | Asn | |
| 565 | | | | | 570 | | | | | 575 | | | | | 580 | |
| AGG | ACA | TAC | ACG | TGG | ACT | CCT | GTC | AAC | GGC | ACA | GAT | TAT | AGC | AGT | TTG | 2174 |
| Arg | Thr | Tyr | Thr | Trp | Thr | Pro | Val | Asn | Gly | Thr | Asp | Tyr | Ser | Ser | Leu | |
| | | | | 585 | | | | | 590 | | | | | 595 | | |
| GCC | TTG | GTA | TTA | CCA | ACC | TAC | AGT | TTT | TAC | TAT | ATA | AAA | GCC | AAA | ATA | 2222 |
| Ala | Leu | Val | Leu | Pro | Thr | Tyr | Ser | Phe | Tyr | Tyr | Ile | Lys | Ala | Lys | Ile | |
| | | | | 600 | | | | 605 | | | | | 610 | | | |
| GAA | GAG | ACA | ATA | ACT | CAG | GCC | AGA | TAT | TCA | GAA | ACA | CTG | AAA | CCG | GAT | 2270 |
| Glu | Glu | Thr | Ile | Thr | Gln | Ala | Arg | Tyr | Ser | Glu | Thr | Leu | Lys | Pro | Asp | |
| | | 615 | | | | 620 | | | | | 625 | | | | | |
| AAT | TTT | GAA | GAA | TCT | GGC | TAC | ACA | TTC | CTA | GCA | CCA | AGA | GAT | TAC | TGC | 2318 |
| Asn | Phe | Glu | Glu | Ser | Gly | Tyr | Thr | Phe | Leu | Ala | Pro | Arg | Asp | Tyr | Cys | |
| | 630 | | | | | 635 | | | | | 640 | | | | | |
| AGT | GAC | CTT | AAA | CCT | TCA | GAT | AAT | AAC | ACT | GAA | TTT | CTT | TTA | AAT | TTC | 2366 |
| Ser | Asp | Leu | Lys | Pro | Ser | Asp | Asn | Asn | Thr | Glu | Phe | Leu | Leu | Asn | Phe | |
| 645 | | | | | 650 | | | | | 655 | | | | | 660 | |
| AAT | GAG | TTT | ATT | GAT | AGA | AAA | ACT | CCA | AAC | AAC | CCA | TCC | TGT | AAT | ACA | 2414 |
| Asn | Glu | Phe | Ile | Asp | Arg | Lys | Thr | Pro | Asn | Asn | Pro | Ser | Cys | Asn | Thr | |
| | | | | 665 | | | | | 670 | | | | | 675 | | |
| GAC | TTG | ATT | AAT | AGA | GTC | TTG | CTG | GAT | GCA | GGC | TTT | ACA | AAT | GAA | CTT | 2462 |
| Asp | Leu | Ile | Asn | Arg | Val | Leu | Leu | Asp | Ala | Gly | Phe | Thr | Asn | Glu | Leu | |
| | | | 680 | | | | | 685 | | | | | 690 | | | |
| GTT | CAA | AAT | TAC | TGG | AGT | AAG | CAG | AAG | AAT | ATC | AAG | GGA | GTG | AAA | GCA | 2510 |
| Val | Gln | Asn | Tyr | Trp | Ser | Lys | Gln | Lys | Asn | Ile | Lys | Gly | Val | Lys | Ala | |
| | | 695 | | | | 700 | | | | | 705 | | | | | |

```
CGG TTT GTT GTG ACT GAT GGT GGG ATT ACC AGA GTT TAT CCC AAA GAG     2558
Arg Phe Val Val Thr Asp Gly Gly Ile Thr Arg Val Tyr Pro Lys Glu
    710             715                 720

GCT GGA GAA AAT TGG CAG GAA AAC CCA GAG ACA TAT GAA GAC AGC TTC     2606
Ala Gly Glu Asn Trp Gln Glu Asn Pro Glu Thr Tyr Glu Asp Ser Phe
725             730                 735                 740

TAT AAA AGG AGC CTC GAT AAT GAT AAC TAC GTT TTC ACT GCT CCC TAC     2654
Tyr Lys Arg Ser Leu Asp Asn Asp Asn Tyr Val Phe Thr Ala Pro Tyr
                745                 750                 755

TTT AAC AAA AGT GGA CCT GGG GCC TAT GAG TCA GGC ATT ATG GTA AGC     2702
Phe Asn Lys Ser Gly Pro Gly Ala Tyr Glu Ser Gly Ile Met Val Ser
            760                 765                 770

AAA GCT GTA GAA ATA TAT ATC CAA GGA AAA CTT CTT AAA CCT GCA GTT     2750
Lys Ala Val Glu Ile Tyr Ile Gln Gly Lys Leu Leu Lys Pro Ala Val
        775                 780                 785

GTT GGA ATT AAA ATT GAT GTA AAT TCT TGG ATA GAG AAT TTC ACC AAA     2798
Val Gly Ile Lys Ile Asp Val Asn Ser Trp Ile Glu Asn Phe Thr Lys
    790                 795                 800

ACT TCA ATC AGG GAT CCG TGT GCT GGT CCA GTT TGT GAC TGC AAA CGA     2846
Thr Ser Ile Arg Asp Pro Cys Ala Gly Pro Val Cys Asp Cys Lys Arg
805             810                 815                 820

AAC AGT GAT GTA ATG GAT TGT GTG ATT CTA GAT GAC GGT GGG TTT CTT     2894
Asn Ser Asp Val Met Asp Cys Val Ile Leu Asp Asp Gly Gly Phe Leu
                825                 830                 835

TTG ATG GCC AAC CAT GAT GAT TAT ACC AAT CAG ATT GGA AGA TTC TTT     2942
Leu Met Ala Asn His Asp Asp Tyr Thr Asn Gln Ile Gly Arg Phe Phe
            840                 845                 850

GGA GAG ATT GAT CCA AGC TTG ATG AGA CAC CTG GTC AAT ATA TCA GTT     2990
Gly Glu Ile Asp Pro Ser Leu Met Arg His Leu Val Asn Ile Ser Val
        855                 860                 865

TAT GCC TTT AAC AAA TCT TAT GAT TAT CAG TCG GTG TGT GAA CCT GGT     3038
Tyr Ala Phe Asn Lys Ser Tyr Asp Tyr Gln Ser Val Cys Glu Pro Gly
    870                 875                 880

GCT GCG CCA AAG CAG GGA GCA GGG CAC CGC TCG GCT TAT GTG CCA TCA     3086
Ala Ala Pro Lys Gln Gly Ala Gly His Arg Ser Ala Tyr Val Pro Ser
885             890                 895                 900

ATA GCA GAC ATA CTG CAG ATT GGA TGG TGG GCC ACT GCT GCT GCC TGG     3134
Ile Ala Asp Ile Leu Gln Ile Gly Trp Trp Ala Thr Ala Ala Ala Trp
                905                 910                 915

TCT ATT CTT CAG CAG TTT CTG TTG AGT TTG ACT TTT CCA CGG CTC CTT     3182
Ser Ile Leu Gln Gln Phe Leu Leu Ser Leu Thr Phe Pro Arg Leu Leu
            920                 925                 930

GAG GCA GCT GAT ATG GAG GAT GAC GAC TTC ACT GCC TCC ATG TCA AAG     3230
Glu Ala Ala Asp Met Glu Asp Asp Asp Phe Thr Ala Ser Met Ser Lys
        935                 940                 945

CAG AGC TGC ATC ACT GAG CAA ACC CAG TAT TTC TTC GAT AAT GAC AGC     3278
Gln Ser Cys Ile Thr Glu Gln Thr Gln Tyr Phe Phe Asp Asn Asp Ser
    950                 955                 960

AAA TCG TTC AGT GGG GTA TTA GAC TGT GGG AAT TGT TCC AGA ATC TTT     3326
Lys Ser Phe Ser Gly Val Leu Asp Cys Gly Asn Cys Ser Arg Ile Phe
965             970                 975                 980

CAT GTA GAA AAG CTC ATG AAC ACC AAT TTA ATA TTC ATA ATG GTA GAG     3374
His Val Glu Lys Leu Met Asn Thr Asn Leu Ile Phe Ile Met Val Glu
                985                 990                 995

AGC AAG GGG ACA TGT CCC TGT GAC ACA CGG CTG CTC ATA CAA GCA GAG     3422
Ser Lys Gly Thr Cys Pro Cys Asp Thr Arg Leu Leu Ile Gln Ala Glu
            1000                1005                1010

CAA ACT TCT GAT GGA CCA GAT CCT TGT GAT ATG GTT AAG CAA CCC AGA     3470
Gln Thr Ser Asp Gly Pro Asp Pro Cys Asp Met Val Lys Gln Pro Arg
        1015                1020                1025
```

```
TAT CGA AAA GGG CCA GAT GTC TGC TTT GAC AAC AAT GTC CTG GAG GAT       3518
Tyr Arg Lys Gly Pro Asp Val Cys Phe Asp Asn Asn Val Leu Glu Asp
    1030            1035                1040

TAT ACT GAC TGC GGT GGG GTC TCT GGA TTA AAT CCT TCC CTG TGG TCC       3566
Tyr Thr Asp Cys Gly Gly Val Ser Gly Leu Asn Pro Ser Leu Trp Ser
1045            1050                1055                1060

ATC ATC GGG ATA CAG TTT GTA CTG CTT TGG CTG GTT TCT GGC AGC AGA       3614
Ile Ile Gly Ile Gln Phe Val Leu Leu Trp Leu Val Ser Gly Ser Arg
                1065                1070                1075

CAC TGC CTG TTA TGA C CTTCTAAAAC CAAATCTCCA TAATTAAACT CCAGACCCTG     3670
His Cys Leu Leu  *
            1080

CCACAACATG ATCCCTCCGT TATGTTAAAG TAGGGTCAAC TGTTAAATCA GAACATTAGC     3730

TGGGCCTCTG CCATGGCAGA GCCCTAAGGC GCAGACTCAT CAGGCACCCA CTGGCTGCAT     3790

GTCAGGGTGT CC                                                         3802
```

( 2 ) INFORMATION FOR SEQ ID NO:3:

( i ) SEQUENCE CHARACTERISTICS:
        ( A ) LENGTH: 1560 base pairs
        ( B ) TYPE: nucleic acid
        ( C ) STRANDEDNESS: single
        ( D ) TOPOLOGY: unknown ( i i ) MOLECULE TYPE: Genomic DNA ( i x ) FEATURE:
        ( A ) NAME/KEY: Coding Sequence
        ( B ) LOCATION: 35...1558

( x i ) SEQUENCE DESCRIPTION: SEQ ID NO:3:

```
GGGCGGGGGA GGGGGATTGA TCTTCGATCG CAAG ATG GCT GCT GGC TGC CTG CTG     55
                                      Met Ala Ala Gly Cys Leu Leu
                                        1               5

GCC TTG ACT CTG ACA CTT TTC CAA TCT TTG CTC ATC GGC CCC TCG TCG       103
Ala Leu Thr Leu Thr Leu Phe Gln Ser Leu Leu Ile Gly Pro Ser Ser
        10              15                  20

GAG GAG CCG TTC CCT TCG GCC GTC ACT ATC AAA TCA TGG GTG GAT AAG       151
Glu Glu Pro Phe Pro Ser Ala Val Thr Ile Lys Ser Trp Val Asp Lys
25              30                  35

ATG CAA GAA GAC CTT GTC ACA CTG GCA AAA ACA GCA AGT GGA GTC AAT       199
Met Gln Glu Asp Leu Val Thr Leu Ala Lys Thr Ala Ser Gly Val Asn
40              45                  50                  55

CAG CTT GTT GAT ATT TAT GAG AAA TAT CAA GAT TTG TAT ACT GTG GAA       247
Gln Leu Val Asp Ile Tyr Glu Lys Tyr Gln Asp Leu Tyr Thr Val Glu
                60                  65                  70

CCA AAT AAT GCA CGC CAG CTG GTA GAA ATT GCA GCC AGG GAT ATT GAG       295
Pro Asn Asn Ala Arg Gln Leu Val Glu Ile Ala Ala Arg Asp Ile Glu
            75                  80                  85

AAA CTT CTG AGC AAC AGA TCT AAA GCC CTG GTG AGC CTG GCA TTG GAA       343
Lys Leu Leu Ser Asn Arg Ser Lys Ala Leu Val Ser Leu Ala Leu Glu
        90                  95                  100

GCG GAG AAA GTT CAA GCA GCT CAC CAG TGG AGA GAA GAT TTT GCA AGC       391
Ala Glu Lys Val Gln Ala Ala His Gln Trp Arg Glu Asp Phe Ala Ser
105                 110                 115

AAT GAA GTT GTC TAC TAC AAT GCA AAG GAT GAT CTC GAT CCT GAG AAA       439
Asn Glu Val Val Tyr Tyr Asn Ala Lys Asp Asp Leu Asp Pro Glu Lys
120                 125                 130                 135

AAT GAC AGT GAG CCA GGC AGC CAG AGG ATA AAA CCT GTT TTC ATT GAA       487
Asn Asp Ser Glu Pro Gly Ser Gln Arg Ile Lys Pro Val Phe Ile Glu
            140                 145                 150
```

| | | | | | | | | | | | | | | | |
|---|---|---|---|---|---|---|---|---|---|---|---|---|---|---|---|
| GAT | GCT | AAT | TTT | GGA | CGA | CAA | ATA | TCT | TAT | CAG | CAC | GCA | GCA | GTC | CAT | 535
| Asp | Ala | Asn 155 | Phe | Gly | Arg | Gln | Ile | Ser 160 | Tyr | Gln | His | Ala | Ala 165 | Val | His |
| ATT | CCT | ACT | GAC | ATC | TAT | GAG | GGC | TCA | ACA | ATT | GTG | TTA | AAT | GAA | CTC | 583
| Ile | Pro | Thr 170 | Asp | Ile | Tyr | Glu | Gly | Ser 175 | Thr | Ile | Val | Leu 180 | Asn | Glu | Leu |
| AAC | TGG | ACA | AGT | GCC | TTA | GAT | GAA | GTT | TTC | AAA | AAG | AAT | CGC | GAG | GAA | 631
| Asn | Trp | Thr 185 | Ser | Ala | Leu | Asp 190 | Glu | Val | Phe | Lys | Lys 195 | Asn | Arg | Glu | Glu |
| GAC | CCT | TCA | TTA | TTG | TGG | CAG | GTT | TTT | GGC | AGT | GCC | ACT | GGC | CTA | GCT | 679
| Asp 200 | Pro | Ser | Leu | Leu | Trp 205 | Gln | Val | Phe | Gly | Ser 210 | Ala | Thr | Gly | Leu | Ala 215 |
| CGA | TAT | TAT | CCA | GCT | TCA | CCA | TGG | GTT | GAT | AAT | GGT | AGA | ACT | CCA | AAT | 727
| Arg | Tyr | Tyr | Pro | Ala 220 | Ser | Pro | Trp | Val | Asp 225 | Asn | Gly | Arg | Thr | Pro 230 | Asn |
| ATG | ATT | GAC | CTT | TAT | GAT | GTA | CGC | AGA | AGA | CCA | TGG | TAC | ATC | CAA | GGA | 775
| Met | Ile | Asp | Leu 235 | Tyr | Asp | Val | Arg | Arg 240 | Arg | Pro | Trp | Tyr | Ile 245 | Gln | Gly |
| GCT | GCA | TCT | CCT | AAA | GAC | ATG | CTT | ATT | CTG | GTG | GAT | GTG | AGT | GGA | AGT | 823
| Ala | Ala | Ser | Pro 250 | Lys | Asp | Met | Leu | Ile 255 | Leu | Val | Asp | Val | Ser 260 | Gly | Ser |
| GTT | AGT | GGA | TTG | ACA | CTT | AAA | CTG | ATC | CGA | ACA | TCT | GTC | TCC | GAA | ATG | 871
| Val | Ser | Gly | Leu | Thr 265 | Leu | Lys | Leu | Ile | Arg 270 | Thr | Ser | Val | Ser | Glu 275 | Met |
| TTA | GAA | ACC | CTC | TCA | GAT | GAT | GAT | TTC | GTG | AAT | GTA | GCT | TCA | TTT | AAC | 919
| Leu 280 | Glu | Thr | Leu | Ser | Asp 285 | Asp | Asp | Phe | Val | Asn 290 | Val | Ala | Ser | Phe | Asn 295 |
| AGC | AAT | GCT | CAG | GAT | GTA | AGC | TGT | TTT | CAG | CAC | CTT | GTC | CAA | GCA | AAT | 967
| Ser | Asn | Ala | Gln | Asp 300 | Val | Ser | Cys | Phe | Gln 305 | His | Leu | Val | Gln | Ala 310 | Asn |
| GTA | AGA | AAT | AAA | AAA | GTG | TTG | AAA | GAC | GCG | GTG | AAT | AAT | ATC | ACA | GCC | 1015
| Val | Arg | Asn | Lys 315 | Lys | Val | Leu | Lys | Asp 320 | Ala | Val | Asn | Asn | Ile 325 | Thr | Ala |
| AAA | GGA | ATT | ACA | GAT | TAT | AAG | AAG | GGC | TTT | AGT | TTT | GCT | TTT | GAA | CAG | 1063
| Lys | Gly | Ile | Thr 330 | Asp | Tyr | Lys | Lys | Gly 335 | Phe | Ser | Phe | Ala | Phe 340 | Glu | Gln |
| CTG | CTT | AAT | TAT | AAT | GTT | TCC | AGA | GCA | AAC | TGC | AAT | AAG | ATT | ATT | ATG | 1111
| Leu | Leu | Asn | Tyr | Asn 345 | Val | Ser | Arg | Ala | Asn 350 | Cys | Asn | Lys | Ile | Ile 355 | Met |
| CTA | TTC | ACG | GAT | GGA | GAA | GAG | AGA | GCC | CAG | GAG | ATA | TTT | AAC | AAA | TAC | 1159
| Leu 360 | Phe | Thr | Asp | Gly | Glu 365 | Glu | Arg | Ala | Gln | Glu 370 | Ile | Phe | Asn | Lys | Tyr 375 |
| AAT | AAA | GAT | AAA | AAA | CTA | CCT | GTA | TTC | ACC | TTC | TCA | GTT | GGT | CAA | CAC | 1207
| Asn | Lys | Asp | Lys | Lys 380 | Leu | Pro | Val | Phe | Thr 385 | Phe | Ser | Val | Gly | Gln 390 | His |
| AAT | TAT | GAC | AGA | GGA | CCT | ATT | CAG | TGG | ATG | GCC | TGT | GAA | AAC | AAA | GGT | 1255
| Asn | Tyr | Asp | Arg 395 | Gly | Pro | Ile | Gln | Trp 400 | Met | Ala | Cys | Glu | Asn 405 | Lys | Gly |
| TAT | TAT | TAT | GAA | ATT | CCT | TCC | ATT | GGT | GCA | ATA | AGA | ATC | AAT | ACT | CAG | 1303
| Tyr | Tyr | Tyr | Glu 410 | Ile | Pro | Ser | Ile | Gly 415 | Ala | Ile | Arg | Ile | Asn 420 | Thr | Gln |
| GAA | TAT | TTG | GAT | GTT | TTG | GGA | AGA | CCA | ATG | GTT | TTA | GCA | GGA | GAC | AAA | 1351
| Glu | Tyr | Leu 425 | Asp | Val | Leu | Gly | Arg 430 | Pro | Met | Val | Leu | Ala 435 | Gly | Asp | Lys |
| GCT | AAG | CAA | GTC | CAA | TGG | ACA | AAT | GTG | TAC | CTG | GAT | GCA | TTG | GAA | CTG | 1399
| Ala | Lys 440 | Gln | Val | Gln | Trp | Thr 445 | Asn | Val | Tyr | Leu | Asp 450 | Ala | Leu | Glu | Leu 455 |
| GGA | CTT | GTC | ATT | ACT | GGA | ACT | CTT | CCG | GTC | TTC | AAC | ATA | ACC | GGC | CAA | 1447
| Gly | Leu | Val | Ile | Thr 460 | Gly | Thr | Leu | Pro | Val 465 | Phe | Asn | Ile | Thr | Gly 470 | Gln |

-continued

| | | | | | | | | | | | | | | | | |
|---|---|---|---|---|---|---|---|---|---|---|---|---|---|---|---|---|
|TTT|GAA|AAT|AAG|ACA|AAC|TTA|AAG|AAC|CAG|CTG|ATT|CTT|GGT|GTG|ATG|1495|
|Phe|Glu|Asn|Lys|Thr|Asn|Leu|Lys|Asn|Gln|Leu|Ile|Leu|Gly|Val|Met| |
| | |  |475| | | |  |480| | | | |485| | | |
|GGA|GTA|GAT|GTG|TCT|TTG|GAA|GAT|ATT|AAA|AGA|CTG|ACA|CCA|CGT|TTT|1543|
|Gly|Val|Asp|Val|Ser|Leu|Glu|Asp|Ile|Lys|Arg|Leu|Thr|Pro|Arg|Phe| |
| | |490| | | | |495| | | | |500| | | | |
|ACA|CTG|TGC|CCC|AAT|GG| | | | | | | | | | |1560|
|Thr|Leu|Cys|Pro|Asn| | | | | | | | | | | | |
|505| | | | | | | | | | | | | | | | |

( 2 ) INFORMATION FOR SEQ ID NO:4:

( i ) SEQUENCE CHARACTERISTICS:
        ( A ) LENGTH: 1873 amino acids
        ( B ) TYPE: amino acid
        ( C ) STRANDEDNESS: single
        ( D ) TOPOLOGY: linear ( i i ) MOLECULE TYPE: protein ( v ) FRAGMENT TYPE: internal ( x i ) SEQUENCE DESCRIPTION: SEQ ID NO:4:

| | | | | | | | | | | | | | | |
|---|---|---|---|---|---|---|---|---|---|---|---|---|---|---|
|Met|Glu|Pro|Ser|Ser|Pro|Gln|Asp|Glu|Gly|Leu|Arg|Lys|Lys|Gln|Pro|
|1| | | |5| | | |  |10| | | | |15| |
|Lys|Lys|Pro|Leu|Pro|Glu|Val|Leu|Pro|Arg|Pro|Pro|Arg|Ala|Leu|Phe|
| | | |20| | | |25| | | |30| | | | |
|Cys|Leu|Thr|Leu|Gln|Asn|Pro|Leu|Arg|Lys|Ala|Cys|Ile|Ser|Ile|Val|
| | |35| | | |40| | | | |45| | | | |
|Glu|Trp|Lys|Pro|Phe|Glu|Thr|Ile|Ile|Leu|Leu|Thr|Ile|Phe|Ala|Asn|
| |50| | | | |55| | | | |60| | | | |
|Cys|Val|Ala|Leu|Ala|Val|Tyr|Leu|Pro|Met|Pro|Glu|Asp|Asp|Asn|Asn|
|65| | | |70| | | |75| | | | | |80| |
|Ser|Leu|Asn|Leu|Gly|Leu|Glu|Lys|Leu|Glu|Tyr|Phe|Phe|Leu|Thr|Val|
| | | |85| | | | |90| | | | |95| | |
|Phe|Ser|Ile|Glu|Ala|Ala|Met|Lys|Ile|Ile|Ala|Tyr|Gly|Phe|Leu|Phe|
| | | |100| | | |105| | | | |110| | | |
|His|Gln|Asp|Ala|Tyr|Leu|Arg|Ser|Gly|Trp|Asn|Val|Leu|Asp|Phe|Ile|
| | |115| | | |120| | | | |125| | | | |
|Ile|Val|Phe|Leu|Gly|Val|Phe|Thr|Ala|Ile|Leu|Glu|Gln|Val|Asn|Val|
| |130| | | | |135| | | | |140| | | | |
|Ile|Gln|Ser|Asn|Thr|Ala|Pro|Met|Ser|Ser|Lys|Gly|Ala|Gly|Leu|Asp|
|145| | | | |150| | | |155| | | | |160| |
|Val|Lys|Ala|Leu|Arg|Ala|Phe|Arg|Val|Leu|Arg|Pro|Leu|Arg|Leu|Val|
| | | |165| | | |170| | | | |175| | | |
|Ser|Gly|Val|Pro|Ser|Leu|Gln|Val|Val|Leu|Asn|Ser|Ile|Phe|Lys|Ala|
| | |180| | | | |185| | | | |190| | | |
|Met|Leu|Pro|Leu|Phe|His|Ile|Ala|Leu|Leu|Val|Leu|Phe|Met|Val|Ile|
| |195| | | | |200| | | | |205| | | | |
|Ile|Tyr|Ala|Ile|Ile|Gly|Leu|Glu|Leu|Phe|Lys|Gly|Lys|Met|His|Lys|
|210| | | | |215| | | | |220| | | | | |
|Thr|Cys|Tyr|Tyr|Ile|Gly|Thr|Asp|Ile|Val|Ala|Thr|Val|Glu|Asn|Glu|
|225| | | | |230| | | | |235| | | | |240|
|Lys|Pro|Ser|Pro|Cys|Ala|Arg|Thr|Gly|Ser|Gly|Arg|Pro|Cys|Thr|Ile|
| | | | |245| | | | |250| | | | |255| |
|Asn|Gly|Ser|Glu|Cys|Arg|Gly|Gly|Trp|Pro|Gly|Pro|Asn|His|Gly|Ile|
| | | |260| | | | |265| | | | |270| | |
|Thr|His|Phe|Asp|Asn|Phe|Gly|Phe|Ser|Met|Leu|Thr|Val|Tyr|Gln|Cys|
| | |275| | | | |280| | | | |285| | | |

-continued

```
Ile  Thr  Met  Glu  Gly  Trp  Thr  Asp  Val  Leu  Tyr  Trp  Val  Asn  Asp  Ala
     290                 295                 300

Ile  Gly  Asn  Glu  Trp  Pro  Trp  Ile  Tyr  Phe  Val  Thr  Leu  Ile  Leu  Leu
305                      310                 315                           320

Gly  Ser  Phe  Phe  Ile  Leu  Asn  Leu  Val  Leu  Gly  Val  Leu  Ser  Gly  Glu
               325                 330                           335

Phe  Thr  Lys  Glu  Arg  Glu  Lys  Ala  Lys  Ser  Arg  Gly  Thr  Phe  Gln  Lys
               340                 345                      350

Leu  Arg  Glu  Lys  Gln  Gln  Leu  Glu  Glu  Asp  Leu  Arg  Gly  Tyr  Met  Ser
          355                      360                 365

Trp  Ile  Thr  Gln  Gly  Glu  Val  Met  Asp  Val  Glu  Asp  Leu  Arg  Glu  Gly
     370                      375                 380

Lys  Leu  Ser  Leu  Glu  Glu  Gly  Gly  Ser  Asp  Thr  Glu  Ser  Leu  Tyr  Glu
385                      390                 395                           400

Ile  Glu  Gly  Leu  Asn  Lys  Ile  Ile  Gln  Phe  Ile  Arg  His  Trp  Arg  Gln
               405                 410                 415

Trp  Asn  Arg  Val  Phe  Arg  Trp  Lys  Cys  His  Asp  Leu  Val  Lys  Ser  Arg
               420                 425                      430

Val  Phe  Tyr  Trp  Leu  Val  Ile  Leu  Ile  Val  Ala  Leu  Asn  Thr  Leu  Ser
          435                      440                 445

Ile  Ala  Ser  Glu  His  His  Asn  Gln  Pro  Leu  Trp  Leu  Thr  His  Leu  Gln
     450                      455                 460

Asp  Ile  Ala  Asn  Arg  Val  Leu  Leu  Ser  Leu  Phe  Thr  Ile  Glu  Met  Leu
465                      470                 475                           480

Leu  Lys  Met  Tyr  Gly  Leu  Gly  Leu  Arg  Gln  Tyr  Phe  Met  Ser  Ile  Phe
                    485                 490                      495

Asn  Arg  Phe  Asp  Cys  Phe  Val  Val  Cys  Ser  Gly  Ile  Leu  Glu  Leu  Leu
               500                 505                      510

Leu  Val  Glu  Ser  Gly  Ala  Met  Thr  Pro  Leu  Gly  Ile  Ser  Val  Leu  Arg
          515                 520                      525

Cys  Ile  Arg  Leu  Leu  Arg  Leu  Phe  Lys  Ile  Thr  Lys  Tyr  Trp  Thr  Ser
     530                      535                 540

Leu  Ser  Asn  Leu  Val  Ala  Ser  Leu  Leu  Asn  Ser  Ile  Arg  Ser  Ile  Ala
545                      550                 555                           560

Ser  Leu  Leu  Leu  Leu  Leu  Phe  Leu  Phe  Ile  Ile  Phe  Ala  Leu  Leu
               565                 570                           575

Gly  Met  Gln  Leu  Phe  Gly  Gly  Arg  Tyr  Asp  Phe  Glu  Asp  Thr  Glu  Val
               580                      585                 590

Arg  Arg  Ser  Asn  Phe  Asp  Asn  Phe  Pro  Gln  Ala  Leu  Ile  Ser  Val  Phe
          595                 600                      605

Gln  Val  Leu  Thr  Gly  Glu  Asp  Trp  Asn  Ser  Val  Met  Tyr  Asn  Gly  Ile
     610                      615                 620

Met  Ala  Tyr  Gly  Gly  Pro  Ser  Tyr  Pro  Gly  Val  Leu  Val  Cys  Ile  Tyr
625                      630                 635                           640

Phe  Ile  Ile  Leu  Phe  Val  Cys  Gly  Asn  Tyr  Ile  Leu  Leu  Asn  Val  Phe
               645                      650                           655

Leu  Ala  Ile  Ala  Val  Asp  Asn  Leu  Ala  Glu  Ala  Glu  Ser  Leu  Thr  Ser
               660                 665                      670

Ala  Gln  Lys  Ala  Lys  Ala  Glu  Glu  Arg  Lys  Arg  Arg  Lys  Met  Ser  Arg
          675                 680                      685

Gly  Leu  Pro  Asp  Lys  Thr  Glu  Glu  Glu  Lys  Ser  Val  Met  Ala  Lys  Lys
     690                 695                      700

Leu  Glu  Gln  Lys  Pro  Lys  Gly  Glu  Gly  Ile  Pro  Thr  Thr  Ala  Lys  Leu
```

-continued

```
            705                    710                    715                    720
Lys Val Asp Glu Phe Glu Ser Asn Val Asn Glu Val Lys Asp Pro Tyr
                    725                    730                    735
Pro Ser Ala Asp Phe Pro Gly Asp Asp Glu Asp Glu Pro Glu Ile
                740                    745                    750
Pro Val Ser Pro Arg Pro Arg Pro Leu Ala Glu Leu Gln Leu Lys Glu
                755                    760                    765
Lys Ala Val Pro Ile Pro Glu Ala Ser Ser Phe Phe Ile Phe Ser Pro
            770                    775                    780
Thr Asn Lys Val Arg Val Leu Cys His Arg Ile Val Asn Ala Thr Trp
785                    790                    795                    800
Phe Thr Asn Phe Ile Leu Leu Phe Ile Leu Leu Ser Ser Ala Ala Leu
                        805                    810                    815
Ala Ala Glu Asp Pro Ile Arg Ala Glu Ser Val Arg Asn Gln Ile Leu
            820                    825                    830
Gly Tyr Phe Asp Ile Ala Phe Thr Ser Val Phe Thr Val Glu Ile Val
            835                    840                    845
Leu Lys Met Thr Thr Tyr Gly Ala Phe Leu His Lys Gly Ser Phe Cys
850                    855                    860
Arg Asn Tyr Phe Asn Ile Leu Asp Leu Leu Val Ala Val Ser Leu
865                    870                    875                    880
Ile Ser Met Gly Leu Glu Ser Ser Thr Ile Ser Val Val Lys Ile Leu
                    885                    890                    895
Arg Val Leu Arg Val Leu Arg Pro Leu Arg Ala Ile Asn Arg Ala Lys
                900                    905                    910
Gly Leu Lys His Val Val Gln Cys Val Phe Val Ala Ile Arg Thr Ile
            915                    920                    925
Gly Asn Ile Val Leu Val Thr Thr Leu Leu Gln Phe Met Phe Ala Cys
    930                    935                    940
Ile Gly Val Gln Leu Phe Lys Gly Lys Phe Phe Ser Cys Asn Asp Leu
945                    950                    955                    960
Ser Lys Met Thr Glu Glu Glu Cys Arg Gly Tyr Tyr Tyr Val Tyr Lys
                965                    970                    975
Asp Gly Asp Pro Thr Gln Met Glu Leu Arg Pro Arg Gln Trp Ile His
            980                    985                    990
Asn Asp Phe His Phe Asp Asn Val Leu Ser Ala Met Met Ser Leu Phe
            995                    1000                   1005
Thr Val Ser Thr Phe Glu Gly Trp Pro Gln Leu Leu Tyr Arg Ala Ile
    1010                   1015                   1020
Asp Ser Asn Glu Glu Asp Met Gly Pro Val Tyr Asn Asn Arg Val Glu
1025                   1030                   1035                   1040
Met Ala Ile Phe Phe Ile Ile Tyr Ile Ile Leu Ile Ala Phe Phe Met
                    1045                   1050                   1055
Met Asn Ile Phe Val Gly Phe Val Ile Val Thr Phe Gln Glu Gln Gly
            1060                   1065                   1070
Glu Thr Glu Tyr Lys Asn Cys Glu Leu Asp Lys Asn Gln Arg Gln Cys
        1075                   1080                   1085
Val Gln Tyr Ala Leu Lys Ala Arg Pro Leu Arg Cys Tyr Ile Pro Lys
    1090                   1095                   1100
Asn Pro Tyr Gln Tyr Gln Val Trp Tyr Val Val Thr Ser Ser Tyr Phe
1105                   1110                   1115                   1120
Glu Tyr Leu Met Phe Ala Leu Ile Met Leu Asn Thr Ile Cys Leu Gly
                1125                   1130                   1135
```

```
Met Gln His Tyr His Gln Ser Glu Glu Met Asn His Ile Ser Asp Ile
            1140                1145                1150
Leu Asn Val Ala Phe Thr Ile Ile Phe Thr Leu Glu Met Ile Leu Lys
        1155                1160                1165
Leu Leu Ala Phe Lys Ala Arg Gly Tyr Phe Gly Asp Pro Trp Asn Val
    1170                1175                1180
Phe Asp Phe Leu Ile Val Ile Gly Ser Ile Ile Asp Val Ile Leu Ser
1185                1190                1195                1200
Glu Ile Asp Thr Phe Leu Ala Ser Ser Gly Gly Leu Tyr Cys Leu Gly
                1205                1210                1215
Gly Gly Cys Gly Asn Val Asp Pro Asp Glu Ser Ala Arg Ile Ser Ser
            1220                1225                1230
Ala Phe Phe Arg Leu Phe Arg Val Met Arg Leu Ile Lys Leu Leu Ser
        1235                1240                1245
Arg Ala Glu Gly Val Arg Thr Leu Leu Trp Thr Phe Ile Lys Ser Phe
    1250                1255                1260
Gln Ala Leu Pro Tyr Val Ala Leu Leu Ile Val Met Leu Phe Phe Ile
1265                1270                1275                1280
Tyr Ala Val Ile Gly Met Gln Met Phe Gly Lys Ile Ala Leu Val Asp
                1285                1290                1295
Gly Thr Gln Ile Asn Arg Asn Asn Asn Phe Gln Thr Phe Pro Gln Ala
            1300                1305                1310
Val Leu Leu Leu Phe Arg Cys Ala Thr Gly Glu Ala Trp Gln Glu Ile
        1315                1320                1325
Leu Leu Ala Cys Ser Tyr Gly Lys Leu Cys Asp Pro Glu Ser Asp Tyr
    1330                1335                1340
Ala Pro Gly Glu Glu Tyr Thr Cys Gly Thr Asn Phe Ala Tyr Tyr Tyr
1345                1350                1355                1360
Phe Ile Ser Phe Tyr Met Leu Cys Ala Phe Leu Ile Ile Asn Leu Phe
                1365                1370                1375
Val Ala Val Ile Met Asp Asn Phe Asp Tyr Leu Thr Arg Asp Trp Ser
            1380                1385                1390
Ile Leu Gly Pro His His Leu Asp Glu Phe Lys Ala Ile Trp Ala Glu
        1395                1400                1405
Tyr Asp Pro Glu Ala Lys Gly Arg Ile Lys His Leu Asp Val Val Thr
    1410                1415                1420
Leu Leu Arg Arg Ile Gln Pro Pro Leu Gly Phe Gly Lys Phe Cys Pro
1425                1430                1435                1440
His Arg Val Ala Cys Lys Arg Leu Val Gly Met Asn Met Pro Leu Asn
                1445                1450                1455
Ser Asp Gly Thr Val Thr Phe Asn Ala Thr Leu Phe Ala Leu Val Arg
            1460                1465                1470
Thr Ala Leu Lys Ile Lys Thr Glu Gly Asn Phe Glu Gln Ala Asn Glu
        1475                1480                1485
Glu Leu Arg Ala Ile Ile Lys Lys Ile Trp Lys Arg Thr Ser Met Lys
    1490                1495                1500
Leu Leu Asp Gln Val Ile Pro Pro Ile Gly Asp Asp Glu Val Thr Val
1505                1510                1515                1520
Gly Lys Phe Tyr Ala Thr Phe Leu Ile Gln Glu His Phe Arg Lys Phe
                1525                1530                1535
Met Lys Arg Gln Glu Glu Tyr Tyr Gly Tyr Arg Pro Lys Lys Asp Thr
            1540                1545                1550
Val Gln Ile Gln Ala Gly Leu Arg Thr Ile Glu Glu Ala Ala Pro
        1555                1560                1565
```

Glu Ile Arg Arg Thr Ile Ser Gly Asp Leu Thr Ala Glu Glu Glu Leu
1570                1575                1580

Glu Arg Ala Met Val Glu Ala Ala Met Glu Arg Ile Phe Arg Arg
1585            1590            1595                1600

Thr Gly Gly Leu Phe Gly Gln Val Asp Thr Phe Leu Glu Arg Thr Asn
                1605            1610            1615

Ser Leu Pro Pro Val Met Ala Asn Gln Arg Pro Leu Gln Phe Ala Glu
            1620            1625            1630

Ile Glu Met Glu Glu Leu Glu Ser Pro Val Phe Leu Glu Asp Phe Pro
        1635            1640            1645

Gln Asp Ala Arg Thr Asn Pro Leu Ala Arg Ala Asn Thr Asn Asn Ala
    1650            1655            1660

Asn Ala Asn Val Ala Tyr Gly Asn Ser Asn His Ser Asn Asn Gln Met
1665            1670            1675                1680

Phe Ser Ser Val His Cys Glu Arg Glu Phe Pro Gly Glu Ala Glu Thr
                1685            1690            1695

Pro Ala Ala Gly Arg Gly Ala Leu Ser His Ser His Arg Ala Leu Gly
            1700            1705            1710

Pro His Ser Lys Pro Cys Ala Gly Lys Leu Asn Gly Gln Leu Val Gln
        1715            1720            1725

Pro Gly Met Pro Ile Asn Gln Ala Pro Pro Ala Pro Cys Gln Gln Pro
    1730            1735            1740

Ser Thr Asp Pro Pro Glu Arg Gly Gln Arg Arg Thr Ser Leu Thr Gly
1745            1750            1755                1760

Ser Leu Gln Asp Glu Ala Pro Gln Arg Arg Ser Ser Glu Gly Ser Thr
            1765            1770            1775

Pro Arg Arg Pro Ala Pro Ala Thr Ala Leu Leu Ile Gln Glu Ala Leu
        1780            1785            1790

Val Arg Gly Gly Leu Asp Thr Leu Ala Ala Asp Ala Gly Phe Val Met
    1795            1800            1805

Ala Thr Ser Gln Ala Leu Val Asp Ala Cys Gln Met Glu Pro Glu Glu
    1810            1815            1820

Val Glu Val Ala Ala Thr Glu Leu Leu Lys Glu Arg Glu Ser Val Gln
1825            1830            1835                1840

Gly Met Ala Ser Val Pro Gly Ser Leu Ser Arg Arg Ser Ser Leu Gly
            1845            1850            1855

Ser Leu Asp Gln Val Gln Gly Ser Gln Glu Thr Leu Ile Pro Pro Arg
        1860            1865            1870

Pro ( 2 ) INFORMATION FOR SEQ ID NO:5:

( i ) SEQUENCE CHARACTERISTICS:
        ( A ) LENGTH: 1106 amino acids
        ( B ) TYPE: amino acid
        ( C ) STRANDEDNESS: single
        ( D ) TOPOLOGY: linear ( i i ) MOLECULE TYPE: protein ( v ) FRAGMENT TYPE: internal ( x i ) SEQUENCE DESCRIPTION: SEQ ID NO:5:

Met Ala Ala Gly Arg Pro Leu Ala Trp Thr Leu Thr Leu Trp Gln Ala
1           5               10              15

Trp Leu Ile Leu Ile Gly Pro Ser Ser Glu Glu Pro Phe Pro Ser Ala
            20              25              30

-continued

| | | | | | | | | | | | | | | |
|---|---|---|---|---|---|---|---|---|---|---|---|---|---|---|
|Val|Thr|Ile<br>35|Lys|Ser|Trp|Val|Asp<br>40|Lys|Met|Gln|Glu|Asp<br>45|Leu|Val|Thr|
|Leu|Ala|Lys|Thr|Ala|Ser|Gly|Val|Asn|Gln|Leu|Val|Asp|Ile|Tyr|Glu|
| |50| | | |55| | | |60| | | | | | |
|Lys|Tyr|Gln|Asp|Leu|Tyr|Thr|Val|Glu|Pro|Asn|Asn|Ala|Arg|Gln|Leu|
|65| | | | |70| | | |75| | | | | |80|
|Val|Glu|Ile|Ala|Ala|Arg|Asp|Ile|Glu|Lys|Leu|Leu|Ser|Asn|Arg|Ser|
| | | | |85| | | |90| | | | |95| | |
|Lys|Ala|Leu|Val|Arg|Leu|Ala|Leu|Glu|Ala|Glu|Lys|Val|Gln|Ala|Ala|
| | | |100| | | | |105| | | |110| | | |
|His|Gln|Trp|Arg|Glu|Asp|Phe|Ala|Ser|Asn|Glu|Val|Val|Tyr|Tyr|Asn|
| | |115| | | | |120| | | | |125| | | |
|Ala|Lys|Asp|Asp|Leu|Asp|Pro|Glu|Lys|Asn|Asp|Ser|Glu|Pro|Gly|Ser|
| |130| | | | |135| | | | |140| | | | |
|Gln|Arg|Ile|Lys|Pro|Val|Phe|Ile|Asp|Asp|Ala|Asn|Phe|Arg|Arg|Gln|
|145| | | | |150| | | | |155| | | | |160|
|Val|Ser|Tyr|Gln|His|Ala|Ala|Val|His|Ile|Pro|Thr|Asp|Ile|Tyr|Glu|
| | | | |165| | | | |170| | | | |175| |
|Gly|Ser|Thr|Ile|Val|Leu|Asn|Glu|Leu|Asn|Trp|Thr|Ser|Ala|Leu|Asp|
| | | |180| | | | |185| | | | |190| | |
|Asp|Val|Phe|Lys|Lys|Asn|Arg|Glu|Glu|Asp|Pro|Ser|Leu|Leu|Trp|Gln|
| | | |195| | | | |200| | | | |205| | |
|Val|Phe|Gly|Ser|Ala|Thr|Gly|Leu|Ala|Arg|Tyr|Tyr|Pro|Ala|Ser|Pro|
| | | |210| | | | |215| | | | |220| | |
|Trp|Val|Asp|Asn|Ser|Arg|Thr|Pro|Asn|Lys|Ile|Asp|Leu|Tyr|Asp|Val|
|225| | | | |230| | | | |235| | | | |240|
|Arg|Arg|Arg|Pro|Trp|Tyr|Ile|Gln|Gly|Ala|Ala|Ser|Pro|Lys|Asp|Met|
| | | | |245| | | | |250| | | | |255| |
|Leu|Ile|Leu|Val|Asp|Val|Ser|Gly|Ser|Val|Ser|Gly|Leu|Thr|Leu|Lys|
| | | |260| | | | |265| | | | |270| | |
|Leu|Ile|Arg|Thr|Ser|Val|Ser|Glu|Met|Leu|Glu|Thr|Leu|Ser|Asp|Asp|
| | |275| | | | |280| | | | |285| | | |
|Asp|Phe|Val|Asn|Val|Ala|Ser|Phe|Asn|Ser|Asn|Ala|Gln|Asp|Val|Ser|
| |290| | | | |295| | | | |300| | | | |
|Cys|Phe|Gln|His|Leu|Val|Gln|Ala|Asn|Val|Arg|Asn|Lys|Lys|Val|Leu|
|305| | | | |310| | | | |315| | | | |320|
|Lys|Asp|Ala|Val|Asn|Asn|Ile|Thr|Ala|Lys|Gly|Ile|Thr|Asp|Tyr|Lys|
| | | | |325| | | | |330| | | | |335| |
|Lys|Gly|Phe|Ser|Phe|Ala|Phe|Glu|Gln|Leu|Leu|Asn|Tyr|Asn|Val|Ser|
| | | |340| | | | |345| | | | |350| | |
|Arg|Ala|Asn|Cys|Asn|Lys|Ile|Ile|Met|Leu|Phe|Thr|Asp|Gly|Gly|Glu|
| | | |355| | | | |360| | | | |365| | |
|Glu|Arg|Ala|Gln|Glu|Ile|Phe|Ala|Lys|Tyr|Asn|Lys|Asp|Lys|Lys|Val|
| |370| | | | |375| | | | |380| | | | |
|Arg|Val|Phe|Thr|Phe|Ser|Val|Gly|Gln|His|Asn|Tyr|Asp|Arg|Gly|Pro|
|385| | | | |390| | | | |395| | | | |400|
|Ile|Gln|Trp|Met|Ala|Cys|Glu|Asn|Lys|Gly|Tyr|Tyr|Tyr|Glu|Ile|Pro|
| | | | |405| | | | |410| | | | |415| |
|Ser|Ile|Gly|Ala|Ile|Arg|Ile|Asn|Thr|Gln|Glu|Tyr|Leu|Asp|Val|Leu|
| | | |420| | | | |425| | | | |430| | |
|Gly|Arg|Pro|Met|Val|Leu|Ala|Gly|Asp|Lys|Ala|Lys|Gln|Val|Gln|Trp|
| | |435| | | | |440| | | | |445| | | |
|Thr|Asn|Val|Tyr|Leu|Asp|Ala|Leu|Glu|Leu|Gly|Leu|Val|Ile|Thr|Gly|

-continued

```
                450                          455                          460
Thr Leu Pro Val Phe Asn Ile Thr Gly Gln Phe Glu Asn Lys Thr Asn
465                     470                     475                     480
Leu Lys Asn Gln Leu Ile Leu Gly Val Met Gly Val Asp Val Ser Leu
                    485                     490                     495
Glu Asp Ile Lys Arg Leu Thr Pro Arg Phe Thr Leu Cys Pro Asn Gly
            500                     505                     510
Tyr Tyr Phe Ala Ile Asp Pro Asn Gly Tyr Val Leu Leu His Pro Asn
        515                     520                     525
Leu Gln Pro Lys Pro Ile Gly Val Gly Ile Pro Thr Ile Asn Leu Arg
    530                     535                     540
Lys Arg Arg Pro Asn Val Gln Asn Pro Lys Ser Gln Glu Pro Val Thr
545                     550                     555                     560
Leu Asp Phe Leu Asp Ala Glu Leu Glu Asn Asp Ile Lys Val Glu Ile
                    565                     570                     575
Arg Asn Lys Met Ile Asp Gly Glu Ser Gly Glu Lys Thr Phe Arg Thr
                580                     585                     590
Leu Val Lys Ser Gln Asp Glu Arg Tyr Ile Asp Lys Gly Asn Arg Thr
            595                     600                     605
Tyr Thr Trp Thr Pro Val Asn Gly Thr Asp Tyr Ser Ser Leu Ala Leu
        610                     615                     620
Val Leu Pro Thr Tyr Ser Phe Tyr Tyr Ile Lys Ala Lys Ile Glu Glu
625                     630                     635                     640
Thr Ile Thr Gln Ala Arg Tyr Ser Glu Thr Leu Lys Pro Asp Asn Phe
                645                     650                     655
Glu Glu Ser Gly Tyr Thr Phe Leu Ala Pro Arg Asp Tyr Cys Ser Asp
                660                     665                     670
Leu Lys Pro Ser Asp Asn Asn Thr Glu Phe Leu Leu Asn Phe Asn Glu
            675                     680                     685
Phe Ile Asp Arg Lys Thr Pro Asn Asn Pro Ser Cys Asn Thr Asp Leu
        690                     695                     700
Ile Asn Arg Val Leu Leu Asp Ala Gly Phe Thr Asn Glu Leu Val Gln
705                     710                     715                     720
Asn Tyr Trp Ser Lys Gln Lys Asn Ile Lys Gly Val Lys Ala Arg Phe
                    725                     730                     735
Val Val Thr Asp Gly Gly Ile Thr Arg Val Tyr Pro Lys Glu Ala Gly
                740                     745                     750
Glu Asn Trp Gln Glu Asn Pro Glu Thr Tyr Glu Asp Ser Phe Tyr Lys
            755                     760                     765
Arg Ser Leu Asp Asn Asp Asn Tyr Val Phe Thr Ala Pro Tyr Phe Asn
    770                     775                     780
Lys Ser Gly Pro Gly Ala Tyr Glu Ser Gly Ile Met Val Ser Lys Ala
785                     790                     795                     800
Val Glu Ile Tyr Ile Gln Gly Lys Leu Leu Lys Pro Ala Val Val Gly
                    805                     810                     815
Ile Lys Ile Asp Val Asn Ser Trp Ile Glu Asn Phe Thr Lys Thr Ser
                820                     825                     830
Ile Arg Asp Pro Cys Ala Gly Pro Val Cys Asp Cys Lys Arg Asn Ser
            835                     840                     845
Asp Val Met Asp Cys Val Ile Leu Asp Asp Gly Gly Phe Leu Leu Met
        850                     855                     860
Ala Asn His Asp Asp Tyr Thr Asn Gln Ile Gly Arg Phe Phe Gly Glu
    865                     870                     875                     880
```

| Ile | Asp | Pro | Ser | Leu | Met | Arg | His | Leu | Val | Asn | Ile | Ser | Val | Tyr | Ala |
|---|---|---|---|---|---|---|---|---|---|---|---|---|---|---|---|
| | | | | 885 | | | | 890 | | | | | 895 | | |

| Phe | Asn | Lys | Ser | Tyr | Asp | Tyr | Gln | Ser | Val | Cys | Glu | Pro | Gly | Ala | Ala |
|---|---|---|---|---|---|---|---|---|---|---|---|---|---|---|---|
| | | | 900 | | | | 905 | | | | | 910 | | | |

| Pro | Lys | Gln | Gly | Ala | Gly | His | Arg | Ser | Ala | Tyr | Val | Pro | Ser | Ile | Ala |
|---|---|---|---|---|---|---|---|---|---|---|---|---|---|---|---|
| | | 915 | | | | | 920 | | | | | 925 | | | |

Asp Ile Leu Gln Ile Gly Trp Trp Ala Thr Ala Ala Ala Trp Ser Ile
930                935                940

Leu Gln Gln Phe Leu Leu Ser Leu Thr Phe Pro Arg Leu Leu Glu Ala
945           950               955               960

Ala Asp Met Glu Asp Asp Asp Phe Thr Ala Ser Met Ser Lys Gln Ser
            965               970               975

Cys Ile Thr Glu Gln Thr Gln Tyr Phe Phe Asp Asn Asp Ser Lys Ser
            980               985               990

Phe Ser Gly Val Leu Asp Cys Gly Asn Cys Ser Arg Ile Phe His Val
            995             1000              1005

Glu Lys Leu Met Asn Thr Asn Leu Ile Phe Ile Met Val Glu Ser Lys
1010              1015              1020

Gly Thr Cys Pro Cys Asp Thr Arg Leu Leu Ile Gln Ala Glu Gln Thr
1025              1030              1035              1040

Ser Asp Gly Pro Asp Pro Cys Asp Met Val Lys Gln Pro Arg Tyr Arg
                1045              1050              1055

Lys Gly Pro Asp Val Cys Phe Asp Asn Asn Val Leu Glu Asp Tyr Thr
                1060              1065              1070

Asp Cys Gly Gly Val Ser Gly Leu Asn Pro Ser Leu Trp Ser Ile Ile
            1075              1080              1085

Gly Ile Gln Phe Val Leu Leu Trp Leu Val Ser Gly Ser Arg His Cys
1090              1095              1100

Leu Leu
1105

( 2 ) INFORMATION FOR SEQ ID NO:6:

( i ) SEQUENCE CHARACTERISTICS:
        ( A ) LENGTH: 508 amino acids
        ( B ) TYPE: amino acid
        ( C ) STRANDEDNESS: single
        ( D ) TOPOLOGY: linear ( i i ) MOLECULE TYPE: protein ( v ) FRAGMENT TYPE: internal ( x i ) SEQUENCE DESCRIPTION: SEQ ID NO:6:

Met Ala Ala Gly Cys Leu Leu Ala Leu Thr Leu Thr Leu Phe Gln Ser
1               5               10              15

Leu Leu Ile Gly Pro Ser Ser Glu Glu Pro Phe Pro Ser Ala Val Thr
            20              25              30

Ile Lys Ser Trp Val Asp Lys Met Gln Glu Asp Leu Val Thr Leu Ala
            35              40              45

Lys Thr Ala Ser Gly Val Asn Gln Leu Val Asp Ile Tyr Glu Lys Tyr
50              55              60

Gln Asp Leu Tyr Thr Val Glu Pro Asn Asn Ala Arg Gln Leu Val Glu
65              70              75              80

Ile Ala Ala Arg Asp Ile Glu Lys Leu Leu Ser Asn Arg Ser Lys Ala
                85              90              95

Leu Val Ser Leu Ala Leu Glu Ala Glu Lys Val Gln Ala Ala His Gln
            100             105             110

```
Trp Arg Glu Asp Phe Ala Ser Asn Glu Val Val Tyr Tyr Asn Ala Lys
    115             120             125
Asp Asp Leu Asp Pro Glu Lys Asn Asp Ser Glu Pro Gly Ser Gln Arg
130             135             140
Ile Lys Pro Val Phe Ile Glu Asp Ala Asn Phe Gly Arg Gln Ile Ser
145             150             155             160
Tyr Gln His Ala Ala Val His Ile Pro Thr Asp Ile Tyr Glu Gly Ser
                165             170             175
Thr Ile Val Leu Asn Glu Leu Asn Trp Thr Ser Ala Leu Asp Glu Val
            180             185             190
Phe Lys Lys Asn Arg Glu Glu Asp Pro Ser Leu Leu Trp Gln Val Phe
        195             200             205
Gly Ser Ala Thr Gly Leu Ala Arg Tyr Tyr Pro Ala Ser Pro Trp Val
    210             215             220
Asp Asn Gly Arg Thr Pro Asn Met Ile Asp Leu Tyr Asp Val Arg Arg
225             230             235             240
Arg Pro Trp Tyr Ile Gln Gly Ala Ala Ser Pro Lys Asp Met Leu Ile
                245             250             255
Leu Val Asp Val Ser Gly Ser Val Ser Gly Leu Thr Leu Lys Leu Ile
            260             265             270
Arg Thr Ser Val Ser Glu Met Leu Glu Thr Leu Ser Asp Asp Asp Phe
        275             280             285
Val Asn Val Ala Ser Phe Asn Ser Asn Ala Gln Asp Val Ser Cys Phe
    290             295             300
Gln His Leu Val Gln Ala Asn Val Arg Asn Lys Val Leu Lys Leu Asp
305             310             315             320
Ala Val Asn Asn Ile Thr Ala Lys Gly Ile Thr Asp Tyr Lys Lys Gly
                325             330             335
Phe Ser Phe Ala Phe Glu Gln Leu Leu Asn Tyr Asn Val Ser Arg Ala
            340             345             350
Asn Cys Asn Lys Ile Ile Met Leu Phe Thr Asp Gly Glu Glu Arg Ala
        355             360             365
Gln Glu Ile Phe Asn Lys Tyr Asn Lys Asp Lys Lys Leu Pro Val Phe
    370             375             380
Thr Phe Ser Val Gly Gln His Asn Tyr Asp Arg Gly Pro Ile Gln Trp
385             390             395             400
Met Ala Cys Glu Asn Lys Gly Tyr Tyr Tyr Glu Ile Pro Ser Ile Gly
                405             410             415
Ala Ile Arg Ile Asn Thr Gln Glu Tyr Leu Asp Val Leu Gly Arg Pro
            420             425             430
Met Val Leu Ala Gly Asp Lys Ala Lys Gln Val Gln Trp Thr Asn Val
        435             440             445
Tyr Leu Asp Ala Leu Glu Leu Gly Leu Val Ile Thr Gly Thr Leu Pro
    450             455             460
Val Phe Asn Ile Thr Gly Gln Phe Glu Asn Lys Thr Asn Leu Lys Asn
465             470             475             480
Gln Leu Ile Leu Gly Val Met Gly Val Asp Val Ser Leu Glu Asp Ile
                485             490             495
Lys Arg Leu Thr Pro Arg Phe Thr Leu Cys Pro Asn
            500             505
```